United States Patent
Kumar et al.

(10) Patent No.: US 7,466,469 B2
(45) Date of Patent: Dec. 16, 2008

(54) POLARIZING, PHOTOCHROMIC DEVICES AND METHODS OF MAKING THE SAME

(75) Inventors: Anil Kumar, Pittsburgh, PA (US); Peter C. Foller, Murrysville, PA (US); Forrest R. Blackburn, Monroeville, PA (US); Jiping Shao, Monroeville, PA (US); Meng He, Murrysville, PA (US); Terry A. Kellar, II, Monroeville, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 11/590,367

(22) Filed: Oct. 31, 2006

(65) Prior Publication Data

US 2007/0047053 A1    Mar. 1, 2007

Related U.S. Application Data

(62) Division of application No. 10/846,650, filed on May 17, 2004, now Pat. No. 7,256,921.

(60) Provisional application No. 60/484,100, filed on Jul. 1, 2003.

(51) Int. Cl.
*G02F 1/03* (2006.01)

(52) U.S. Cl. .................................... 359/241

(58) Field of Classification Search .......... 359/241, 359/270, 271, 272, 273, 485, 488, 489, 493, 359/900; 351/44, 163, 49, 177; 349/13
See application file for complete search history.

(56) References Cited

U.S. PATENT DOCUMENTS

| | | | |
|---|---|---|---|
| 2,319,826 A | 5/1943 | Land |
| 2,334,446 A | 11/1943 | Serrell |
| 2,475,921 A | 7/1949 | Smith |
| 2,481,830 A | 9/1949 | Dreyer |
| 2,544,659 A | 3/1951 | Dreyer |
| 3,276,316 A | 10/1966 | Makas |
| 3,361,706 A | 1/1968 | Meriwether et al. |
| 3,653,863 A | 4/1972 | Araujo et al. |
| 4,039,254 A | 8/1977 | Harsch |
| 4,043,637 A | 8/1977 | Hovey |

(Continued)

FOREIGN PATENT DOCUMENTS

EP    0321563 B1    6/1989

(Continued)

OTHER PUBLICATIONS

Hikmet, R.A.M and de Witz, C., "Gel Layer for Inducting Adjustable Pretilt Angles in Liquid Crystal Systems," *J. App. Phys.* vol. 70, No. 3, pp. 1265-1266 (Aug. 1991).

(Continued)

*Primary Examiner*—Ricky Mack
*Assistant Examiner*—Tuyen Q Tra
(74) *Attorney, Agent, or Firm*—Frank P. Mallak; Deborah M. Altman

(57) ABSTRACT

A method of making an optical element including forming an at least partial coating of at least one at least partially aligned thermally reversible photochromic-dichroic compound on at least a portion of a substrate.

28 Claims, 1 Drawing Sheet

U.S. PATENT DOCUMENTS

Figure 1:
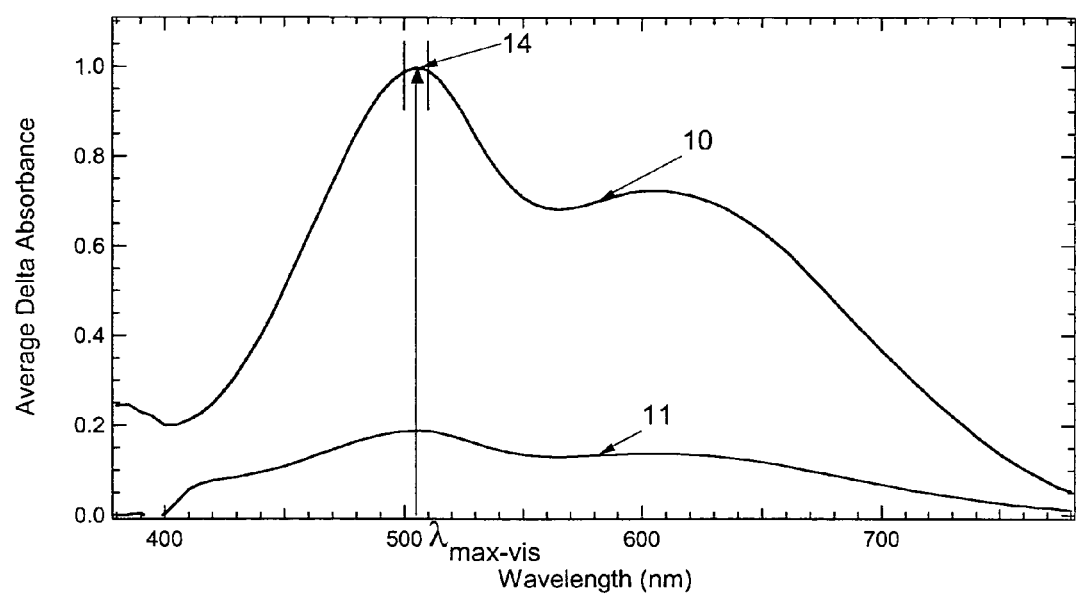

| Patent Number | | Date | Inventor |
|---|---|---|---|
| 4,049,338 | A | 9/1977 | Slocum |
| 4,166,043 | A | 8/1979 | Uhlmann et al. |
| 4,190,330 | A | 2/1980 | Berreman |
| 4,367,170 | A | 1/1983 | Uhlmann et al. |
| 4,549,894 | A | 10/1985 | Araujo et al. |
| 4,556,605 | A | 12/1985 | Mogami et al. |
| 4,637,896 | A | 1/1987 | Shannon |
| 4,648,925 | A | 3/1987 | Goepfert et al. |
| 4,683,153 | A | 7/1987 | Goepfert et al. |
| 4,728,173 | A | 3/1988 | Toth |
| 4,756,605 | A | 7/1988 | Okada et al. |
| 4,756,973 | A | 7/1988 | Sakagami et al. |
| 4,810,433 | A | 3/1989 | Takayanagi et al. |
| 4,838,673 | A | 6/1989 | Richards et al. |
| 4,863,763 | A | 9/1989 | Takeda et al. |
| 4,865,668 | A | 9/1989 | Goepfert et al. |
| 4,873,026 | A | 10/1989 | Behre et al. |
| 4,873,029 | A | 10/1989 | Blum |
| 4,931,220 | A | 6/1990 | Haynes et al. |
| 4,974,941 | A | 12/1990 | Gibbons et al. |
| 4,977,028 | A | 12/1990 | Goepfert et al. |
| 5,024,850 | A | 6/1991 | Broer et al. |
| 5,067,795 | A | 11/1991 | Senatore |
| 5,073,294 | A | 12/1991 | Shannon et al. |
| 5,130,353 | A | 7/1992 | Fischer et al. |
| 5,155,607 | A | 10/1992 | Inoue et al. |
| 5,180,470 | A | 1/1993 | Smith et al. |
| 5,185,390 | A | 2/1993 | Fischer et al. |
| 5,189,448 | A | 2/1993 | Yaguchi |
| 5,202,053 | A | 4/1993 | Shannon |
| 5,247,377 | A | 9/1993 | Omeis et al. |
| 5,464,669 | A | 11/1995 | Kang et al. |
| 5,602,661 | A | 2/1997 | Schadt et al. |
| 5,608,567 | A | 3/1997 | Grupp |
| 5,641,846 | A | 6/1997 | Bieringer et al. |
| 5,644,416 | A | 7/1997 | Morikawa et al. |
| 5,645,767 | A | 7/1997 | Van Gemert |
| 5,658,501 | A | 8/1997 | Kumar et al. |
| 5,698,141 | A | 12/1997 | Kumar |
| 5,723,072 | A | 3/1998 | Kumar |
| 5,746,949 | A | 5/1998 | Shen et al. |
| 5,846,452 | A | 12/1998 | Gibbons et al. |
| 5,903,330 | A | 5/1999 | Fünfschilling et al. |
| 5,943,104 | A | 8/1999 | Moddel et al. |
| 5,952,515 | A | 9/1999 | Melzig et al. |
| 5,962,617 | A | 10/1999 | Slagel |
| 6,022,497 | A | 2/2000 | Kumar |
| 6,025,026 | A | 2/2000 | Smith et al. |
| 6,036,890 | A | 3/2000 | Melzig et al. |
| 6,049,428 | A | 4/2000 | Khan et al. |
| 6,060,001 | A | 5/2000 | Welch et al. |
| 6,080,338 | A | 6/2000 | Kumar |
| 6,113,814 | A | 9/2000 | Gemert et al. |
| 6,136,968 | A | 10/2000 | Chamontin et al. |
| 6,150,430 | A | 11/2000 | Walters et al. |
| 6,153,126 | A | 11/2000 | Kumar |
| 6,160,597 | A | 12/2000 | Schadt et al. |
| 6,187,444 | B1 | 2/2001 | Bowles, III et al. |
| 6,239,778 | B1 | 5/2001 | Palffy-Muhoray et al. |
| 6,245,399 | B1 | 6/2001 | Sahouani et al. |
| 6,268,055 | B1 | 7/2001 | Walters et al. |
| 6,281,366 | B1 | 8/2001 | Frigoli et al. |
| 6,284,418 | B1 | 9/2001 | Trantolo |
| 6,296,785 | B1 | 10/2001 | Nelson et al. |
| 6,312,811 | B1 | 11/2001 | Frigoli et al. |
| 6,328,446 | B1 * | 12/2001 | Bhalakia et al. ............ 351/163 |
| 6,334,681 | B1 | 1/2002 | Perrott et al. |
| 6,338,808 | B1 | 1/2002 | Kawata et al. |
| 6,348,604 | B1 | 2/2002 | Nelson et al. |
| 6,353,102 | B1 | 3/2002 | Kumar |
| 6,369,869 | B2 | 4/2002 | Schadt et al. |
| 6,432,544 | B1 | 8/2002 | Stewart et al. |
| 6,433,043 | B1 | 8/2002 | Misura et al. |
| 6,436,525 | B1 | 8/2002 | Welch et al. |
| 6,474,695 | B1 | 11/2002 | Schneider et al. |
| 6,506,488 | B1 | 1/2003 | Stewart et al. |
| 6,531,076 | B2 | 3/2003 | Crano et al. |
| 6,555,028 | B2 | 4/2003 | Walters et al. |
| 6,597,422 | B1 | 7/2003 | Fünfschilling et al. |
| 6,602,603 | B2 | 8/2003 | Welch et al. |
| 6,613,433 | B2 | 9/2003 | Yamamoto et al. |
| 6,630,597 | B1 | 10/2003 | Lin et al. |
| 6,641,874 | B2 | 11/2003 | Kuntz et al. |
| 6,690,495 | B1 | 2/2004 | Kosa et al. |
| 6,705,569 | B1 | 3/2004 | Sanders et al. |
| 6,717,644 | B2 | 4/2004 | Schadt et al. |
| 6,761,452 | B2 | 7/2004 | Moravec et al. |
| 6,844,686 | B1 | 1/2005 | Schneck et al. |
| 6,874,888 | B1 | 4/2005 | Dudai |
| 2002/0039627 | A1 | 4/2002 | Ichihashi et al. |
| 2002/0090516 | A1 | 7/2002 | Loshak et al. |
| 2002/0167639 | A1 | 11/2002 | Coates et al. |
| 2002/0180916 | A1 | 12/2002 | Schadt et al. |
| 2003/0008958 | A1 | 1/2003 | Momoda et al. |
| 2003/0045612 | A1 | 3/2003 | Misura et al. |
| 2003/0189684 | A1 | 10/2003 | Kuntz et al. |
| 2004/0046927 | A1 | 3/2004 | Montgomery |
| 2004/0125337 | A1 | 7/2004 | Boulineau et al. |
| 2004/0158028 | A1 | 8/2004 | Bühler |
| 2004/0223221 | A1 | 11/2004 | Sugmura et al. |
| 2005/0003107 | A1 | 1/2005 | Kumar et al. |
| 2005/0004361 | A1 | 1/2005 | Kumar et al. |
| 2005/0012998 | A1 | 1/2005 | Kumar et al. |
| 2005/0146680 | A1 | 7/2005 | Muisener et al. |

FOREIGN PATENT DOCUMENTS

| | | |
|---|---|---|
| EP | 0 488 164 A2 | 11/1991 |
| EP | 0 543 678 A1 | 5/1993 |
| EP | 0619358 A1 | 10/1994 |
| EP | 0 397 263 B1 | 12/1994 |
| EP | 0 772 069 A1 | 10/1996 |
| EP | 0 331 233 B1 | 4/1997 |
| EP | 0965628 A1 | 12/1999 |
| GB | 583842 | 1/1947 |
| GB | 2 169 417 A | 7/1986 |
| JP | 59 135428 A | 8/1984 |
| JP | 03 200118 A | 9/1991 |
| JP | 03 200218 A | 9/1991 |
| WO | WO 89/05464 | 6/1989 |
| WO | WO 92/01959 | 2/1992 |
| WO | WO 93/17071 A1 | 9/1993 |
| WO | WO 98/19207 | 5/1998 |
| WO | WO 00/15630 | 3/2000 |
| WO | WO 00/19252 | 4/2000 |
| WO | WO 01/02449 | 1/2001 |
| WO | WO 01/19813 A1 | 3/2001 |
| WO | WO 01/70719 A2 | 9/2001 |
| WO | WO 03/032066 A1 | 4/2003 |
| WO | WO 2005/084826 A1 | 9/2005 |
| WO | WO 2005/085912 A1 | 9/2005 |

OTHER PUBLICATIONS

Kvasnikov, E.D., Kozenkov, V.M., and Barachevskii, V.A., "Birefringence in Polyvinylcinnamate Films Induced By Polarized Light," *Doklady Akademii nauk SSSR*, vol. 237, No. 3, USSR pp. 633-636 (1977).

Kozenkov, V.M., Chigrinov, V.G., and Kwok, H.S. "Photoanisotropic Effects in Poly (Vinyl-Cinnamate) Derivatives and Their Applications," *Mol. Cryst. Liq. Cryst.*, vol. 409, pp. 251-267 (2004).

Schadt, Martin et al. "Surface-Induced Parallel Alignment of Liquid Crystals by Linearly Polymerized Photopolymers," *Jpn. J. Appl. Phys.* vol. 31, No. 7, pp. 2155-2164 (Jul. 1992).

Schadt, Martin "Optics and Applications of Photo-Aligned Liquid Crystalline Surfaces," *Nonlinear Optics*, vol. 25, pp. 1-12 (2000).

Schadt, Martin "Liquid Crystal Displays and Novel Optical Thin Films Enabled by Photo-Alignment," *Mol. Cryst. Liq. Cryst.* vol. 364, pp. 151-169 (2001).

Dyadyusha, A.G. et al. "Light-Induced Planar Orientation of a Nematic Liquid Crystal on an Anisotropic Surface without Microrelief," *Ukr. Fiz. Zhurn*, (Ukraine), vol. 35, No. 5, pp. 1059-1062.

Dyadyusha, A.G. et al. "Light-Induced Planar Orientation of a Nematic Liquid Crystal on an Anisotropic Surface without Microrelief," *Ukr. Fiz. Zhurn*, (Ukraine), vol. 36 No. 7 pp. 1059-1062(1991).

Castellano, Joseph A. "Surface Anchoring of Liquid Crystal Molecules on Various Substrates," *Mol. Cryst. Liq. Cryst.*, vol. 94, pp. 33-41 (1983).

Huang, D.D. et al. "Effect of Aligning Layer Thickness on Photo-Aligned Ferroelectric Liquid Crystal Displays," *Proceedings of the 6th Chinese Optoelectronics Symposium*, Hong Kong China, IEEE (New York), pp. 231-234 (2003).

Chigrinov, V.G. and Kozenkov, V.M., "New Results on Liquid Crystal Alignment by Photopolymerization," *Proceedings of the SPIE-The Internationali Society for Optical Engineering*, SPIE vol. 2409 pp. 130-140 (1995).

* cited by examiner

POLARIZING, PHOTOCHROMIC DEVICES AND METHODS OF MAKING THE SAME

CROSS-REFERENCE TO RELATED APPLICATIONS

This application is a division of U.S. patent application Ser. No. 10/846,650, filed May 17, 2004, now issued as U.S. Pat. No. 7,256,921B2, which claims the benefit of priority from U.S. Provisional Application No. 60/484,100 filed Jul. 1, 2003, incorporated herein in its entirety.

STATEMENT REGARDING FEDERALLY SPONSORED RESEARCH OR DEVELOPMENT

Not applicable.

REFERENCE TO A SEQUENCE LISTING

Not applicable.

BACKGROUND

Various embodiments disclosed herein relate generally to optical elements, security liquid crystal cells and methods of making the same.

Conventional, linearly polarizing elements, such as linearly polarizing lenses for sunglasses and linearly polarizing filters, are typically formed from stretched polymer sheets containing a dichroic material, such as a dichroic dye. Consequently, conventional linearly polarizing elements are static elements having a single, linearly polarizing state. Accordingly, when a conventional linearly polarizing element is exposed to either randomly polarized radiation or reflected radiation of the appropriate wavelength, some percentage of the radiation transmitted through the element will be linearly polarized. As used herein the term "linearly polarize" means to confine the vibrations of the electric vector of light waves to one direction or plane.

Further, conventional linearly polarizing elements are typically tinted. That is, conventional linearly polarizing elements contain a coloring agent (i.e., the dichroic material) and have an absorption spectrum that does not vary in response to actinic radiation. As used herein "actinic radiation" means electromagnetic radiation, such as but not limited to ultraviolet and visible radiation that is capable of causing a response. The color of the conventional linearly polarizing element will depend upon the coloring agent used to form the element, and most commonly, is a neutral color (for example, brown or gray). Thus, while conventional linearly polarizing elements are useful in reducing reflected light glare, because of their tint, they are not well suited for use under certain low-light conditions. Further, because conventional linearly polarizing elements have only a single, tinted linearly polarizing state, they are limited in their ability to store or display information.

As discussed above, conventional linearly polarizing elements are typically formed using sheets of stretched polymer films containing a dichroic material. As used herein the term "dichroic" means capable of absorbing one of two orthogonal plane polarized components of at least transmitted radiation more strongly than the other. Thus, while dichroic materials are capable of preferentially absorbing one of two orthogonal plane polarized components of transmitted radiation, if the molecules of the dichroic material are not suitably positioned or arranged, no net linear polarization of transmitted radiation will be achieved. That is, due to the random positioning of the molecules of the dichroic material, selective absorption by the individual molecules will cancel each other such that no net or overall linear polarizing effect is achieved. Thus, it is generally necessary to suitably position or arrange the molecules of the dichroic material by alignment with another material in order to achieve a net linear polarization.

One common method of aligning the molecules of a dichroic dye involves heating a sheet or layer of polyvinyl alcohol ("PVA") to soften the PVA and then stretching the sheet to orient the PVA polymer chains. Thereafter, the dichroic dye is impregnated into the stretched sheet and dye molecules take on the orientation of the polymer chains. That is, the dye molecules become aligned such that the long axis of the dye molecule are generally parallel to the oriented polymer chains. Alternatively, the dichroic dye can be first impregnated into the PVA sheet, and thereafter the sheet can be heated and stretched as described above to orient the PVA polymer chains and associated dye. In this manner, the molecules of the dichroic dye can be suitably positioned or arranged within the oriented polymer chains of the PVA sheet and a net linear polarization can be achieved. That is, the PVA sheet can be made to linearly polarize transmitted radiation, or in other words, a linearly polarizing filter can be formed.

In contrast to the dichroic elements discussed above, conventional photochromic elements, such as photochromic lenses that are formed using conventional thermally reversible photochromic materials are generally capable of converting from a first state, for example a "clear state," to a second state, for example a "colored state," in response to actinic radiation, and reverting back to the first state in response to thermal energy. As used herein the term "photochromic" means having an absorption spectrum for at least visible radiation that varies in response to at least actinic radiation. Thus, conventional photochromic elements are generally well suited for use in both low-light and bright conditions. However, conventional photochromic elements that do not include linearly polarizing filters are generally not adapted to linearly polarize radiation. That is, the absorption ratio of conventional photochromic elements, in either state, is generally less than two. As used herein the term "absorption ratio" refers to the ratio of the absorbance of radiation linearly polarized in a first plane to the absorbance of the same wavelength radiation linearly polarized in a plane orthogonal to the first plane, wherein the first plane is taken as the plane with the highest absorbance. Therefore, conventional photochromic elements cannot reduce reflected light glare to the same extent as conventional linearly polarizing elements. Further, conventional photochromic elements have a limited ability to store or display information.

Accordingly, it would be advantageous to provide elements and devices that are adapted to display both linearly polarizing and photochromic properties. Further, it would be advantageous to provide elements and devices that are adapted to display circular or elliptical polarization and photochromic properties.

BRIEF SUMMARY OF THE DISCLOSURE

Various non-limiting embodiments disclosed herein relate to optical elements. For example, one non-limiting embodiment provides an optical element comprising an at least partial coating having a first state and a second state connected to at least a portion of a substrate, the at least partial coating being adapted to switch from the first state to the second state in response to at least actinic radiation, to revert back to the first state in response to thermal energy, and to linearly polarize at least transmitted radiation in at least one of the first state and the second state.

Another non-limiting embodiment provides an optical element comprising a substrate, and at least one at least partially aligned thermally reversible photochromic-dichroic compound connected to at least a portion of the substrate and having an average absorption ratio greater than 2.3 in an activated state as determined according to CELL METHOD.

Still another non-limiting embodiment provides an optical element comprising a substrate, at least one at least partially ordered orientation facility connected to at least a portion of the substrate, and an at least partial coating connected to at least a portion of the at least partially ordered orientation facility, the at least partial coating comprising at least one at least partially ordered anisotropic material and at least one photochromic-dichroic compound that is at least partially aligned with at least a portion of the at least partially ordered anisotropic material.

Yet another non-limiting embodiment provides an optical element comprising a substrate, a first at least partial coating comprising an at least partially ordered alignment medium connected to at least a portion of at least one surface of the substrate, a second at least partial coating comprising an alignment transfer material that is connected to and at least partially aligned with at least a portion of the at least partially ordered alignment medium, and a third at least partial coating connected to at least a portion of the alignment transfer material, the third at least partial coating comprising at least one anisotropic material that is at least partially aligned with at least a portion of the at least partially aligned alignment transfer material and at least one photochromic-dichroic compound that is at least partially aligned with at least a portion of the at least partially aligned anisotropic material.

Other non-limiting embodiments relate to composite optical elements. For example, one non-limiting embodiment provides a composite optical element comprising a substrate, an at least partially ordered polymeric sheet connected to at least a portion of the substrate, and at least one thermally reversible photochromic-dichroic compound that is at least partially aligned with at least a portion of the at least partially ordered polymeric sheet and has an average absorption ratio greater than 2.3 in the activated state as determined according to CELL METHOD.

Another non-limiting embodiment provides a composite optical element comprising a substrate, and at least one sheet connected to at least a portion of the substrate, the at least one sheet comprising an at least partially ordered liquid crystal polymer having at least a first general direction, at least one at least partially ordered liquid crystal material having at least a second general direction that is generally parallel to at least the first general direction distributed within at least a portion of the liquid crystal polymer, and at least one photochromic-dichroic compound that is at least partially aligned with at least a portion of the at least one at least partially ordered liquid crystal material.

Still other non-limiting embodiments relate to methods of making optical elements. For example, one non-limiting embodiment provides a method of making an optical element comprising forming an at least partial coating comprising at least one at least partially aligned thermally reversible photochromic-dichroic compound on at least a portion of a substrate.

Another non-limiting embodiment provides a method of making an optical element comprising: (a) forming an at least partial coating on at least a portion of a substrate, and (b) adapting at least a portion of the at least partial coating to switch from a first state to a second linearly polarizing state in response to actinic radiation and to revert back to the first sate in response to thermal energy.

Still another non-limiting embodiment provides a method of making an optical element comprising: forming an at least partial coating comprising an alignment medium to at least a portion of at least one surface of a substrate and at least partially ordering at least a portion of the alignment medium, forming at least one at least partial coating comprising an alignment transfer material on at least a portion of the at least partial coating comprising the alignment medium and at least partially aligning at least a portion of the alignment transfer material with at least a portion of the at least partially ordered alignment medium, and forming an at least partial coating comprising an anisotropic material and at least one photochromic-dichroic compound on at least a portion of the alignment transfer material, at least partially aligning at least a portion of the anisotropic material with at least a portion of the at least partially aligned alignment transfer material, and at least partially aligning at least a portion of the at least one photochromic-dichroic compound with at least a portion of the at least partially aligned anisotropic material.

Still another non-limiting embodiment provides a method of making a composite element comprising connecting an at least partially ordered polymeric sheet to at least a portion of a substrate, the at least partially ordered polymeric sheet comprising at least one at least partially aligned thermally reversible photochromic-dichroic compound connected to at least a portion thereof and having an average absorption ratio greater than 2.3 in an activated state as determined according to CELL METHOD.

Yet another non-limiting embodiment provides a method of making a composite element comprising: forming a sheet comprising an at least partially ordered liquid crystal polymer having at least a first general direction, a liquid crystal material having at least a second general direction distributed within at least a portion of the liquid crystal polymer; and at least one photochromic-dichroic compound that is at least partially aligned with at least portion of the liquid crystal material; and connecting at least a portion of the sheet to at least a portion of an optical substrate to form the composite element.

Still another non-limiting embodiment provides a method of making a composite element comprising forming a sheet comprising an at least partially ordered liquid crystal polymer having at least a first general direction and a liquid crystal material having at least a second general direction distributed within at least a portion of the liquid crystal polymer, connecting at least a portion of the sheet to at least a portion of an optical substrate, and imbibing at least one photochromic-dichroic compound into at least a portion of the sheet.

Another non-limiting embodiment provides a method of making an optical element comprising overmolding an at least partial coating comprising an at least partially ordered liquid crystal material and at least one at least partially aligned photochromic-dichroic compound on at least a portion of an optical substrate.

Still another non-limiting embodiment provides a method of making an optical element comprising overmolding an at least partial coating comprising an at least partially ordered liquid crystal material on at least a portion of an optical substrate; and imbibing at least one photochromic-dichroic compound into at least a portion of the at least partially ordered liquid crystal material.

Other non-limiting embodiments relate to security elements. For example, one non-limiting embodiment provides a security element connected to at least a portion of a substrate, the security element comprising an at least partial coating having a first state and a second state connected to at least a portion of the substrate, the at least partial coating being adapted to switch from a first state to a second state in response to at least actinic radiation, to revert back to the first state in response to thermal energy, and to linearly polarize at least transmitted radiation in at least one of the first state and the second state.

Another non-limiting embodiment provides a method of making a security element comprising forming an at least partial coating on at least a portion of the substrate, the at least partial coating comprising at least one at least partially aligned, thermally reversible photochromic-dichroic compound.

Other non-limiting embodiments relate to liquid crystal cells. For example, one non-limiting embodiment provides a liquid crystal cell comprising a first substrate having a first surface, a second substrate having a second surface, wherein the second surface of the second substrate is opposite and spaced apart from the first surface of the first substrate so as to define an region, and a liquid crystal material adapted to be at least partially ordered and at least one thermally reversible photochromic-dichroic compound adapted to be at least partially aligned and having an average absorption ratio greater than 2.3 in an activated state as determined according to CELL METHOD positioned within the region defined by the first surface and the second surface.

Another non-limiting embodiment provides an optical element comprising a substrate; and an at least partial coating having a first state and a second state on at least a portion of the substrate, the at least partial coating being adapted to be circularly polarizing or elliptically polarizing in at least one state and comprising a chiral nematic or cholesteric liquid crystal material having molecules that are helically arranged through a thickness of the at least partial coating, and at least one photochromic-dichroic compound that is at least partially aligned with the liquid crystal material such that a long axis of a molecule of the at least one photochromic-dichroic compound is generally parallel to the molecules of the liquid crystal material.

Another non-limiting embodiment provides an optical element a substrate; and an at least partial coating connected to at least a portion of the substrate, the at least partial coating comprising an at least partially ordered anisotropic material and at least one photochromic-dichroic compound that is at least partially aligned with the at least partially ordered anisotropic material, said photochromic-dichroic compound comprising: (a) at least one photochromic group chosen from a pyran, an oxazine, and a fulgide; and (b) at least one lengthening agent L attached to the at least one photochromic group and represented by:

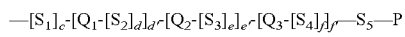

which is set forth herein below in detail.

BRIEF DESCRIPTION OF THE SEVERAL VIEWS OF THE DRAWING(S)

Figure 2:
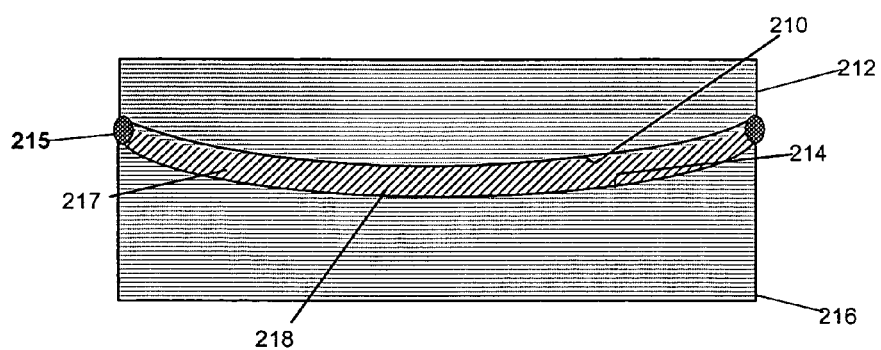

Various non-limiting embodiments of the present invention will be better understood when read in conjunction with the drawings, in which:

FIG. 1 shows two average difference absorption spectra obtained for a coating according to various non-limiting embodiment disclosed herein; and FIG. 2 is a schematic, cross-sectional view of an overmolding assembly according to one non-limiting embodiment disclosed herein.

DETAILED DESCRIPTION OF EMBODIMENTS

As used in this specification and the appended claims, the articles "a," "an," and "the" include plural referents unless expressly and unequivocally limited to one referent.

Additionally, for the purposes of this specification, unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from the measurement equipment and/or measurement technique.

Optical elements and devices according to various non-limiting embodiments of the present invention will now be described. Various non-limiting embodiments disclosed herein provide an optical element comprising an at least partial coating having a first state and a second state connected to at least a portion of at least one surface of a substrate, the at least partial coating being adapted to switch from the first state to the second state in response to at least actinic radiation, to revert back to the first state in response to thermal energy, and to linearly polarize at least transmitted radiation in at least one of the first state and the second state. As used herein, the term "thermal energy" means any form of heat.

As used herein to modify the term "state," the terms "first" and "second" are not intended to refer to any particular order or chronology, but instead refer to two different conditions or properties. For example, although not limiting herein, the first state and the second state of the coating may differ with respect to at least one optical property, such as but not limited to the absorption or linearly polarization of visible and/or UV radiation. Thus, according to various non-limiting embodiments disclosed herein, the at least partial coating can be adapted to have a different absorption spectrum in each of the first and second state. For example, while not limiting herein, the at least partial coating can be clear in the first state and colored in the second state. Alternatively, the at least partial coating can be adapted to have a first color in the first state and a second color in the second state. Further, as discussed below in more detail, the at least partial coating can be adapted to not be linearly polarizing (or "non-polarizing") in the first state and linearly polarizing in the second state.

As used herein the term "optical" means pertaining to or associated with light and/or vision. For example, according to various non-limiting embodiments disclosed herein, the optical element or device can be chosen from ophthalmic elements and devices, display elements and devices, windows, mirrors, and active and passive liquid crystal cell elements and devices. As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors. As used herein the term "display" means the visible or machine-readable representation of information in words, numbers, symbols, designs or drawings. Non-limiting examples of display elements and devices include screens, monitors, and security elements, such as security marks. As used herein the term "window" means an aperture adapted to permit the transmission of radiation therethrough. Non-limiting examples of windows include automotive and aircraft transparencies, filters, shutters, and optical switches. As used herein the term "mirror" means a surface that specularly reflects a large fraction of incident light.

As used herein the term "liquid crystal cell" refers to a structure containing a liquid crystal material that is capable of being ordered. Active liquid crystal cells are cells wherein the liquid crystal material is capable of being switched between ordered and disordered states or between two ordered states by the application of an external force, such as electric or magnetic fields. Passive liquid crystal cells are cells wherein the liquid crystal material maintains an ordered state. One non-limiting example of an active liquid crystal cell element or device is a liquid crystal display.

As discussed above, one non-limiting embodiment provides, in part, an optical element comprising an at least partial coating having a first state and a second state connected to at least a portion of at least one surface of a substrate. As used herein the term "coating" means a supported film derived from a flowable composition, which may or may not have a uniform thickness, and specifically excludes polymeric sheets. As used herein the term "sheet" means a pre-formed film having a generally uniform thickness and capable of self-support. Further, as used herein the term "connected to" means in direct contact with an object or indirect contact with an object through one or more other structures or materials, at least one of which is in direct contact with the object. Thus, according to various non-limiting embodiments disclosed herein, the at least partial coating having the first state and the second state can be in direct contact with at least a portion of the substrate or it can be in indirect contact with at least a portion of the substrate through one or more other structures or materials. For example, although not limiting herein, the at least partial coating can be in contact with one or more other at least partial coatings, polymer sheets or combinations thereof, at least one of which is in direct contact with at least a portion of the substrate.

Generally speaking, substrates that are suitable for use in conjunction with various non-limiting embodiments disclosed herein include, but are not limited to, substrates formed from organic materials, inorganic materials, or combinations thereof (for example, composite materials). Non-limiting examples of substrates that can be used in accordance with various non-limiting embodiments disclosed herein are described in more detail below.

Specific, non-limiting examples of organic materials that may be used to form the substrates disclosed herein include polymeric materials, for examples, homopolymers and copolymers, prepared from the monomers and mixtures of monomers disclosed in U.S. Pat. Nos. 5,962,617 and in 5,658,501 from column 15, line 28 to column 16, line 17, the disclosures of which U.S. patents are specifically incorporated herein by reference. For example, such polymeric materials can be thermoplastic or thermoset polymeric materials, can be transparent or optically clear, and can have any refractive index required. Non-limiting examples of such disclosed monomers and polymers include: polyol(allyl carbonate) monomers, e.g., allyl diglycol carbonates such as diethylene glycol bis(allyl carbonate), which monomer is sold under the trademark CR-39 by PPG Industries, Inc.; polyurea-polyurethane (polyurea-urethane) polymers, which are prepared, for example, by the reaction of a polyurethane prepolymer and a diamine curing agent, a composition for one such polymer being sold under the trademark TRIVEX by PPG Industries, Inc.; polyol(meth)acryloyl terminated carbonate monomer; diethylene glycol dimethacrylate monomers; ethoxylated phenol methacrylate monomers; diisopropenyl benzene monomers; ethoxylated trimethylol propane triacrylate monomers; ethylene glycol bismethacrylate monomers; poly(ethylene glycol)bismethacrylate monomers; urethane acrylate monomers; poly(ethoxylated bisphenol A dimethacrylate); poly(vinyl acetate); poly(vinyl alcohol); poly(vinyl chloride); poly(vinylidene chloride); polyethylene; polypropylene; polyurethanes; polythiourethanes; thermoplastic polycarbonates, such as the carbonate-linked resin derived from bisphenol A and phosgene, one such material being sold under the trademark LEXAN; polyesters, such as the material sold under the trademark MYLAR; poly(ethylene terephthalate); polyvinyl butyral; poly(methyl methacrylate), such as the material sold under the trademark PLEXIGLAS, and polymers prepared by reacting polyfunctional isocyanates with polythiols or polyepisulfide monomers, either homopolymerized or co- and/or terpolymerized with polythiols, polyisocyanates, polyisothiocyanates and optionally ethylenically unsaturated monomers or halogenated aromatic-containing vinyl monomers. Also contemplated are copolymers of such monomers and blends of the described polymers and copolymers with other polymers, for example, to form block copolymers or interpenetrating network products.

While not limiting herein, according to various non-limiting embodiments disclosed herein, the substrate can be an ophthalmic substrate. As used herein the term "ophthalmic substrate" means lenses, partially formed lenses, and lens blanks. Non-limiting examples of organic materials suitable for use in forming ophthalmic substrates according to various non-limiting embodiments disclosed herein include, but are not limited to, the art-recognized polymers that are useful as ophthalmic substrates, e.g., organic optical resins that are used to prepare optically clear castings for optical applications, such as ophthalmic lenses.

Other non-limiting examples of organic materials suitable for use in forming the substrates according to various non-limiting embodiments disclosed herein include both synthetic and natural organic materials, including without limitation: opaque or transluscent polymeric materials, natural and synthetic textiles, and cellulosic materials such as, paper and wood.

Non-limiting examples of inorganic materials suitable for use in forming the substrates according to various non-limiting embodiments disclosed herein include glasses, minerals, ceramics, and metals. For example, in one non-limiting embodiment the substrate can comprise glass. In other non-limiting embodiments, the substrate can have a reflective surface, for example, a polished ceramic substrate, metal substrate, or mineral substrate. In other non-limiting embodiments, a reflective coating or layer can be deposited or otherwise applied to a surface of an inorganic or an organic substrate to make it reflective or to enhance its reflectivity.

Further, according to certain non-limiting embodiments disclosed herein, the substrates may have a protective coating, such as, but not limited to, an abrasion-resistant coating, such as a "hard coat," on their exterior surfaces. For example, commercially available thermoplastic polycarbonate ophthalmic lens substrates are often sold with an abrasion-resistant coating already applied to its exterior surfaces because these surfaces tend to be readily scratched, abraded or scuffed. An example of such a lens substrate is the GENTEX™ polycarbonate lens (available from Gentex Optics). Therefore, as used herein the term "substrate" includes a substrate having a protective coating, such as but not limited to an abrasion-resistant coating, on its surface(s).

Still further, the substrates according to various non-limiting embodiments disclosed herein can be untinted, tinted, linearly polarizing, circularly polarizing, elliptically polarizing, photochromic, or tinted-photochromic substrates. As used herein with reference to substrates the term "untinted" means substrates that are essentially free of coloring agent additions (such as, but not limited to, conventional dyes) and have an absorption spectrum for visible radiation that does not vary significantly in response to actinic radiation. Further, with reference to substrates the term "tinted" means substrates that have a coloring agent addition (such as, but not limited to, conventional dyes) and an absorption spectrum for visible radiation that does not vary significantly in response to actinic radiation.

As used herein the term "linearly polarizing" with reference to substrates refers to substrates that are adapted to linearly polarize radiation. As used herein the term "circularly polarizing" with reference to substrates refers to substrates that are adapted to circularly polarize radiation. As used herein the term "elliptically polarizing" with reference to substrates refers to substrates that are adapted to elliptically polarize radiation. As used herein with the term "photochromic" with reference to substrates refers to substrates having an absorption spectrum for visible radiation that varies in response to at least actinic radiation. Further, as used herein with reference to substrates, the term "tinted-photochromic" means substrates containing a coloring agent addition as well as a photochromic material, and having an absorption spectrum for visible radiation that varies in response to at least actinic radiation. Thus, for example and without limitation, the tinted-photochromic substrate can have a first color characteristic of the coloring agent and a second color characteristic of the combination of the coloring agent the photochromic material when exposed to actinic radiation.

As previously discussed, conventional linearly polarizing elements are typically formed using stretched polymer sheets and a dichroic dye. However, these conventional linearly polarizing elements generally have a single tinted, linearly polarizing state. As previously discussed, the term "linearly polarize" means to confine the vibrations of the electric vector of light waves to one direction. Further, as previously discussed, conventional photochromic elements are formed from conventional photochromic compounds and have at least two states, for example a clear state and a colored state. As previously discussed, the term "photochromic" means having an absorption spectrum for at least visible radiation that varies in response to at least actinic radiation. However, conventional photochromic elements are generally not adapted to linearly polarize radiation.

As discussed above, the optical elements according to various non-limiting embodiments disclosed herein comprise an at least partial coating having a first state and a second state that is adapted to switch from the first state to the second state in response to actinic radiation, to revert back to the first state in response to thermal energy, and to be linearly polarizing in at least one of the first state and the second state. That is, the optical elements according to various non-limiting embodiments disclosed herein can be photochromic-dichroic elements. As used herein the term "photochromic-dichroic" means displaying both photochromic and dichroic (i.e., linearly polarizing) properties under certain conditions, which properties are at least detectible by instrumentation. Further, as discussed below in more detail, the optical elements according to various non-limiting embodiments disclosed herein can be formed using at least one photochromic-dichroic compound that is at least partially aligned.

As previously mentioned, according to various non-limiting embodiments disclosed herein, the at least partial coating can be adapted to be non-polarizing in the first state (that is, the coating will not confine the vibrations of the electric vector of light waves to one direction) and to linearly polarize at least transmitted radiation in the second state. As used herein the term "transmitted radiation" refers to radiation that is passed through at least a portion of an object. Although not limiting herein, the transmitted radiation can be ultraviolet radiation, visible radiation, or a combination thereof. Thus, according to various non-limiting embodiments disclosed herein, the at least partial coating can be adapted to be non-polarizing in the first state and to linearly polarize transmitted ultraviolet radiation, transmitted visible radiation, or a combination thereof in the second state.

According to still other non-limiting embodiments, the at least partial coating having a first state and a second state can be adapted to have a first absorption spectrum in the first state, a second absorption spectrum in the second state, and to be linearly polarizing in both the first and second states.

According to one non-limiting embodiment, the at least partial coating having the first state and the second state can have an average absorption ratio of at least 1.5 in at least one state. According to another non-limiting embodiment, the at least partial coating can have an average absorption ratio ranging from at least 1.5 to 50 (or greater) in at least one state. As previously discussed, the term "absorption ratio" refers to the ratio of the absorbance of radiation linearly polarized in a first plane to the absorbance of radiation linearly polarized in a plane orthogonal to the first plane, wherein the first plane is taken as the plane with the highest absorbance. Thus, the absorption ratio (and the average absorption ratio which is described below) is an indication of how strongly one of two orthogonal plane polarized components of radiation is absorbed by an object or material.

The average absorption ratio of a coating or element comprising a photochromic-dichroic compound can be determined as set forth below. For example, to determine the average absorption ratio of a coating comprising a photochromic-dichroic compound, a substrate having a coating is positioned on an optical bench and the coating is placed in a linearly polarizing state by activation of the photochromic-dichroic compound. Activation is achieved by exposing the coating to UV radiation for a time sufficient to reach a saturated or near saturated state (that is, a state wherein the absorption properties of the coating do not substantially change over the interval of time during which the measurements are made). Absorption measurements are taken over a period of time (typically 10 to 300 seconds) at 3 second intervals for light that is linearly polarized in a plane perpendicular to the optical bench (referred to as the 0° polarization plane or direction) and light that is linearly polarized in a plane that is parallel to the optical bench (referred to as the 90° polarization plane or direction) in the following sequence: 0°, 90°, 90°, 0° etc. The absorbance of the linearly polarized light by the coating is measured at each time interval for all of the wavelengths tested and the unactivated absorbance (i.e., the absorbance of the coating in an unactivated state) over the same range of wavelengths is subtracted to obtain absorption spectra for the coating in an activated state in each of the 0° and 90° polarization planes to obtain an average difference absorption spectrum in each polarization plane for the coating in the saturated or near-saturated state.

For example, with reference to FIG. 1, there is shown the average difference absorption spectrum (generally indicated 10) in one polarization plane that was obtained for a coating according to one non-limiting embodiment disclosed herein. The average absorption spectrum (generally indicated 11) is the average difference absorption spectrum obtained for the same coating in the orthogonal polarization plane.

Based on the average difference absorption spectra obtained for the coating, the average absorption ratio for the coating is obtained as follows. The absorption ratio of the coating at each wavelength in a predetermined range of wavelengths corresponding to $\lambda_{max\text{-}vis}+/-5$ nanometers (generally indicated as 14 in FIG. 1), wherein $\lambda_{max\text{-}vis}$ is the wavelength at which the coating had the highest average absorbance in any plane, is calculated according to the following equation:

$$AR_{\lambda,i}=Ab^1_{\lambda,i}/Ab^2_{\lambda,i} \quad \text{Eq. 1}$$

wherein, $AR_{\lambda,i}$ is the absorption ratio at wavelength $\lambda_i$, $Ab^1_{\lambda,i}$ is the average absorption at wavelength $\lambda_i$ in the polarization direction (i.e., 0° or 90°) having the higher absorbance, and $Ab^2_{\lambda,i}$ is the average absorption at wavelength $\lambda_i$ in the remaining polarization direction. As previously discussed, the "absorption ratio" refers to the ratio of the absorbance of radiation linearly polarized in a first plane to the absorbance of the same wavelength radiation linearly polarized in a plane orthogonal to the first plane, wherein the first plane is taken as the plane with the highest absorbance.

The average absorption ratio ("AR") for the coating is then calculated by averaging the individual absorption ratios over the predetermined range of wavelengths (i.e., $\lambda_{max\text{-}vis}+/-5$ nanometers) according to the following equation:

$$AR=(\Sigma AR_{\lambda,i})/n_i \quad \text{Eq. 2}$$

wherein, AR is average absorption ratio for the coating, $AR_{\lambda,i}$ are the individual absorption ratios (as determined above in Eq. 1) for each wavelength within the predetermined range of wavelengths, and $n_i$ is the number of individual absorption ratios averaged. A more detailed description of this method of determining the average absorption ratio is provided in the Examples.

As previously mentioned, according to various non-limiting embodiments disclosed herein, the at least partial coating having the first state and the second state can comprise at least one photochromic-dichroic compound that is at least partially aligned. As previously discussed, the term "photochromic-dichroic" means displaying both photochromic and dichroic (i.e., linearly polarizing) properties under certain conditions, which properties are at least detectible by instrumentation. Accordingly, "photochromic-dichroic compounds" are compounds displaying both photochromic and dichroic (i.e., linearly polarizing) properties under certain conditions, which properties are at least detectible by instrumentation. Thus, photochromic-dichroic compounds have an absorption spectrum for at least visible radiation that varies in response to at least actinic radiation and are capable of absorbing one of two orthogonal plane polarized components of at least transmitted radiation more strongly than the other. Additionally, as with conventional photochromic compounds discussed above, the photochromic-dichroic compounds disclosed herein can be thermally reversible. That is, the photochromic-dichroic compounds can switch from a first state to a second state in response to actinic radiation and revert back to the first state in response to thermal energy. As used herein the term "compound" means a substance formed by the union of two or more elements, components, ingredients, or parts and includes, without limitation, molecules and macromolecules (for example polymers and oligomers) formed by the union of two or more elements, components, ingredients, or parts.

For example, according to various non-limiting embodiments disclosed herein, the at least one photochromic-dichroic compound can have a first state having a first absorption spectrum, a second state having a second absorption spectrum that is different from the first absorption spectrum, and can be adapted to switch from the first state to the second state in response to at least actinic radiation and to revert back to the first state in response to thermal energy. Further, the photochromic-dichroic compound can be dichroic (i.e., linearly polarizing) in one or both of the first state and the second state. For example, although not required, the photochromic-dichroic compound can be linearly polarizing in an activated state and non-polarizing in the bleached or faded (i.e., not activated) state. As used herein, the term "activated state" refers to the photochromic-dichroic compound when exposed to sufficient actinic radiation to cause the at least a portion of the photochromic-dichroic compound to switch from a first state to a second state. Further, although not required, the photochromic-dichroic compound can be dichroic in both the first and second states. While not limiting herein, for example, the photochromic-dichroic compound can linearly polarize visible radiation in both the activated state and the bleached state. Further, the photochromic-dichroic compound can linearly polarize visible radiation in an activated state, and can linearly polarize UV radiation in the bleached state.

Although not required, according to various non-limiting embodiments disclosed herein, the at least one photochromic-dichroic compound can have an average absorption ratio of at least 1.5 in an activated state as determined according to the CELL METHOD. According to other non-limiting embodiments disclosed herein, the at least one photochromic-dichroic compound can have an average absorption ratio greater than 2.3 in an activated state as determined according to the CELL METHOD. According to still other non-limiting embodiments, the at least one at least partially aligned photochromic-dichroic compound can have an average absorption ratio ranging from 1.5 to 50 in an activated state as determined according to the CELL METHOD. According to other non-limiting embodiments, the at least one at least partially aligned photochromic-dichroic compound can have an average absorption ratio ranging from 4 to 20, can further having an average absorption ratio ranging from 3 to 30, and can still further having an average absorption ratio ranging from 2.5 to 50 in an activated state as determined according to the CELL METHOD. However, generally speaking, the average absorption ratio of the at least one at least partially aligned photochromic-dichroic compound can be any average absorption ratio that is sufficient to impart the desired properties to the device or element. Non-limiting examples of suitable photochromic-dichroic compounds are described in detail herein below.

The CELL METHOD for determining the average absorption ratio of the photochromic-dichroic compound is essentially the same as the method used to determine the average absorption ratio of the at least partial coating (described above and in the Examples), except that, instead of measuring the absorbance of a coated substrate, a cell assembly containing an aligned liquid crystal material and the photochromic-dichroic compound is tested. More specifically, the cell assembly comprises two opposing glass substrates that are spaced apart by 20 microns+/−1 micron. The substrates are sealed along two opposite edges to form a cell. The inner surface of each of the glass substrates is coated with a polyimide coating, the surface of which has been at least partially ordered by rubbing. Alignment of the photochromic-dichroic compound is achieved by introducing the photochromic-dichroic compound and the liquid crystal medium into the cell assembly, and allowing the liquid crystal medium to align with the rubbed polyimide surface. Once the liquid crystal medium and the photochromic-dichroic compound are aligned, the cell assembly is placed on an optical bench (which is described in detail in the Examples) and the average absorption ratio is determined in the manner previously described for the coated substrates, except that the unactivated absorbance of the cell assembly is subtracted from the activated absorbance to obtain the average difference absorption spectra.

As previously discussed, while dichroic compounds are capable of preferentially absorbing one of two orthogonal components of plane polarized light, it is generally necessary to suitably position or arrange the molecules of a dichroic compound in order to achieve a net linear polarization effect. Similarly, it is generally necessary to suitably position or arrange the molecules of a photochromic-dichroic compound to achieve a net linear polarization effect. That is, it is generally necessary to align the molecules of the photochromic-dichroic compound such that the long axis of the molecules of the photochromic-dichroic compound in an activated state are generally parallel to each other. Therefore, as discussed above, according to various non-limiting embodiments disclosed herein, the at least one photochromic-dichroic compound is at least partially aligned. Further, if the activated state of the photochromic-dichroic compound corresponds to a dichroic state of the material, the at least one photochromic-dichroic compound can be at least partially aligned such that the long axis of the molecules of the photochromic-dichroic compound in the activated state are aligned. As used herein the term "align" means to bring into suitable arrangement or position by interaction with another material, compound or structure.

Further, although not limiting herein, the at least partial coating can comprise a plurality of photochromic-dichroic compounds. Although not limiting herein, when two or more photochromic-dichroic compounds are used in combination, the photochromic-dichroic compounds can be chosen to complement one another to produce a desired color or hue. For example, mixtures photochromic-dichroic compounds can be used according to certain non-limiting embodiments disclosed herein to attain certain activated colors, such as a near neutral gray or near neutral brown. See, for example, U.S. Pat. No. 5,645,767, column 12, line 66 to column 13, line 19, the disclosure of which is specifically incorporated by reference herein, which describes the parameters that define neutral gray and brown colors. Additionally or alternatively, the at least partial coating can comprise mixtures of photochromic-dichroic compounds having complementary linear polarization states. For example, the photochromic-dichroic compounds can be chosen to have complementary linear polarization states over a desired range of wavelengths to produce an optical element that is capable of polarizing light over the desired range of wavelengths. Still further, mixtures of complementary photochromic-dichroic compounds having essentially the same polarization states at the same wavelengths can be chosen to reinforce or enhance the overall linear polarization achieved. For example, according to one non-limiting embodiment, the at least partial coating having the first state and the second state can comprise at least two at least partially aligned photochromic-dichroic compounds, wherein the at least two at least partially aligned photochromic-dichroic compounds have at least one of: complementary colors and complementary linear polarization states.

As previously discussed, various non-limiting embodiments disclosed herein provide an optical element comprising an at least partial coating connected to at least a portion of a substrate, wherein the at least partial coating is adapted to switch from a first state to a second state in response to at least actinic radiation, to revert back to the first state in response to thermal energy, and to linearly polarize at least transmitted radiation in at least one of the first state and the second state. Further, according to various non-limiting embodiments, the at least partial coating can comprise at least one photochromic-dichroic compound that is at least partially aligned.

Additionally, according to various non-limiting embodiments disclosed herein, the at least partial coating having the first state and the second state can further comprise at least one additive that may facilitate one or more of the processing, the properties, or the performance of the at least partial coating. Non-limiting examples of such additives include dyes, alignment promoters, kinetic enhancing additives, photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, and adhesion promoters (such as hexanediol diacrylate and coupling agents).

Non-limiting examples of dyes that can be present in the at least partial coating according to various non-limiting embodiments disclosed herein include organic dyes that are capable of imparting a desired color or other optical property to the at least partial coating.

As used herein, the term "alignment promoter" means an additive that can facilitate at least one of the rate and uniformity of the alignment of a material to which it is added. Non-limiting examples of alignment promoters that can be present in the at least partial coatings according to various non-limiting embodiments disclosed herein include those described in U.S. Pat. No. 6,338,808 and U.S. Patent Publication No. 2002/0039627, which are hereby specifically incorporated by reference herein.

Non-limiting examples of kinetic enhancing additives that can be present in the at least partial coating according to various non-limiting embodiments disclosed herein include epoxy-containing compounds, organic polyols, and/or plasticizers. More specific examples of such kinetic enhancing additives are disclosed in U.S. Pat. No. 6,433,043 and U.S. Patent Publication No. 2003/0045612, which are hereby specifically incorporated by reference herein.

Non-limiting examples of photoinitiators that can be present in the at least partial coating according to various non-limiting embodiments disclosed herein include cleavage-type photoinitiators and abstraction-type photoinitiators. Non-limiting examples of cleavage-type photoinitiators include acetophenones, α-aminoalkylphenones, benzoin ethers, benzoyl oximes, acylphosphine oxides and bisacylphosphine oxides or mixtures of such initiators. A commercial example of such a photoinitiator is DAROCURE® 4265, which is available from Ciba Chemicals, Inc. Non-limiting examples of abstraction-type photoinitiators include benzophenone, Michler's ketone, thioxanthone, anthraquinone, camphorquinone, fluorone, ketocoumarin or mixtures of such initiators.

Another non-limiting example of a photoinitiator that can be present in the at least partial coating according to various non-limiting embodiments disclosed herein is a visible light photoinitiator. Non-limiting examples of suitable visible light photoinitiators are set forth at column 12, line 11 to column 13, line 21 of U.S. Pat. No. 6,602,603, which is specifically incorporated by reference herein.

Non-limiting examples of thermal initiators include organic peroxy compounds and azobis(organonitrile) compounds. Specific non-limiting examples of organic peroxy compounds that are useful as thermal initiators include peroxymonocarbonate esters, such as tertiarybutylperoxy isopropyl carbonate; peroxydicarbonate esters, such as di(2-ethylhexyl) peroxydicarbonate, di(secondary butyl) peroxydicarbonate and diisopropylperoxydicarbonate; diacyperoxides, such as 2,4-dichlorobenzoyl peroxide, isobutyryl peroxide, decanoyl peroxide, lauroyl peroxide, propionyl peroxide, acetyl peroxide, benzoyl peroxide and p-chlorobenzoyl peroxide; peroxyesters such as t-butylperoxy pivalate, t-butylperoxy octylate and t-butylperoxyisobutyrate; methylethylketone peroxide, and acetylcyclohexane sulfonyl peroxide. In one non-limiting embodiment the thermal initiators used are those that do not discolor the resulting polymerizate. Non-limiting examples of azobis(organonitrile) compounds that can be used as thermal initiators include azobis(isobutyronitrile), azobis(2,4-dimethylvaleronitrile) or a mixture thereof.

Non-limiting examples of polymerization inhibitors include: nitrobenzene, 1,3,5,-trinitrobenzene, p-benzoquinone, chloranil, DPPH, $FeCl_3$, $CuCl_2$, oxygen, sulfur, aniline, phenol, p-dihydroxybenzene, 1,2,3-trihydroxybenzene, and 2,4,6-trimethylphenol.

Non-limiting examples of solvents that can be present in the at least partial coating according to various non-limiting embodiments disclosed herein include those that will dissolve solid components of the coating, that are compatible with the coating and the elements and substrates, and/or can ensure uniform coverage of the exterior surface(s) to which the coating is applied. Potential solvents include, but are not limited to, the following: propylene glycol monomethyl ether acetate and their derivates (sold as DOWANOL® industrial solvents), acetone, amyl propionate, anisole, benzene, butyl acetate, cyclohexane, dialkyl ethers of ethylene glycol, e.g., diethylene glycol dimethyl ether and their derivates (sold as CELLOSOLVE® industrial solvents), diethylene glycol dibenzoate, dimethyl sulfoxide, dimethyl formamide, dimethoxybenzene, ethyl acetate, isopropyl alcohol, methyl cyclohexanone, cyclopentanone, methyl ethyl ketone, methyl isobutyl ketone, methyl propionate, propylene carbonate, tetrahydrofuran, toluene, xylene, 2-methoxyethyl ether, 3-propylene glycol methyl ether, and mixtures thereof.

In another non-limiting embodiment, the at least partial coating having the first state and the second state can further comprise at least one conventional dichroic compound. Non-limiting examples of suitable conventional dichroic compounds include azomethines, indigoids, thioindigoids, merocyanines, indans, quinophthalonic dyes, perylenes, phthaloperines, triphenodioxazines, indoloquinoxalines, imidazo-triazines, tetrazines, azo and (poly)azo dyes, benzoquinones, naphthoquinones, anthroquinone and (poly)anthroquinones, anthropyrimidinones, iodine and iodates. In another non-limiting embodiment, the dichroic material can be a polymerizable dichroic compound. That is, according to this non-limiting embodiment, the dichroic material can comprise at least one group that is capable of being polymerized (i.e., a "polymerizable group"). For example, although not limiting herein, in one non-limiting embodiment the at least one dichroic compound can have at least one alkoxy, polyalkoxy, alkyl, or polyalkyl substituent terminated with at least one polymerizable group.

Still further, the at least partial coating having the first state and the second state adapted can comprise at least one conventional photochromic compound. As used herein, the term "conventional photochromic compound" includes both thermally reversible and non-thermally reversible (or photo-reversible) photochromic compounds. Generally, although not limiting herein, when two or more conventional photochromic materials are used in combination with each other or with a photochromic-dichroic compound, the various materials can be chosen to complement one another to produce a desired color or hue. For example, mixtures of photochromic compounds can be used according to certain non-limiting embodiments disclosed herein to attain certain activated colors, such as a near neutral gray or near neutral brown. See, for example, U.S. Pat. No. 5,645,767, column 12, line 66 to column 13, line 19, the disclosure of which is specifically incorporated by reference herein, which describes the parameters that define neutral gray and brown colors.

The optical elements according to various non-limiting embodiments disclosed herein can further comprise at least one additional at least partial coating that can facilitate bonding, adhering, or wetting of any of the various coatings connected to the substrate of the optical element. For example, according to one non-limiting embodiment, the optical element can comprise an at least partial primer coating between the at least partial coating having the first state and the second state and a portion of the substrate. Further, in some non-limiting embodiments disclosed herein, the primer coating can serve as a barrier coating to prevent interaction of the coating ingredients with the element or substrate surface and vice versa.

Non-limiting examples of primer coatings that can be used in conjunction with various non-limiting embodiments disclosed herein include coatings comprising coupling agents, at least partial hydrolysates of coupling agents, and mixtures thereof. As used herein "coupling agent" means a material having at least one group capable of reacting, binding and/or associating with a group on at least one surface. In one non-limiting embodiment, a coupling agent can serve as a molecular bridge at the interface of at least two surfaces that can be similar or dissimilar surfaces. Coupling agents, in another non-limiting embodiment, can be monomers, oligomers, pre-polymers and/or polymers. Such materials include, but are not limited to, organo-metallics such as silanes, titanates, zirconates, aluminates, zirconium aluminates, hydrolysates thereof and mixtures thereof. As used herein the phrase "at least partial hydrolysates of coupling agents" means that at least some to all of the hydrolyzable groups on the coupling agent are hydrolyzed. In addition to coupling agents and/or hydrolysates of coupling agents, the primer coatings can comprise other adhesion enhancing ingredients. For example, although not limiting herein, the primer coating can further comprise an adhesion-enhancing amount of an epoxy-containing material. Adhesion-enhancing amounts of an epoxy-containing materials when added to the coupling agent containing coating composition can improve the adhesion of a subsequently applied coating as compared to a coupling agent containing coating composition that is essentially free of the epoxy-containing material. Other non-limiting examples of primer coatings that are suitable for use in conjunction with the various non-limiting embodiments disclosed herein include those described U.S. Pat. Nos. 6,602,603 and 6,150,430, which are hereby specifically incorporated by reference.

The optical elements according to various non-limiting embodiments disclosed herein can further comprise at least one additional at least partial coating chosen from conventional photochromic coatings, anti-reflective coatings, linearly polarizing coatings, circularly polarizing coatings, elliptically polarizing coatings, transitional coatings, primer coatings (such as those discussed above), and protective coatings connected to at least a portion of the substrate. For example, although not limiting herein, the at least one additional at least partial coating can be over at least a portion of the at least partial coating having the first state and the second state, i.e., as an overcoating; or under at least a portion of the at least partial coating, i.e., as an undercoating. Additionally or alternatively, the at least partial coating having the first state and the second state can be connected at least a portion of a first surface of the substrate and the at least one additional at least partial coating can be connected to at least a portion of a second surface of the substrate, wherein the first surface is opposite the second surface.

Non-limiting examples of conventional photochromic coatings include coatings comprising any of the conventional photochromic compounds that are discussed in detail below. For example, although not limiting herein, the photochromic coatings can be photochromic polyurethane coatings, such as those described in U.S. Pat. No. 6,187,444; photochromic aminoplast resin coatings, such as those described in U.S. Pat. Nos. 4,756,973, 6,432,544 and 6,506,488; photochromic polysilane coatings, such as those described in U.S. Pat. No. 4,556,605; photochromic poly(meth)acrylate coatings, such as those described in U.S. Pat. Nos. 6,602,603, 6,150,430 and 6,025,026, and WIPO Publication WO 01/02449; polyanhydride photochromic coatings, such as those described in U.S. Pat. No. 6,436,525; photochromic polyacrylamide coatings such as those described in U.S. Pat. No. 6,060,001; photochromic epoxy resin coatings, such as those described in U.S. Pat. Nos. 4,756,973 and 6,268,055; and photochromic poly (urea-urethane) coatings, such as those described in U.S. Pat. No. 6,531,076. The specifications of the aforementioned U.S. Patents and international publications are hereby specifically incorporated by reference herein.

Non-limiting examples of linearly polarizing coatings include, but are not limited to, coatings comprising conventional dichroic compounds such as, but not limited to, those discussed above.

As used herein the term "transitional coating" means a coating that aids in creating a gradient in properties between two coatings. For example, although not limiting herein, a transitional coating can aid in creating a gradient in hardness between a relatively hard coating and a relatively soft coating. Non-limiting examples of transitional coatings include radiation-cured acrylate-based thin films.

Non-limiting examples of protective coatings include abrasion-resistant coatings comprising organo silanes, abrasion-resistant coatings comprising radiation-cured acrylate-based thin films, abrasion-resistant coatings based on inorganic materials such as silica, titania and/or zirconia, organic abrasion-resistant coatings of the type that are ultraviolet light curable, oxygen barrier-coatings, UV-shielding coatings, and combinations thereof. For example, according to one non-limiting embodiment, the protective coating can comprise a first coating of a radiation-cured acrylate-based thin film and a second coating comprising an organo-silane. Non-limiting examples of commercial protective coatings products include SILVUE® 124 and HI-GARD® coatings, available from SDC Coatings, Inc. and PPG Industries, Inc., respectively.

Other non-limiting embodiments disclosed herein provide an optical element comprising a substrate and at least one at least partially aligned photochromic-dichroic compound connected to at least a portion the substrate and having an average absorption ratio greater than 2.3 in an activated state as determined according to the CELL METHOD. Further, according to various non-limiting embodiments disclosed herein, the absorption ratio of the at least partially aligned photochromic-dichroic compound can range from 4 to 20, can further range from 3 to 30, and can still further range from 2.5 to 50 or greater.

As previously discussed, the term "connected to" means in direct contact with an object or indirect contact with an object through one or more other structures, at least one of which is in direct contact with the object. Thus, according to the above-mentioned non-limiting embodiments, the at least one at least partially aligned photochromic-dichroic compound can be connected to the at least a portion of the substrate can be in direct contact with the at least a portion of the substrate, or it can be in contact with one or more other structures or materials that are in direct or indirect contact with the substrate. For example, although not limiting herein, in one non-limiting embodiment, the at least one at least partially aligned photochromic-dichroic compound can be present as part of an at least partial coating or polymeric sheet that is in direct contact with the at least a portion of the substrate. In another non-limiting embodiment, the least one at least partially aligned photochromic-dichroic compound can be present as part of a coating or a sheet that is in direct contact with one or more other at least partial coatings or sheets, at least one of which is in direct contact with the at least a portion of the substrate.

According to still other non-limiting embodiments, the at least one at least partially aligned photochromic-dichroic compound can be contained in an at least partially ordered liquid crystal material that is in direct (or indirect) contact with at least a portion the substrate. Further, according to this non-limiting embodiment, the optical element can comprise two substrates and the at least partially ordered liquid crystal material containing the at least partially aligned photochromic-dichroic compound can be positioned between the two substrates, for example, to form an active or a passive liquid crystal cell.

Non-limiting examples of photochromic-dichroic compounds suitable for used in conjunction with various non-limiting embodiments disclosed herein include:

(1) 3-phenyl-3-(4-(4-(3-piperidin-4-yl-propyl)piperidino) phenyl)-13,13-dimethyl-indeno[2',3':3,4]-naphtho[1,2-b] pyran;

(2) 3-phenyl-3-(4-(4-(3-(1-(2-hydroxyethyl)piperidin-4-yl) propyl)piperidino)phenyl)-13,13-dimethyl-indeno[2',3':3, 4]naphtho[1,2-b]pyran;

(3) 3-phenyl-3-(4-(4-(4-butyl-phenylcarbamoyl)-piperidin-1-yl)phenyl)-13,13-dimethyl-6-methoxy-7-(4-phenyl-piperazin-1-yl)indeno[2',3':3,4]naphtho[1,2-b]pyran;

(4) 3-phenyl-3-(4-([1,4']bipiperidinyl-1'-yl)phenyl)-13,13-dimethyl-6-methoxy-7-([1,4]bipiperidinyl-1'-yl)indeno [2',3':3,4]naphtho[1,2-b]pyran;

(5) 3-phenyl-3-(4-(4-phenyl-piperazin-1-yl)phenyl)-13,13-dimethyl-6-methoxy-7-(4-(4-hexylbenzoyloxy)-piperidin-1-yl)indeno[2',3':3,4]naphtho[1,2-b]pyran;

(6) 3-phenyl-3-(4-(4-phenyl-piperazin-1-yl)phenyl)-13,13-dimethyl-6-methoxy-7-(4-(4'-octyloxy-biphenyl-4-carbonyloxy)-piperidin-1-yl)indeno[2',3':3,4]naphtho[1,2-b] pyran;

(7) 3-phenyl-3-(4-(4-phenyl-piperazin-1-yl)phenyl)-13,13-dimethyl-6-methoxy-7-{4-[17-(1,5-dimethyl-hexyl)-10, 13-dimethyl-2,3,4,7,8,9,10,11,12,13,14,15,16,17-tetradecahydro-1H-cyclopenta[a]phenanthren-3-yloxycarbonyloxy]-piperidin-1-yl}-indeno[2',3':3,4] naphtho[1,2-b]pyran;

(8) 3-phenyl-3-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-phenyl)-13,13-dimethyl-6-methoxy-7-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-)indeno[2',3':3,4]naphtho[1,2-b]pyran;

(9) 3-phenyl-3-(4-(4-phenylpiperazin-1-yl)phenyl)-13,13-dimethyl-6-methoxy-7-(4-(4-(4'-octyloxy-biphenyl-4-carbonyloxy)phenyl)piperazin-1-yl)indeno[2',3':3,4]naphtho[1,2-b]pyran;

(10) 3-phenyl-3-(4-(4-phenyl-piperazin-1-yl)phenyl)-13,13-dimethyl-6-methoxy-7-(4-(4-(4-hexyloxyphenylcarbonyloxy)phenyl)piperazin-1-yl)indeno[2',3':3,4]naphtho[1,2-b]pyran;

(11) 3-phenyl-3-(4-(4-phenyl-piperazin-1-yl)phenyl)-13,13-dimethyl-6-methoxy-7-(4-(4-(4-(2-fluorobenzoyloxy)benzoyloxy)phenyl)piperazin-1-yl)indeno[2',3':3,4]naphtho[1,2-b]pyran;

(12) 3-phenyl-3-(4-(pyrrolidin-1-yl)phenyl)-13-hydroxy-13-ethyl-6-methoxy-7-(4-(4-(4-hexylbenzoyloxy)phenyl)piperazin-1-yl)indeno[2',3':3,4]naphtho[1,2-b]pyran;

(13) 3-phenyl-3-(4-(pyrrolidin-1-yl)phenyl)-13,13-dimethyl-6-methoxy-7-(4-(4-hexylbenzoyloxy)benzoyloxy)-indeno[2',3':3,4]naphtho[1,2-b]pyran;

(14) 3-phenyl-3-(4-(pyrrolidin-1-yl)phenyl)-13,13-dimethyl-6-methoxy-7-(4-(4-(4-hexylbenzoyloxy)benzoyloxy)benzoyloxy)indeno[2',3':3,4]naphtho[1,2-b]pyran;

(15) 3-phenyl-3-(4-(4-methoxyphenyl)-piperazin-1-yl))phenyl)-13,13-dimethyl-6-methoxy-7-(4-(4-(3-phenylprop-2-ynoyloxy)phenyl)piperazin-1-yl)-indeno[2',3':3,4]naphtho[1,2-b]pyran;

(16) 3-(4-methoxyphenyl)-3-(4-(4-methoxyphenyl)piperazin-1-yl)phenyl)-13-ethyl-13-hydroxy-6-methoxy-7-(4-(4-(4-hexylbenzoyloxy)phenyl)piperazin-1-yl)indeno[2',3':3,4]naphtho[1,2-b]pyran;

(17) 3-phenyl-3-{4-(pyrrolidin-1-yl)phenyl}-13-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxy]-13-ethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperadin-1-yl)-indeno[2',3':3,4]naphtho[1,2-b]pyran;

(18) 3-phenyl-3-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-phenyl)-13-ethyl-13-hydroxy-6-methoxy-7-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-)indeno[2',3':3,4]naphtho[1,2-b]pyran;

(19) 3-phenyl-3-{4-(pyrrolidin-1-yl)phenyl)-13,13-dimethyl-6-methoxy-7-(4-(4-(4-(3-phenyl-3-{4-(pyrrolidin-1-yl)phenyl}-13,13-dimethyl-6-methoxy-indeno[2',3':3,4]naphtho[1,2-b]pyran-7-yl)-piperadin-1-yl)oxycarbonyl)phenyl)phenyl)carbonyloxy)-indeno[2',3':3,4]naphtho[1,2-b]pyran;

(20) 3-{4-[4-(4-methoxy-phenyl)-piperazin-1-yl]-phenyl}-3-phenyl-7-methoxycarbonyl-3H-naphtho[2,1-b]pyran;

(21) 3-{4-[4-(4-methoxy-phenyl)-piperazin-1-yl]-phenyl}-3-phenyl-7-hydroxycarbonyl-3H-naphtho[2,1-b]pyran;

(22) 3-{4-[4-(4-methoxy-phenyl)-piperazin-1-yl]-phenyl}-3-phenyl-7-(4-phenyl-(phen-1-oxy)carbonyl)-3H-naphtho[2,1-b]pyran;

(23) 3-{4-[4-(4-methoxy-phenyl)-piperazin-1-yl]-phenyl}-3-phenyl-7-(N-(4-((4-dimethylamino)phenyl)diazenyl)phenyl)carbamoyl-3H-naphtho[2,1-b]pyran;

(24) 2-phenyl-2-{4-[4-(4-methoxy-phenyl)-piperazin-1-yl]-phenyl}-benzofuro[3',2':7,8]benzo[b]pyran;

(25) 2-phenyl-2-{4-[4-(4-methoxy-phenyl)-piperazin-1-yl]-phenyl}-benzothieno[3',2':7,8]benzo[b]pyran;

(26) 7-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}-2-phenyl-2-(4-pyrrolidin-1-yl-phenyl)-6-methoxycarbonyl-2H-benzo[b]pyran;

(27) 2-phenyl-2-{4-[4-(4-methoxy-phenyl)-piperazin-1-yl]-phenyl}-9-hydroxy-8-methoxycarbonyl-2H-naphtho[1,2-b]pyran;

(28) 2-phenyl-2-{4-[4-(4-methoxy-phenyl)-piperazin-1-yl]-phenyl}-9-hydroxy-8-(N-(4-butyl-phenyl))carbamoyl-2H-naphtho[1,2-b]pyran;

(29) 2-phenyl-2-{4-[4-(4-methoxy-phenyl)-piperazin-1-yl]-phenyl}-9-hydroxy-8-(N-(4-phenyl)phenyl) carbamoyl-2H-naphtho[1,2-b]pyran;

(30) 1,3,3-trimethyl-6'-(4-ethoxycarbonyl)-piperidin-1-yl)-spiro[indoline-2,3'-3H-naphtho[2,1-b][1,4]oxazine];

(31) 1,3,3-trimethyl-6'-(4-[N-(4-butylphenyl)carbamoyl]-piperidin-1-yl)-spiro[indoline-2,3'-3H-naphtho[2,1-b][1,4]oxazine];

(32) 1,3,3-trimethyl-6'-(4-(4-methoxyphenyl)piperazin-1-yl)-spiro[indoline-2,3'-3H-naphtho[2,1-b][1,4]oxazine];

(33) 1,3,3-trimethyl-6'-(4-(4-hydroxyphenyl)piperazin-1-yl)-spiro[indoline-2,3'-3H-naphtho[2,1-b][1,4]oxazine];

(34) 1,3,3,5,6-pentamethyl-7'-(4-(4-methoxyphenyl)piperazin-1-yl)-spiro[indoline-2,3'-3H-naphtho[2,1-b][1,4]oxazine];

(35) 1,3-diethyl-3-methyl-5-methoxy-6'-(4-(4'-Hexyloxy-biphenyl-4-carbonyloxy)-piperidin-1-yl)-spiro[indoline-2,3'-3H-naphtho[2,1-b][1,4]oxazine];

(36) 1,3-diethyl-3-methyl-5-[4-(4-pentadecafluoroheptyloxy-phenylcarbamoyl)-benzyloxy]-6'-(4-(4'-hexyloxy-biphenyl-4-carbonyloxy)-piperidin-1-yl)-spiro[indoline-2,3'-3H-naphtho[2,1-b][1,4]oxazine];

(37) 2-phenyl-2-{4-[4-(4-methoxy-phenyl)-piperazin-1-yl]-phenyl}-5-carbomethoxy-8-(N-(4-phenyl)phenyl) carbamoyl-2H-naphtho[1,2-b]pyran;

(38) 2-phenyl-2-{4-[4-(4-methoxy-phenyl)-piperazin-1-yl]-phenyl}-5-carbomethoxy-8-(N-(4-phenyl)phenyl) carbamoyl-2H-fluoantheno[1,2-b]pyran;

(39) 2-phenyl-2-{4-[4-(4-methoxy-phenyl)-piperazin-1-yl]-phenyl}-5-carbomethoxy-11-(4-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}phenyl)-2H-fluoantheno[1,2-b]pyran;

(40) 1-(4-carboxybutyl)-6-(4-(4-propylphenyl)carbonyloxy)phenyl)-3,3-dimethyl-6'-(4-ethoxycarbonyl)-piperidin-1-yl)-spiro[(1,2-dihydro-9H-dioxolano[4',5':6,7]indoline-2,3'-3H-naphtho[2,1-b][1,4]oxazine];

(41) 1-(4-carboxybutyl)-6-(4-(4-propylphenyl)carbonyloxy)phenyl)-3,3-dimethyl-7'-(4-ethoxycarbonyl)-piperidin-1-yl)-spiro[(1,2-dihydro-9H-dioxolano[4',5':6,7]indoline-2,3'-3H-naphtho[1,2-b][1,4]oxazine];

(42) 1,3-diethyl-3-methyl-5-(4-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}phenyl)-6'-(4-(4'-hexyloxy-biphenyl-4-carbonyloxy)-piperidin-1-yl)-spiro[indoline-2,3'-3H-naphtho[2,1-b][1,4]oxazine];

(43) 1-butyl-3-ethyl-3-methyl-5-methoxy-7'-(4-(4'-Hexyloxy-biphenyl-4-carbonyloxy)-piperidin-1-yl)-spiro[indoline-2,3'-3H-naphtho[1,2-b][1,4]oxazine];

(44) 2-phenyl-2-{4-[4-(4-methoxy-phenyl)-piperazin-1-yl]phenyl}-5-methoxycarbonyl-6-methyl-2H-9-(4-(4-propylphenyl)carbonyloxy)phenyl)(1,2-dihydro-9H-dioxolano[4',5':6,7]naphtho[1,2-b]pyran;

(45) 3-(4-methoxyphenyl)-3-(4-(4-methoxyphenyl)piperazin-1-yl)phenyl)-13-ethyl-13-hydroxy-6-methoxy-7-(4-(4-propylphenyl)carbonyloxy)phenyl)-[1,2-dihydro-9H-dioxolano[4'',5'':6,7][indeno[2',3':3,4]]naphtho[1,2-b]pyran;

(46) 3-phenyl-3-(4-(4-methoxyphenyl)piperazin-1-yl)phenyl)-13-ethyl-13-hydroxy-6-methoxy-7-(4-(4-hexylphenyl)carbonyloxy)phenyl)-[1,2-dihydro-9H-dioxolano[4'',5'':5,6][indeno[2',3':3,4]]naphtho[1,2-b]pyran;

(47) 4-(4-((4-cyclohexylidene-1-ethyl-2,5-dioxopyrrolin-3-ylidene)ethyl)-2-thienyl)phenyl-(4-propyl)benzoate;

(48) 4-(4-((4-adamantan-2-ylidene-1-(4-(4-hexylphenyl)carbonyloxy)phenyl)-2,5-dioxopyrrolin-3-ylidene)ethyl)-2-thienyl)phenyl-(4-propyl)benzoate;

(49) 4-(4-((4-adamantan-2-ylidene-2,5-dioxo-1-(4-(4-(4-propylphenyl)piperazinyl)phenyl)pyrrolin-3-ylidene)ethyl)-2-thienyl)phenyl(4-propyl)benzoate;

(50) 4-(4-((4-adamantan-2-ylidene-2,5-dioxo-1-(4-(4-(4-propylphenyl)piperazinyl)phenyl)pyrrolin-3-ylidene)ethyl)-1-methylpyrrol-2-yl)phenyl(4-propyl)benzoate;

(51) 4-(4-((4-adamantan-2-ylidene-2,5-dioxo-1-(4-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}phenyl)pyrrolin-3-ylidene)ethyl)-1-methylpyrrol-2-yl)phenyl(4-propyl)benzoate;

(52) 4-(4-methyl-5,7-dioxo-6-(4-(4-(4-propylphenyl)piperazinyl)phenyl)spiro[8,7a-dihydrothiapheno[4,5-f]isoindole-8,2'-adamentane]-2-yl)phenyl(4-propyl)phenyl benzoate;

(53) N-(4-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}phenyl-6,7-dihydro-4-methyl-2-phenylspiro(5,6-benzo[b]thiophenedicarboxyimide-7,2-tricyclo[3.3.1.1]decane);

(54) N-cyanomethyl-6,7-dihydro-2-(4-(4-(4-propylphenyl)piperazinyl)phenyl)$_4$-methylspiro(5,6-benzo[b]thiophenedicarboxyimide-7,2-tricyclo[3.3.1.1]decane);

(55) N-phenylethyl-6,7-dihydro-2-(4-(4-(4-hexylbenzoyloxy)phenyl)piperazin-1-yl)phenyl-4-methylspiro(5,6-benzo[b]thiophenedicarboxyimide-7,2-tricyclo[3.3.1.1]decane);

(56) N-phenylethyl-6,7-dihydro-2-(4-(4-(4-hexylbenzoyloxy)phenyl)piperazin-1-yl)phenyl-4-cyclopropyl spiro(5,6-benzo[b]thiophenedicarboxyimide-7,2-tricyclo[3.3.1.1]decane);

(57) N-phenylethyl-6,7-dihydro-2-(4-(4-(4-hexylbenzoyloxy)phenyl)piperazin-1-yl)phenyl-4-cyclopropyl spiro(5,6-benzo[b]furodicarboxyimide-7,2-tricyclo[3.3.1.1]decane);

(58) N-cyanomethyl-6,7-dihydro-4-(4-(4-(4-hexylbenzoyloxy)phenyl)piperazin-1-yl)phenyl-2-phenylspiro(5,6-benzo[b]thiophenedicarboxyimide-7,2-tricyclo[3.3.1.1]decane);

(59) N-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyl-6,7-dihydro-2-(4-methoxyphenyl)phenyl-4-methylspiro(5,6-benzo[b]thiophenedicarboxyimide-7,2-tricyclo[3.3.1.1]decane);

(60) N-cyanomethyl-2-(4-(6-(4-butylphenyl)carbonyloxy-(4,8-dioxabicyclo[3.3.0]oct-2-yl))oxycarbonyl)phenyl-6,7-dihydro-4-cyclopropylspiro(5,6-benzo[b]thiophenedicarboxyimide-7,2-tricyclo[3.3.1.1]decane);

(61) 6,7-dihydro-N-methoxycarbonylmethyl-4-(4-(6-(4-butylphenyl)carbonyloxy-(4,8-dioxabicyclo[3.3.0]oct-2-yl))oxycarbonyl)phenyl-2-phenylspiro(5,6-benzo[b]thiophenedicarboxyimide-7,2-tricyclo[3.3.1.1]decane); and

(62) 3-phenyl-3-(4-pyrrolidinylphenyl)-13,13-dimethyl-6-methoxy-7-(4-(4-(4-(4-(6-(4-(4-(4-nonylphenylcabonyloxy)phenyl)oxycarbonyl)phenoxy)hexyloxy)phenyl)piperazin-1-yl)indeno[2',3':3,4]naphtho[1,2-b]pyran.

More generally, such photochromic-dichroic compounds comprise: (a) at least one photochromic group (PC) chosen from pyrans, oxazines, and fulgides; and (b) at least one lengthening agent attached to the at least one photochromic group, wherein the lengthening agent (L) is represented by the following Formula I (which is described in detail below):

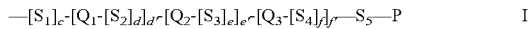

$$—[S_1]_c-[Q_1-[S_2]_d]_{d'}-[Q_2-[S_3]_e]_{e'}-[Q_3-[S_4]_f]_{f'}—S_5—P \quad \text{I}$$

As used herein, the term "attached" means directly bonded to or indirectly bonded to through another group. Thus, for example, according to various non-limiting embodiments disclosed herein, L can be directly bonded to PC as a substituent on PC, or L can be a substituent on another group (such as a group represented by $R^1$, which is discussed below) that is directly bonded to PC (i.e., L is indirectly bonded to PC). Although not limiting herein, according to various non-limiting embodiments, L can be attached to PC so as to extend or lengthen PC in an activated state such that the absorption ratio of the extended PC (i.e., the photochromic compound) is enhanced as compared to PC alone. Although not limiting herein, according to various non-limiting embodiments, the location of attachment of L on PC can be chosen such that L lengthens PC in at least one of a direction parallel to and a direction perpendicular to a theoretical transitional dipole moment of the activated form of PC. As used herein the term "theoretical transitional dipole moment" refers to transient dipolar polarization created by interaction of electromagnetic radiation with the molecule. See, for example, *IUPAC Compendium of Chemical Technology*, 2$^{nd}$ Ed., International Union of Pure and Applied Chemistry (1997).

With reference to Formula I above, each $Q_1$, $Q_2$, and $Q_3$ can be independently chosen for each occurrence from: a divalent group chosen from an unsubstituted or a substituted aromatic group, an unsubstituted or a substituted alicyclic group, an unsubstituted or a substituted heterocyclic group, and mixtures thereof, wherein substituents are chosen from: a group represented by P (as set forth below), aryl, thiol, amide, liquid crystal mesogens, halogen, $C_1$-$C_{18}$ alkoxy, poly($C_1$-$C_{18}$ alkoxy), amino, amino($C_1$-$C_{18}$)alkylene, $C_1$-$C_{18}$alkylamino, di-($C_1$-$C_{18}$)alkylamino, $C_1$-$C_{18}$alkyl, $C_2$-$C_{18}$ alkene, $C_2$-$C_{18}$ alkyne, $C_1$-$C_{18}$ alkyl($C_1$-$C_{18}$)alkoxy, $C_1$-$C_{18}$ alkoxycarbonyl, $C_1$-$C_{18}$ alkylcarbonyl, $C_1$-$C_{18}$ alkyl carbonate, aryl carbonate, $C_1$-$C_{18}$ acetyl, $C_3$-$C_{10}$ cycloalkyl, $C_3$-$C_{10}$ cycloalkoxy, isocyanato, amido, cyano, nitro, a straight-chain or branched $C_1$-$C_{18}$ alkyl group that is mono-substituted with cyano, halo, or $C_1$-$C_{18}$ alkoxy, or poly-substituted with halo, and a group represented by one of the following formulae: $-M(T)_{(t-1)}$ and $-M(OT)_{(t-1)}$ wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M. As used herein, the prefix "poly" means at least two.

As discussed above, $Q_1$, $Q_2$, and $Q_3$ can be independently chosen for each occurrence from a divalent group, such as an unsubstituted or a substituted aromatic group, unsubstituted or substituted heterocyclic group, and an unsubstituted or substituted alicylic group. Non-limiting examples of useful aromatic groups include: benzo, naphtho, phenanthro, biphenyl, tetrahydro naphtho, terphenyl, and anthraceno.

As used herein the term "heterocyclic group" means a compound having a ring of atoms, wherein at least one atom forming the ring is different than the other atoms forming the ring. Further, as used herein, the term heterocyclic group specifically excludes fused heterocyclic groups. Non-limiting examples of suitable heterocyclic groups from which $Q_1$, $Q_2$, and $Q_3$ can be chosen include: isosorbitol, dibenzofuro, dibenzothieno, benzofuro, benzothieno, thieno, furo, dioxino, carbazolo, anthranilyl, azepinyl, benzoxazolyl, diazepinyl, dioazlyl, imidazolidinyl, imidazolyl, imidazolinyl, indazolyl, indoleninyl, indolinyl, indolizinyl, indolyl, indoxazinyl, isobenzazolyl, isoindolyl, isooxazolyl, isooxazyl, isopyrroyl, isoquinolyl, isothiazolyl, morpholino, morpholinyl, oxadiazolyl, oxathiazolyl, oxathiazyl, oxathiolyl, oxatriazolyl, oxazolyl, piperazinyl, piperazyl, piperidyl, purinyl, pyranopyrrolyl, pyrazinyl, pyrazolidinyl, pyrazolinyl, pyrazolyl, pyrazyl, pyridazinyl, pyridazyl, pyridyl, pyrimidinyl, pyrimidyl, pyridenyl, pyrrolidinyl, pyrrolinyl, pyrroyl, quinolizinyl, quinuclidinyl, quinolyl, thiazolyl, triazolyl, triazyl, N-arylpiperazino, aziridino, arylpiperidino, thiomorpholino, tetrahydroquinolino, tetrahydroisoquinolino, pyrryl, unsubstituted, mono- or di-substituted $C_4$-$C_{18}$ spirobicyclic amines, and unsubstituted, mono- or di-substituted $C_4$-$C_{18}$ spirotricyclic amines.

As discussed above, $Q_1$, $Q_2$, and $Q_3$ can be chosen from mono- or di-substituted $C_4$-$C_{18}$ spirobicyclic amine and $C_4$-$C_{18}$ spirotricyclic amine. Non-limiting examples of suitable substituents include aryl, $C_1$-$C_6$ alkyl, $C_1$-$C_6$ alkoxy or phenyl ($C_1$-$C_6$)alkyl. Specific non-limiting examples of mono- or di-substituted spirobicyclic amines include: 2-azabicyclo[2.2.1]hept-2-yl; 3-azabicyclo[3.2.1]oct-3-yl; 2-azabicyclo[2.2.2]oct-2-yl; and 6-azabicyclo[3.2.2]nonan-6-yl. Specific non-limiting examples of mono- or di-substituted tricyclic amines include: 2-azatricyclo[3.3.1.1(3,7)]decan-2-yl; 4-benzyl-2-azatricyclo[3.3.1.1 (3,7)]decan-2-yl; 4-methoxy-6-methyl-2-azatricyclo[3.3.1.1(3,7)]decan-2-yl; 4-azatricyclo[4.3.1.1(3,8)]undecan-4-yl; and 7-methyl-4-azatricyclo[4.3.1.1(3,8)]undecan-4-yl. Examples of alicyclic groups from which $Q_1$, $Q_2$, and $Q_3$ can be chosen include, without limitation, cyclohexyl, cyclopropyl, norbornenyl, decalinyl, adamantanyl, bicycloctane, per-hydrofluorene, and cubanyl.

With continued reference to Formula I, and each $S_1$, $S_2$, $S_3$, $S_4$, and $S_5$ is independently chosen for each occurrence from a spacer unit chosen from:
(1) —$(CH_2)_g$—, —$(CF_2)_h$—, —$Si(CH_2)_g$—, —$Si[(CH_3)_2]O)_h$—, wherein g is independently chosen for each occurrence from 1 to 20; h is chosen from 1 to 16;
(2) —N(Z)—, —C(Z)=C(Z)—, —C(Z)=N—, —C(Z')—C(Z')-, wherein Z is independently chosen for each occurrence from hydrogen, $C_1$-$C_6$ alkyl, cycloalkyl and aryl, and Z' is independently chosen for each occurrence from $C_1$-$C_6$ alkyl, cycloalkyl and aryl; and
(3) —O—, —C(O)—, —C≡C—, —N=N—, —S—, —S(O)—, —S(O)(O)—, straight-chain or branched $C_1$-$C_{24}$ alkylene residue, said $C_1$-$C_{24}$ alkylene residue being unsubstituted, mono-substituted by cyano or halo, or poly-substituted by halo;

provided that when two spacer units comprising heteroatoms are linked together the spacer units are linked so that heteroatoms are not directly linked to each other and when $S_1$ and $S_5$ are linked to PC and P, respectively, they are linked so that two heteroatoms are not directly linked to each other. As used herein the term "heteroatom" means atoms other than carbon or hydrogen.

Further, in Formula I, according to various non-limiting embodiments, c, d, e, and f each can be independently chosen from an integer ranging from 1 to 20, inclusive; and d', e' and f' each can be independently chosen from 0, 1, 2, 3, and 4, provided that the sum of d'+e'+f' is at least 1. According to other non-limiting embodiments, c, d, e, and f each can be independently chosen from an integer ranging from 0 to 20, inclusive; and d', e' and f' each can be independently chosen from 0, 1, 2, 3, and 4, provided that the sum of d'+e'+f' is at least 2. According to still other non-limiting embodiments, c, d, e, and f each can be independently chosen from an integer ranging from 0 to 20, inclusive; and d', e' and f' each can be independently chosen from 0, 1, 2, 3, and 4, provided that the sum of d'+e'+f' is at least 3. According to still other non-limiting embodiments, c, d, e, and f each can be independently chosen from an integer ranging from 0 to 20, inclusive; and d', e' and f' each can be independently chosen from 0, 1, 2, 3, and 4, provided that the sum of d'+e'+f' is at least 1.

Further, in Formula I, P can be chosen from: aziridinyl, hydrogen, hydroxy, aryl, alkyl, alkoxy, amino, alkylamino, alkylalkoxy, alkoxyalkoxy, nitro, polyalkyl ether, ($C_1$-$C_6$) alkyl($C_1$-$C_6$)alkoxy($C_1$-$C_6$)alkyl, polyethyleneoxy, polypropyleneoxy, ethylene, acrylate, methacrylate, 2-chloroacrylate, 2-phenylacrylate, acryloylphenylene, acrylamide, methacrylamide, 2-chloroacrylamide, 2-phenylacrylamide, epoxy, isocyanate, thiol, thioisocyanate, itaconic acid ester, vinyl ether, vinyl ester, a styrene derivative, siloxane, main-chain and side-chain liquid crystal polymers, a liquid crystal mesogen, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, and substituted and unsubstituted chiral and non-chiral monovalent or divalent groups chosen from steroid radicals, terpenoid radicals, alkaloid radicals and mixtures thereof, wherein the substituents are independently chosen from an alkyl, an alkoxy, amino, cycloalkyl, alkylalkoxy, a fluoroalkyl, a cyanoalkyl, a cyanoalkoxy and mixtures thereof.

Further, although not limiting herein, when P is a polymerizable group, the polymerizable group can be any functional group adapted to participate in a polymerization reaction. Non-limiting examples of polymerization reactions include those described in the definition of "polymerization" in *Hawley's Condensed Chemical Dictionary Thirteenth Edition*, 1997, John Wiley & Sons, pages 901-902, which disclosure is incorporated herein by reference. For example, although not limiting herein, polymerization reactions include: "addition polymerization," in which free radicals are the initiating agents that react with the double bond of a monomer by adding to it on one side at the same time producing a new free electron on the other side; "condensation polymerization," in which two reacting molecules combine to form a larger molecule with elimination of a small molecule, such as a water molecule; and "oxidative coupling polymerization." Further, non-limiting examples of polymerizable groups include hydroxy, acryloxy, methacryloxy, 2-(acryloxy)ethylcarbamyl, 2-(methacryloxy)ethylcarbamyl, isocyanate, aziridine, allylcarbonate, and epoxy, e.g., oxiranylmethyl.

Moreover, P can be chosen from a main-chain or a side-chain liquid crystal polymer and a liquid crystal mesogen. As used herein, the term liquid crystal "mesogen" means rigid rod-like or disc-like liquid crystal molecules. Further, as used herein the term "main-chain liquid crystal polymer" refers to a polymer having liquid crystal mesogens within the backbone (i.e., the main chain) structure of the polymer. As used herein the term "side-chain liquid crystal polymer" refers to a polymer having liquid crystal mesogens attached to the polymer at the side chains. Although not limiting herein, generally, the mesogens are made up of two or more aromatic rings that restrict the movement of a liquid crystal polymer. Examples of suitable rod-like liquid crystal mesogens include without limitation: substituted or unsubstituted aromatic esters, substituted or unsubstituted linear aromatic compounds, and substituted or unsubstituted terphenyls. According to another specific, non-limiting embodiment, P can be chosen from a steroid, for example and without limitation, a cholesterolic compound.

Non-limiting examples of thermally reversible photochromic pyrans from which the photochromic group PC can be chosen include benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference; spiro-9-fluoreno[1,2-b]pyrans; phenanthropyrans; quinopyrans; fluoroanthenopyrans; spiropyrans, e.g., spiro(benzindoline)naphthopyrans, spiro(indoline)benzopyrans, spiro(indoline)naphthopyrans, spiro(indoline)quinopyrans and spiro(indoline)pyrans. More specific examples of naphthopyrans and the complementary organic photochromic substances are described in U.S. Pat. No. 5,658,501, which are hereby specifically incorporated by reference herein. Spiro(indoline) pyrans are also described in the text, *Techniques in Chemistry*, Volume III, "Photochromism", Chapter 3, Glenn H. Brown, Editor, John Wiley and Sons, Inc., New York, 1971, which is hereby incorporated by reference.

Non-limiting examples of photochromic oxazines from which PC can be chosen include benzoxazines, naphthoxazines, and spiro-oxazines, e.g., spiro(indoline)naphthoxazines, spiro(indoline)pyridobenzoxazines, spiro(benzindoline)pyridobenzoxazines, spiro(benzindoline) naphthoxazines, spiro(indoline)benzoxazines, spiro (indoline)fluoranthenoxazine, and spiro(indoline) quinoxazine. Non-limiting examples of photochromic fulgides from which PC can be chosen include: fulgimides, and the 3-furyl and 3-thienyl fulgides and fulgimides, which are disclosed in U.S. Pat. No. 4,931,220 (which are hereby specifically incorporated by reference) and mixtures of any of the aforementioned photochromic materials/compounds.

Further, wherein the photochromic-dichroic compound comprises at least two PCs, the PCs can be linked to one another via linking group substituents on the individual PCs. For example, the PCs can be polymerizable photochromic groups or photochromic groups that are adapted to be compatible with a host material ("compatibilized photochromic group"). Non-limiting examples of polymerizable photochromic groups from which PC can be chosen and that are useful in conjunction with various non-limiting embodiments disclosed herein are disclosed in U.S. Pat. No. 6,113,814, which is hereby specifically incorporated by reference herein. Non-limiting examples of compatiblized photochromic groups from which PC can be chosen and that are useful in conjunction with various non-limiting embodiments disclosed herein are disclosed in U.S. Pat. No. 6,555,028, which is hereby specifically incorporated by reference herein.

Other suitable photochromic groups and complementary photochromic groups are described in U.S. Pat. No. 6,080,338 at column 2, line 21 to column 14, line 43; U.S. Pat. No. 6,136,968 at column 2, line 43 to column 20, line 67; U.S. Pat. No. 6,296,785 at column 2, line 47 to column 31, line 5; U.S. Pat. No. 6,348,604 at column 3, line 26 to column 17, line 15; U.S. Pat. No. 6,353,102 at column 1, line 62 to column 11, line 64; and U.S. Pat. No. 6,630,597 at column 2, line 16 to column 16, line 23; the disclosures of the aforementioned patents are incorporated herein by reference.

In addition to at least one lengthening agent (L), the photochromic compounds can further comprise at least one group represented by $R^1$ that is directly bonded to PC. Although not required, as previously discussed, the at least one lengthening agent (L) can be indirectly bonded to PC through the at least one group represented by $R^1$. That is, L can be a substituent on at least one group $R^1$ that is bonded to PC. According to various non-limiting embodiments disclosed herein, $R^1$ can be independently chosen for each occurrence from:

(i) hydrogen, $C_1$-$C_{12}$ alkyl, $C_2$-$C_{12}$ alkylidene, $C_2$-$C_{12}$ alkylidyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;

(ii) phenyl that is mono-substituted at the para position with at least one substituent chosen from: $C_1$-$C_7$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_4$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material;

(iii) —CH(CN)$_2$ and —CH(COOX$_1$)$_2$, wherein X$_1$ is chosen from at least one of a lengthening agent L represented by Formula I above, H, $C_1$-$C_{12}$ alkyl that is unsubstituted or mono-substituted with phenyl, phenyl ($C_1$-$C_{12}$)alkyl that is mono-substituted with $C_1$-$C_{12}$ alkyl or $C_1$-$C_{12}$ alkoxy, and an aryl group that is unsubstituted, mono- or di-substituted, wherein each aryl substituent is independently chosen from $C_1$-$C_{12}$ alkyl and $C_1$-$C_{12}$ alkoxy;

(iv) —CH(X$_2$)(X$_3$), wherein:
  (A) X$_2$ is chosen from at least one of a lengthening agent L represented by Formula I above, hydrogen, $C_1$-$C_{12}$ alkyl and an aryl group that is unsubstituted, mono- or di-substituted, wherein each aryl substituent is independently chosen from $C_1$-$C_{12}$ alkyl and $C_1$-$C_{12}$ alkoxy; and
  (B) X$_3$ is chosen from at least one of —COOX$_1$, —COX$_1$, —COX$_4$, and —CH$_2$OX$_5$, wherein:
    (1) X$_4$ is chosen from at least one of morpholino, piperidino, amino that is unsubstituted, mono- or di-substituted with $C_1$-$C_{12}$ alkyl, and an unsubstituted, mono or di-substituted group chosen from phenylamino and diphenylamino, wherein each substituent is independently chosen from $C_1$-$C_{12}$ alkyl or $C_1$-$C_{12}$ alkoxy; and
    (2) X$_5$ is chosen from a lengthening agent L represented by Formula I above, hydrogen, —C(O)X$_2$, $C_1$-$C_{12}$ alkyl that is unsubstituted or mono-substituted with ($C_1$-$C_{12}$)alkoxy or phenyl, phenyl($C_1$-$C_{12}$)alkyl that is mono-substituted with ($C_1$-$C_{12}$) alkoxy, and an aryl group that is unsubstituted, mono- or di-substituted, wherein each aryl substituent is independently chosen from $C_1$-$C_{12}$ alkyl and $C_1$-$C_{12}$ alkoxy;

(v) an unsubstituted, mono-, di-, or tri-substituted aryl group, such as phenyl, naphthyl, phenanthryl, or pyrenyl; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl; wherein the substituents are independently chosen for each occurrence from:

(A) a lengthening agent L represented by Formula I above;

(B) —C(O)$X_6$, wherein $X_6$ is chosen from at least one of: a lengthening agent L represented by Formula I above, H, $C_1$-$C_{12}$ alkoxy, phenoxy that is unsubstituted, mono- or di-substituted with $C_1$-$C_{12}$ alkyl or $C_1$-$C_{12}$ alkoxy, an aryl group that is unsubstituted, mono- or di-substituted with $C_1$-$C_{12}$ alkyl or $C_1$-$C_{12}$ alkoxy, an amino group that is unsubstituted, mono- or di-substituted with $C_1$-$C_{12}$ alkyl, and a phenylamino group that is unsubstituted, mono- or di-substituted with $C_1$-$C_{12}$ alkyl or $C_1$-$C_{12}$ alkoxy;

(C) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;

(D) $C_1$-$C_{12}$ alkyl, $C_3$-$C_7$ cycloalkyl, $C_3$-$C_7$ cycloalkyloxy($C_1$-$C_{12}$)alkyl, aryl($C_1$-$C_{12}$)alkyl, aryloxy($C_1$-$C_{12}$)alkyl, mono- or di-($C_1$-$C_{12}$)alkylaryl($C_1$-$C_{12}$) alkyl, mono- or di-($C_1$-$C_{12}$)alkoxyaryl($C_1$-$C_{12}$)alkyl, haloalkyl, and mono($C_1$-$C_{12}$)alkoxy($C_1$-$C_{12}$)alkyl;

(E) $C_1$-$C_{12}$ alkoxy, $C_3$-$C_7$ cycloalkoxy; cycloalkyloxy($C_1$-$C_{12}$)alkoxy; aryl($C_1$-$C_{12}$)alkoxy, aryloxy($C_1$-$C_{12}$)alkoxy, mono- or di-($C_1$-$C_{12}$)alkylaryl($C_1$-$C_{12}$) alkoxy, and mono- or di-($C_1$-$C_{12}$)alkoxyaryl($C_1$-$C_{12}$) alkoxy;

(F) amido, amino, mono- or di-alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;

(G) —O$X_7$ and —N($X_7$)$_2$, wherein $X_7$ is chosen from:
  (1) a lengthening agent L represented by Formula I above, hydrogen, $C_1$-$C_{12}$ alkyl, $C_1$-$C_{12}$ acyl, phenyl ($C_1$-$C_{12}$)alkyl, mono($C_1$-$C_{12}$)alkyl substituted phenyl($C_1$-$C_{12}$)alkyl, mono($C_1$-$C_{12}$)alkoxy substituted phenyl($C_1$-$C_{12}$)alkyl; $C_1$-$C_{12}$ alkoxy($C_1$-$C_{12}$) alkyl; $C_3$-$C_7$ cycloalkyl; mono($C_1$-$C_{12}$)alkyl substituted $C_3$-$C_7$ cycloalkyl, $C_1$-$C_{12}$ haloalkyl, allyl, benzoyl, mono-substituted benzoyl, naphthoyl or mono-substituted naphthoyl, wherein each of said benzoyl and naphthoyl substituents are independently chosen from $C_1$-$C_{12}$ alkyl, and $C_1$-$C_{12}$ alkoxy;
  (2) —CH($X_8$)$X_9$, wherein $X_8$ is chosen from a lengthening agent L represented by Formula I above, H or $C_1$-$C_{12}$ alkyl; and $X_9$ is chosen from a lengthening agent L represented by Formula I above, —CN, —CF$_3$, or —COO$X_{10}$, wherein $X_{10}$ is chosen from a lengthening agent L represented by Formula I above, H or $C_1$-$C_{12}$ alkyl;
  (3) —C(O)$X_6$; and
  (4) tri($C_1$-$C_{12}$)alkylsilyl, tri($C_1$-$C_{12}$)alkoxysilyl, di($C_1$-$C_{12}$)alkyl($C_1$-$C_{12}$ alkoxy)silyl, or di($C_1$-$C_{12}$) alkoxy($C_1$-$C_{12}$ alkyl)silyl;

(H) —S$X_{11}$, wherein $X_{11}$ is chosen from a lengthening agent L represented by Formula I above, $C_1$-$C_{12}$ alkyl, an aryl group that is unsubstituted, or mono- or di-substituted with $C_1$-$C_{12}$ alkyl, $C_1$-$C_{12}$ alkoxy or halogen;

(I) a nitrogen containing ring represented by Formula i:

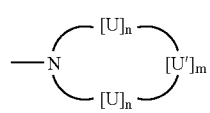

i wherein:
  (1) n is an integer chosen from 0, 1, 2, and 3, provided that if n is 0, U' is U, and each U is independently chosen for each occurrence from —CH$_2$—, —CH($X_{12}$)—, —C($X_{12}$)$_2$—, —CH($X_{13}$)—, —C($X_{13}$)$_2$—, and —C($X_{12}$)($X_{13}$)—, wherein $X_{12}$ is chosen from a lengthening agent L represented by Formula I above and $C_1$-$C_{12}$ alkyl, and $X_{13}$ is chosen from a lengthening agent L represented by Formula I above, phenyl and naphthyl, and
  (2) U' is chosen from U, —O—, —S—, —S(O)—, —NH—, —N($X_{12}$)— or —N($X_{13}$)—, and m is an integer chosen from 1, 2, and 3; and (J) a group represented by one of Formula ii or iii:

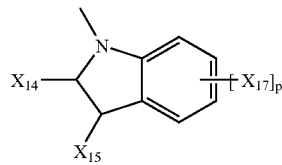

ii

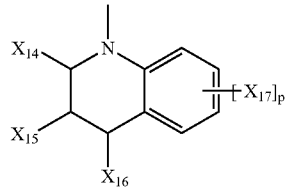

iii wherein $X_{14}$, $X_{15}$, and $X_{16}$ are independently chosen for each occurrence from a lengthening agent L represented by Formula I above, $C_1$-$C_{12}$ alkyl, phenyl and naphthyl, or $X_{14}$ and $X_{15}$ together form a ring of 5 to 8 carbon atoms; p is an integer chosen from 0, 1, or 2, and $X_{17}$ is independently chosen for each occurrence from a lengthening agent L represented by Formula I above, $C_1$-$C_{12}$ alkyl, $C_1$-$C_{12}$ alkoxy and halogen;

(vi) an unsubstituted or mono-substituted group chosen from pyrazolyl, imidazolyl, pyrazolinyl, imidazolinyl, pyrrolidinyl, phenothiazinyl, phenoxazinyl, phenazinyl and acridinyl, wherein each substituent is independently chosen from a lengthening agent L represented by Formula I above, $C_1$-$C_{12}$ alkyl, $C_1$-$C_{12}$ alkoxy, phenyl, hydroxy, amino and halogen;

(vii) a group represented by one of Formula iv or v:

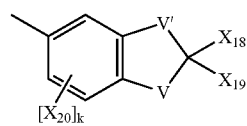

iv

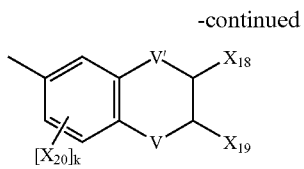

v

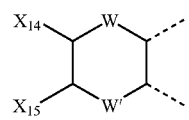

viii

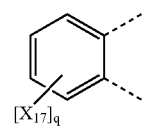

ix wherein
 (A) V' is independently chosen in each formula from —O—, —CH—, $C_1$-$C_6$ alkylene, and $C_3$-$C_7$ cycloalkylene,
 (B) V is independently chosen in each formula from —O— or —N($X_{21}$)—, wherein $X_{21}$ is from a lengthening agent L represented by Formula I above, hydrogen, $C_1$-$C_{12}$ alkyl, and $C_2$-$C_{12}$ acyl, provided that if V is —N($X_{21}$)—, V' is —$CH_2$—,
 (C) $X_{18}$ and $X_{19}$ are each independently chosen from a lengthening agent L represented by Formula I above, hydrogen and $C_1$-$C_{12}$ alkyl, and
 (D) k is chosen from 0, 1, and 2, and each $X_{20}$ is independently chosen for each occurrence from a lengthening agent L represented by Formula I above, $C_1$-$C_{12}$ alkyl, $C_1$-$C_{12}$ alkoxy, hydroxy and halogen;
(viii) a group represented by Formula vi:

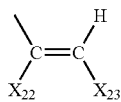

wherein
 (A) $X_{22}$ is chosen from a lengthening agent L represented by Formula I above, hydrogen and $C_1$-$C_{12}$ alkyl, and
 (B) $X_{23}$ is chosen from a lengthening agent L represented by Formula I above or an unsubstituted, mono-, or di-substituted group chosen from naphthyl, phenyl, furanyl and thienyl, wherein each substituent is independently chosen for each occurrence from $C_1$-$C_{12}$ alkyl, $C_1$-$C_{12}$ alkoxy, and halogen;
(ix) —C(O)$X_{24}$, wherein $X_{24}$ is chosen from a lengthening agent L represented by Formula I above, hydroxy, $C_1$-$C_{12}$ alkyl, $C_1$-$C_{12}$ alkoxy, phenyl that is unsubstituted or mono-substituted with $C_1$-$C_{12}$ alkyl or $C_1$-$C_{12}$ alkoxy, amino that is unsubstituted, mono- or di-substituted with at least one of $C_1$-$C_{12}$ alkyl, phenyl, benzyl, and napthyl;
(x) —O$X_7$ and —N($X_7$)$_2$, wherein $X_7$ is as set forth above;
(xi) —S$X_{11}$, wherein $X_{11}$ is as set forth above;
(xii) the nitrogen containing ring represented by Formula iv, which is set forth above;
(xiii) the group represented by one of Formula v or vi, which are set forth above; and
(xiv) immediately adjacent $R^1$ groups together a group represented by one of Formula vii, viii, and ix:

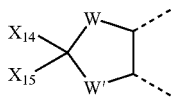

vii wherein
 (A) W and W' are independently chosen for each occurrence from —O—, —N($X_7$)—, —C($X_{14}$)—, —C($X_{17}$)—, (wherein $X_7$, $X_{14}$, and $X_{17}$ are as set forth above),
 (B) $X_{14}$, $X_{15}$ and $X_{17}$ are as set forth above, and
 (C) q is an integer chosen from 0, 1, 2, 3, and 4.

According to one non-limiting embodiment, the photochromic-dichroic compound can be a photochromic pyran that is represented by Formula II:

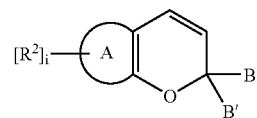

II wherein A is an aromatic ring or a fused aromatic ring chosen from: naphtho, benzo, phenanthro, fluorantheno, antheno, quinolino, thieno, furo, indolo, indolino, indeno, benzofuro, benzothieno, thiopheno, indeno-fused naphtho, heterocyclic-fused naphtho, and heterocyclic-fused benzo; and B and B' each can be independently chosen from:
 (i) hydrogen, $C_1$-$C_{12}$ alkyl, $C_2$-$C_{12}$ alkylidene, $C_2$-$C_{12}$ alkylidyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;
 (ii) phenyl that is mono-substituted at the para position with at least one substituent chosen: $C_1$-$C_7$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_4$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material;
 (iii) —CH(CN)$_2$ and —CH(COO$X_1$)$_2$, wherein $X_1$ is as set forth above;
 (iv) —CH($X_2$)($X_3$), wherein $X_2$ and $X_3$ are as set forth above;
 (v) an unsubstituted, mono-, di-, or tri-substituted aryl group, such as phenyl, naphthyl, phenanthryl, or pyrenyl; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl; wherein the substituents are independently chosen for each occurrence from:
(A) a lengthening agent L represented by Formula I above;
(B) —C(O)$X_6$, wherein $X_6$ is as set forth above;
(C) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;
(D) $C_1$-$C_{12}$ alkyl, $C_3$-$C_7$ cycloalkyl, $C_3$-$C_7$ cycloalkyloxy($C_1$-$C_{12}$)alkyl, aryl($C_1$-$C_{12}$)alkyl, aryloxy($C_1$-$C_{12}$)alkyl, mono- or di-($C_1$-$C_{12}$)alkylaryl($C_1$-$C_{12}$) alkyl, mono- or di-($C_1$-$C_{12}$)alkoxyaryl($C_1$-$C_{12}$)alkyl, haloalkyl, and mono($C_1$-$C_{12}$)alkoxy($C_1$-$C_{12}$)alkyl;
(E) $C_1$-$C_{12}$ alkoxy, $C_3$-$C_7$ cycloalkoxy; cycloalkyloxy ($C_1$-$C_{12}$)alkoxy; aryl($C_1$-$C_{12}$)alkoxy, aryloxy($C_1$-$C_{12}$)alkoxy, mono- or di-($C_1$-$C_{12}$)alkylaryl($C_1$-$C_{12}$) alkoxy, and mono- or di-($C_1$-$C_{12}$)alkoxyaryl($C_1$-$C_{12}$) alkoxy;
(F) amido, amino, mono- or di-alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;
(G) —$OX_7$ and —$N(X_7)_2$, wherein $X_7$ is as set forth above;
(H) —$SX_{11}$, wherein $X_{11}$ is as set forth above;
(I) the nitrogen containing ring represented by Formula i, which is set forth above; and
(J) the group represented by one of Formula ii or iii, which are set forth above;
(vi) an unsubstituted or mono-substituted group chosen from pyrazolyl, imidazolyl, pyrazolinyl, imidazolinyl, pyrrodlinyl, phenothiazinyl, phenoxazinyl, phenazinyl, and acridinyl, wherein each substituent is independently chosen from a lengthening agent L, $C_1$-$C_{12}$ alkyl, $C_1$-$C_{12}$ alkoxy, phenyl, hydroxy, amino or halogen;
(vii) the group represented by one of Formula iv or v, which are set forth above; and
(viii) the group represented by Formula vi, which is set forth above.

Alternatively, B and B' together can form: (a) an unsubstituted, mono- or di-substituted fluoren-9-ylidene, wherein each of said fluoren-9-ylidene substituents are chosen from $C_1$-$C_4$ alkyl, $C_1$-$C_4$ alkoxy, fluoro and chloro; (b) a saturated $C_3$-$C_{12}$ spiro-monocyclic hydrocarbon ring, e.g., cyclopropylidene, cyclobutylidene, cyclopentylidene, cyclohexylidene, cycloheptylidene, cyclooctylidene, cyclononylidene, cyclodecylidene cycloundecylidene, cyclododecylidene; (c) a saturated $C_7$-$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1] octylidene, bicyclo[3.3.1]nonan-9-ylidene, bicyclo[4.3.2] undecane; or (d) a saturated $C_7$-$C_{12}$ spiro-tricyclic hydrocarbon rings, e.g., tricyclo[2.2.1.0$^{2,6}$]heptylidene, tricyclo [3.3.1.1$^{3,7}$]decylidene, i.e., adamantylidene, and tricyclo [5.3.1.1$^{2,6}$]dodecylidene. Further according to various non-limiting embodiments discussed in more detail below, B and B' together can form indolino or benzoindolino that is unsubstituted or substituted with at least one group represented by $R^2$.

Referring again to Formula II, according to various non-limiting embodiments, "i" can be an integer chosen from 0 to the total available positions on A, and each $R^2$ can be independently chosen for each occurrence from: (i) a lengthening agent L represented by Formula I (above) and (ii) a group represented by $R^1$ (above); provided that the photochromic-dichroic compound represented by Formula II comprises at least one lengthening agent (L) represented by Formula I above.

Thus, for example, in Formula II, "i" can be at least 1 and at least one of the $R^2$ groups can be a lengthening agent L. Additionally or alternatively, the photochromic-dichroic compound can comprise at least one $R^2$ group, at least one B group, or at least one B' group that is substituted with a lengthening agent L. Thus, for example and without limitation, L can be directly bonded to the pyran group, for example, wherein i is at least 1 and $R^2$ is L, or it can be indirectly bonded to the pyran group, for example, as a substituent on an $R^2$, B, or B' group such that L extends the pyran group in an activated state such that the absorption ratio of the photochromic compound is enhanced as compared to the unextended pyran group. For example, although not limiting herein, the B or B' group can be a phenyl group that is mono-substituted with a lengthening agent L.

For example, according to various non-limiting embodiments, the photochromic-dichroic compound can be a naphtho[1,2-b]pyran represented by Formula III:

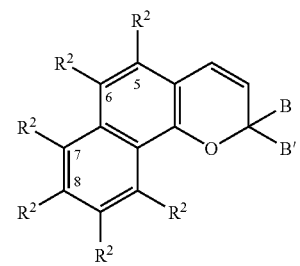

III wherein: (a) at least one of: the $R^2$ substituent in the 6-position, the $R^2$ substituent in the 8-position, B and B' comprises a lengthening agent L; (b) the $R^2$ substituent in the 6-position together with the $R^2$ substituent in the 5-position forms a group represented by one of Formula x to Formula xiv:

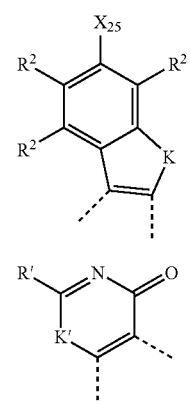

x xi

-continued

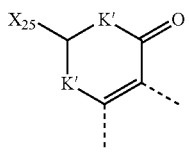
xii

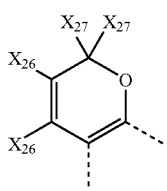
xiii

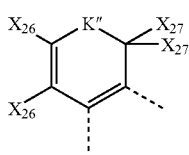
xiv wherein K is chosen from —O—, —S—, —N(X$_7$)—; and an unsubstituted C or a C substituted with alkyl, hydroxy, alkoxy, oxo, or aryl; K' is —C—, —O—, or —N(X$_7$)—; K" is chosen from —O— or —N(X$_7$)—; X$_{25}$ is a group represented by R$^2$ (which is set forth above in detail); X$_{26}$ can be chosen from hydrogen, alkyl, aryl, or together form benzo or naphtho; and each X$_{27}$ is chosen from alkyl and aryl or together are oxo; provided that at least one of: the R$^2$ substituent in the 8-position, X$_{25}$, K, K', K", B or B' comprises a lengthening agent L; or (c) the R$^2$ substituent in the 6-position together with the R$^2$ substituent in the 7-position from an aromatic group chosen from benzeno and naphtho, provided that at least one of: the R$^2$ substituent in the 8-position, B and B' comprises a lengthening agent L.

Further, according to other non-limiting embodiments, the photochromic-dichroic compound can be an indeno-fused naphtho[1,2-b]pyran represented by Formula IV:

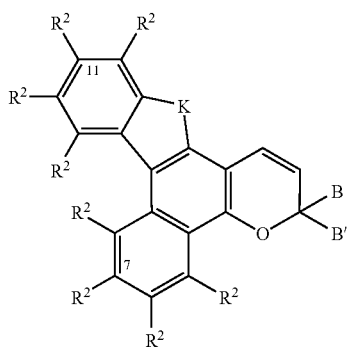
IV wherein K is as set forth above, and at least one of: the R$^2$ substituent in the 11-position, the R$^2$ substituent in the 7-po-sition, K, B and B' comprises a lengthening agent L. Further, according to one specific non-limiting embodiment, at least one of: the R$^2$ substituent in the 11-position and the R$^2$ substituent in the 7-position is a lengthening agent L.

According to other non-limiting embodiments, the photochromic-dichroic compound can be a naphtho[2,1-b]pyran represented by Formula V:

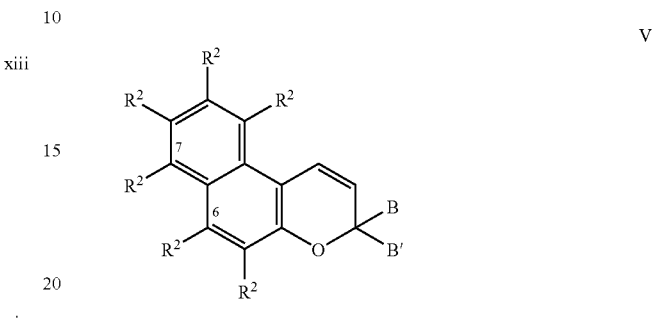
V wherein at least one of: the R$^2$ substituent in the 6-position, the R$^2$ substituent in the 7-position, B, and B' comprises a lengthening agent L. More specifically, according to one non-limiting embodiment, at least one of: the R$^2$ substituent in the 6-position and the R$^2$ substituent in the 7-position is a lengthening agent L.

Further, according to still other non-limiting embodiments, the photochromic-dichroic compound can be a benzopyran comprising a structure represented by Formula VI:

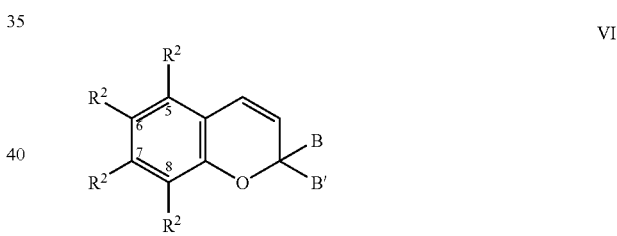
VI wherein: (a) at least one of: the R$^2$ substituent in the 5-position, the R$^2$ substituent in the 7-position, B or B' comprises a lengthening agent L; or (b) at least one of: the R substituent in the 5-position and the R$^2$ substituent in the 7-position, together with an immediately adjacent R$^2$ substituent, (i.e., the R$^2$ substituent in the 7-position together with an R$^2$ substituent in the 6- or 8-positions, or the R$^2$ substituent in the 5-position together with an R substituent in the 6-position) forms a group represented by Formula x to xiv (set forth above), provided that only one of the R$^2$ substituent in the 5-position and the R$^2$ substituent in the 7-position join together with the R$^2$ substituent in the 6-position, and provided that at least one of: the R$^2$ substituent in the 5-position, the R$^2$ substituent in the 7-position, X$_{25}$, K, K', K", B or B' comprises a lengthening agent L.

A general reaction sequence for forming photochromic-dichroic compounds that can be used in various non-limiting embodiments disclosed herein and that are generally represented by Formula II above is depicted below in Reaction Sequence A.

Reaction Sequence A

Part 1:

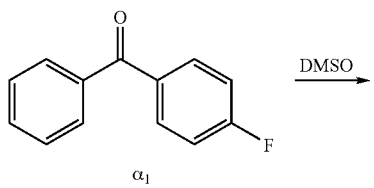

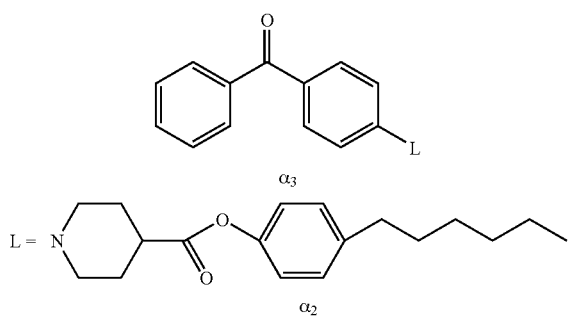

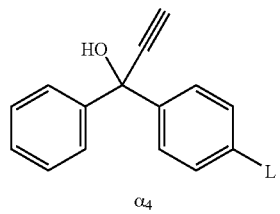

As depicted in Part 2 of Reaction Sequence A, the L substituted ketone represented by Formula $\alpha_3$ can be reacted with sodium acetylide in a suitable solvent, such as but not limited to anhydrous tetrahydrofuran (THF), to form the corresponding propargyl alcohol (represented by Formula $\alpha_4$).

Part 3:

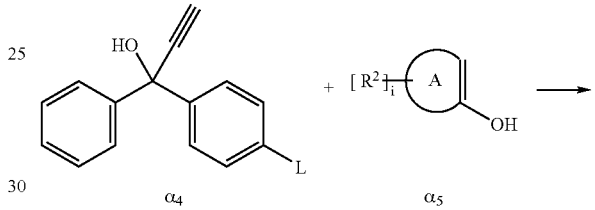

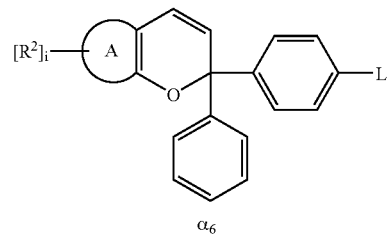

In Reaction Sequence A, Part 1, 4-fluorobenzophenone, which is represented by Formula $\alpha_1$, can be reacted under nitrogen in the anhydrous solvent dimethyl sulfoxide (DMSO) with a lengthening agent L represented by Formula $\alpha_2$, to form an L substituted ketone represented by Formula $\alpha_3$. It will be appreciated by those skilled in the art that 4-fluorobenzophenone can either be purchased or prepared by Friedel-Crafts methods known in the art. For example, see the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

Part 2:

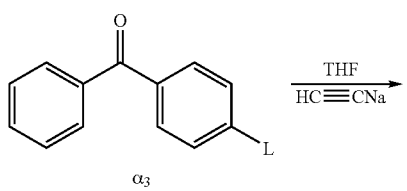

In Part 3 of Reaction Sequence A, the propargyl alcohol represented by Formula $\alpha_4$ can be coupled with a hydroxy substituted A group (represented by Formula $\alpha_5$) to form the photochromic pyran represented by Formula $\alpha 6$ according to one non-limiting embodiment disclosed herein. Optionally, the A group can be substituted with one or more $R^2$ groups, each of which may comprise a lengthening agent L that is the same or different from the remaining L substituents. Non-limiting examples of A and $R^2$ groups that are suitable for use in conjunction with various non-limiting embodiments disclosed herein are set forth above in detail. Non-limiting examples of general reaction sequences for forming hydroxylated A groups that are substituted with at least one lengthening agent L, are shown below in Reaction Sequences B, C, and D.

Although Reaction Sequence A depicts a general reaction sequence for forming a photochromic compound represented by Formula II and having B and B' groups selected from L substituted phenyl and phenyl, it will be appreciated by those skilled in the art that photochromic compounds generally represented by Formula II and having B and B' groups other than those shown in Formula $\alpha_6$ above, and which optionally can be substituted with one or more L groups or one or more $R^2$ groups comprising L, can be prepared from commercially available ketones, or by reaction of an acyl halide with a substituted or unsubstituted material such as naphthalene or a heteroaromatic compound. Non-limiting examples of B and B' substituent groups that are suitable for use in conjunction with various non-limiting embodiments disclosed herein are set forth above in detail.

Reaction Sequences B, C and D depict three different general reaction sequences for forming hydroxylated A groups that are substituted with at least one lengthening agent L, that can be used in the formation of photochromic pyrans according to various non-limiting embodiments disclosed herein. For example, although not limiting herein, as discussed above in Reaction Sequence A, the resulting L substituted hydroxylated A group can be coupled with propargyl alcohol to form a photochromic pyran according to various non-limiting embodiments disclosed herein. Further, as discussed above, optionally, the A group can also be substituted with one or more additional $R^2$ groups, each of which may comprise a lengthening agent L that is the same or different from the remaining Ls.

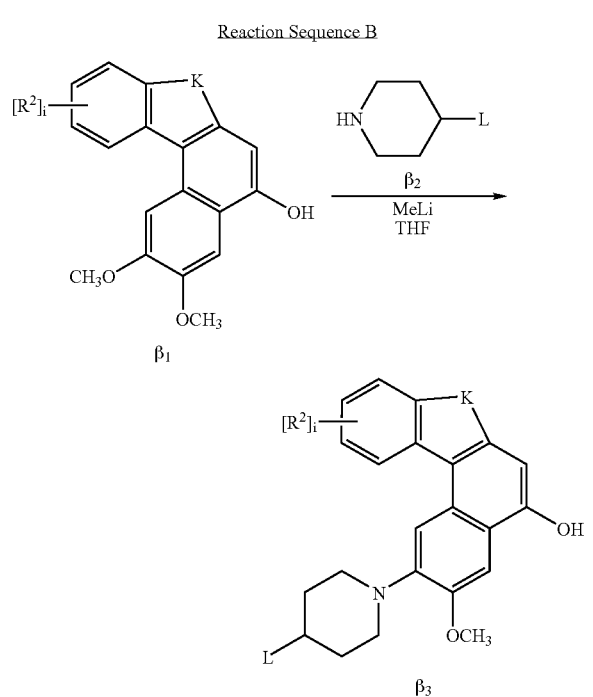

In Reaction Sequence B, the hydroxlylated A group represented by Formula $\beta_1$ is reacted with the L substituted piperidine represented by Formula β2 in the presence of an alkyl lithium, such as but not limited to methyllithium (MeLi), in anhydrous tetrahydrofuran to produce the L substituted $R^2$ group attached to the hydroxylated A group represented by Formula $\beta_3$. Further, as indicated above, the A group may also be substituted with one or more additional $R^2$ groups, each of which may also comprise a lengthening agent L that is the same or different from the remaining Ls. Further, K can be chosen from —O—, —S—, —N($X_7$)— or carbon that is substituted or unsubstituted. For example, K can be a carbon that is di-substituted with methyl or can be substituted with an ethyl group and a hydroxyl group.

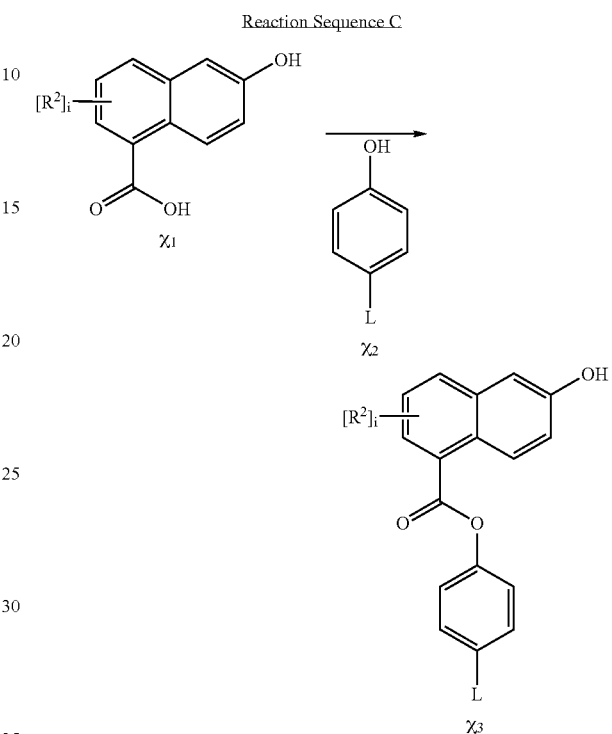

In Reaction Sequence C, the $R^2$ substituted hydroxylated A group represented by Formula $\chi_1$ is reacted with the L substituted phenol represented by Formula $\chi_2$ in an esterification reaction in the presence of dicyclohexylcarbodiimide in methylene chloride to produce the L substituted $R^2$ group attached to the hydroxylated A group represented by Formula $\chi_3$. Further, as indicated in Reaction Sequence C, the group represented by Formula $\chi_3$ optionally can be substituted with one or more additional $R^2$ groups, each of which may also comprise a lengthening agent L that is the same or different from the remaining Ls.

In Reaction Sequence D (below), the hydroxy substituted naphthol represented by Formula $\delta_1$ is reacted with chlorine to form the compound represented by Formula $\delta_2$. The compound represented by Formula $\delta_2$ is reacted with the L substituted piperidine represented by Formula $\delta_3$ to form the material represented by Formula $\delta_4$. The material represented by Formula $\delta_4$ is reduced in a hydrogen atmosphere over a palladium on carbon catalyst to form the L substituted $R^2$ group attached to the hydroxylated A group represented by Formula $\delta_5$.

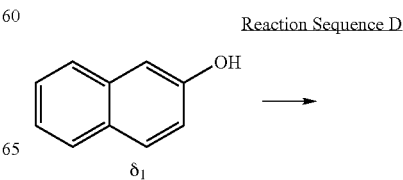

-continued
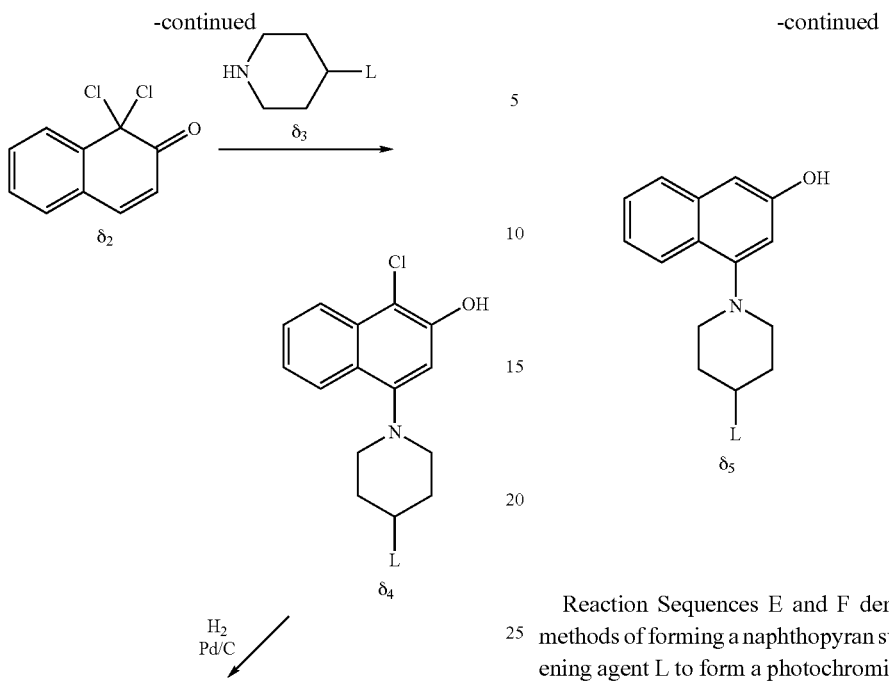
Reaction Sequences E and F demonstrate two different methods of forming a naphthopyran substituted with a lengthening agent L to form a photochromic naphthopyran according to various non-limiting embodiments disclosed herein.
Reaction Sequence E
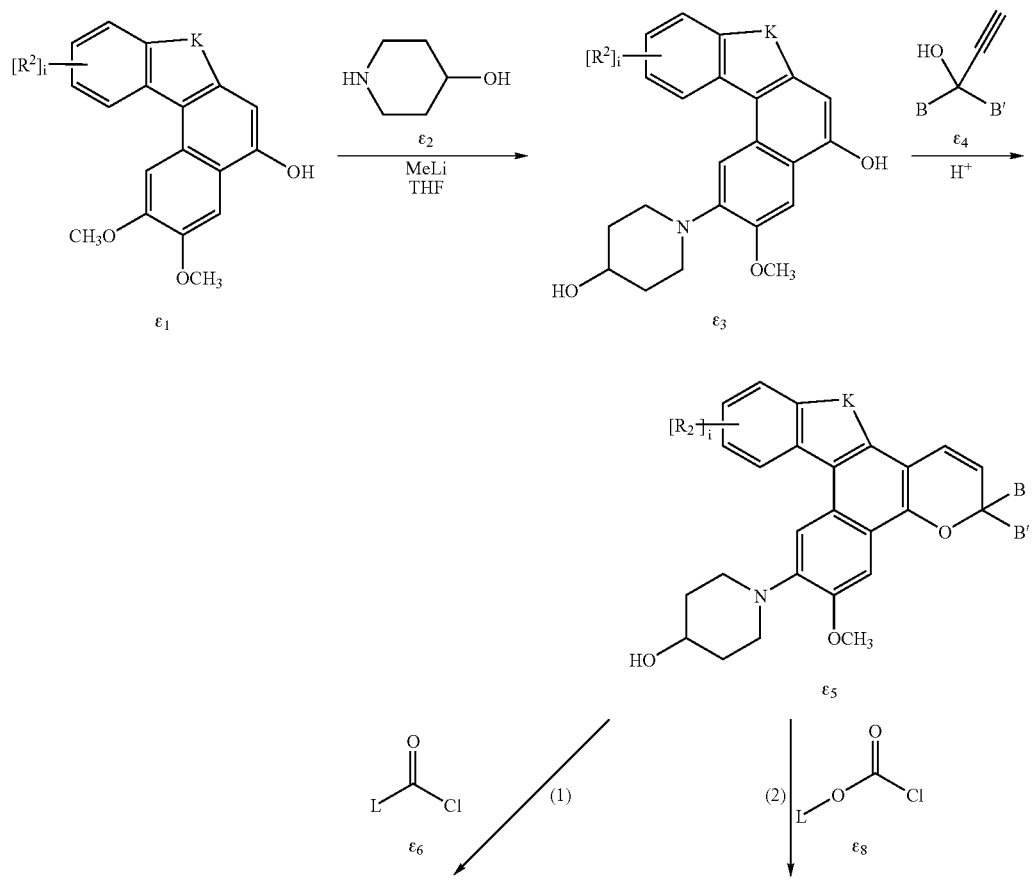

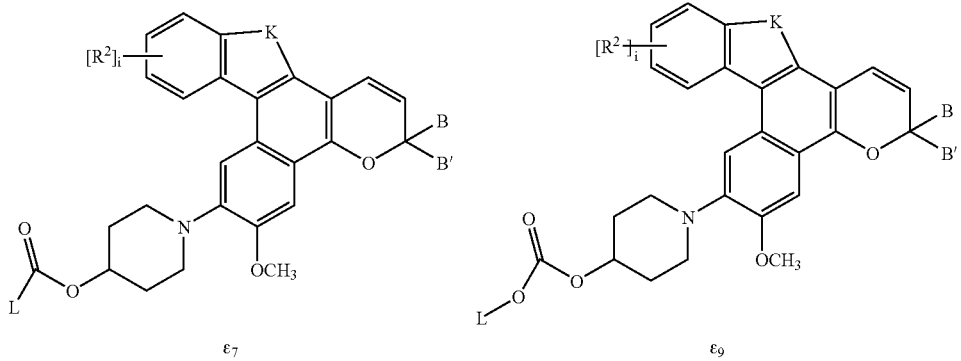

ε₇                                    ε₉

In Reaction Sequence E, the hydroxy substituted A group represented by Formula $\epsilon_1$, which is optionally substituted with at least one $R^2$ group, is reacted with the hydroxy substituted piperidine represented by Formula $\epsilon_2$ in the presence of an alkyl lithium, such as but not limited to methyllithium (MeLi), in anhydrous tetrahydrofuran to produce the 4-hydroxy piperidinyl attached to the hydroxylated A group represented by Formula $\epsilon_3$. The compound represented by Formula $\epsilon_3$ is then coupled with the propargyl alcohol represented by Formula $\epsilon_4$ to form the 4-hydroxy piperidinyl attached to the indeno-fused naphthopyran represented by Formula $\epsilon_5$. The naphthopyran represented by Formula $\epsilon_5$ can be further reacted, as indicated by path (1) Reaction Sequence E, in an acetylation reaction using a tertiary amine, such as but not limited to triethylamine, in a solvent, such as but not limited to methylene chloride, with the L substituted compound represented by Formula $\epsilon_6$ to produce the L substituted piperidinyl attached to the indeno-fused naphthopyran according to one non-limiting embodiment disclosed herein and represented by Formula $\epsilon_7$. Alternatively, as indicated by path (2), the naphthopyran represented by Formula $\epsilon_5$ can be reacted with the L substituted compound represented by Formula $\epsilon_8$ to produce the L substituted piperidinyl attached to the indeno-fused naphthopyran according to one non-limiting embodiment disclosed herein and represented by Formula $\epsilon_9$. Further, as indicated in Reaction Sequence E, the L substituted piperidinyl attached to the indeno-fused naphthopyrans represented by Formula $\epsilon_7$ and Formula $\epsilon_9$ can optionally be substituted with one or more additional $R^2$ groups, each of which may comprise lengthening agent L that is the same or different from the remaining Ls.

In Reaction Sequence F (below), the hydroxylated A group represented by Formula $\phi_1$ is coupled with the propargyl alcohol represented by Formula $\phi_2$ to produce the naphthopyran represented by Formula $\phi_3$. The naphthopyran by Formula $\phi_3$ is then reacted with the L substituted phenylamine of Formula $\phi_4$ to produce the L substituted phenylamine attached to the naphthopyran represented by Formula $\phi_5$ according to various non-limiting embodiments disclosed herein. Non-limiting examples of suitable B and B' substituent groups are set forth above in detail.

Reaction Sequence F

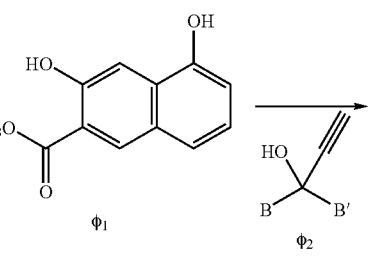

φ₁                    φ₂

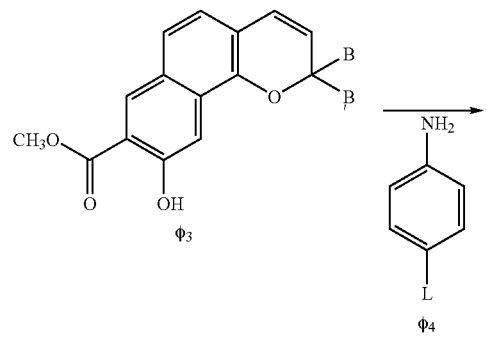

φ₃                    φ₄

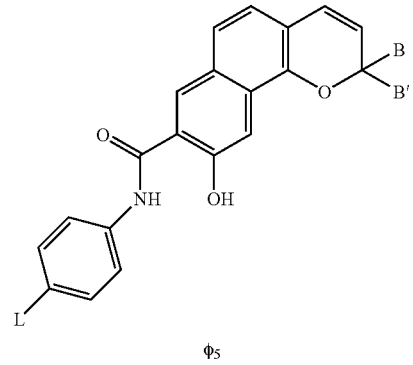

φ₅

Although not limiting herein, in the hydroxy substituted A group represented by Formulae $\beta_1$ and $\epsilon_1$ (which are set forth in Reaction Sequences B and E, respectively), K can be a carbon that is di-substituted with methyl to form 2,3-dimethoxy-7,7-dimethyl-7H-benzo[c]fluoren-5-ol. Those skilled in the art will recognize numerous methods of making such a hydroxy substituted A group. For example, and without limitation, one method of forming 2,3-dimethoxy-7,7-dimethyl-7H-benzo[c]fluoren-5-ol is set forth in step 2 of Example 9 of U.S. Pat. No. 6,296,785, which is hereby specifically incorporated by reference. More specifically, as set forth in step 2 of Example 9 of U.S. Pat. No. 6,296,785, one non-limiting method of forming 2,3-dimethoxy-7,7-dimethyl-7H-benzo[c]fluoren-5-ol is as follows:

In a first step, 1,2-dimethoxybenzene (92.5 grams) and a solution of benzoyl chloride (84.3 grams) in 500 milliliters (mL) of methylene chloride is added to a reaction flask fitted with a solid addition funnel under a nitrogen atmosphere. Solid anhydrous aluminum chloride (89.7 grams) is added to the reaction mixture with occasionally cooling of the reaction mixture in an ice/water bath. The reaction mixture is stirred at room temperature for 3 hours. The resulting mixture is poured into 300 mL of a 1:1 mixture of ice and 1 N hydrochloric acid and stirred vigorously for 15 minutes. The mixture is extracted twice with 100 mL methylene chloride. The organic layers are combined and washed with 50 mL of 10 weight percent sodium hydroxide followed by 50 mL of water. The methylene chloride solvent is removed by rotary evaporation to give a yellow solid. Recrystallization from 95 percent ethanol yields 147 grams of beige needles having a melting point of 103-105° C. The product is believed to have a structure consistent with 3,4,-dimethoxybenzophenone.

In a second step, potassium t-butoxide (62 grams) and 90 grams of the product from preceding Step 1, is added to a reaction flask containing 300 mL of toluene under a nitrogen atmosphere. The mixture is heated to reflux and dimethyl succinate (144.8 grams) is added dropwise over 1 hour. The mixture is refluxed for 5 hours and cooled to room temperature. 300 mL of water is added to the reaction mixture and vigorously stirred for 20 minutes. The aqueous and organic phases separate and the organic phase is extracted with 100 mL portions of water three times. The combined aqueous layers are washed with 50 mL portions of chloroform three times. The aqueous layer is acidified to pH 2 with 6N hydrochloric acid and a precipitate forms and is removed by filtration. The aqueous layer is extracted with three 100 mL portions of chloroform. The organic extracts are combined and concentrated by rotary evaporation. The resulting oil is believed to have a structure consistent with a mixture of (E and Z) 4-(3,4-dimethoxyphenyl)$_4$-phenyl-3-methoxycarbonyl-3-butenoic acids.

In a third step, the product from preceding Step 2 (8.6 grams), 5 mL of acetic anhydride, and 50 mL of toluene are added to a reaction flask under a nitrogen atmosphere. The reaction mixture is heated to 110° C. for 6 hours and cooled to room temperature, and the solvents (toluene and acetic anhydride) are removed by rotary evaporation. The residue is dissolved in 300 mL of methylene chloride and 200 mL of water. Solid sodium carbonate is added to the biphasic mixture until bubbling ceased. The layers separate and the aqueous layer is extracted with two 50 mL portions of methylene chloride. The organic layers are combined and the solvent (methylene chloride) is removed by rotary evaporation to yield a thick red oil. The oil is dissolved in warm methanol and chilled at 0° C. for 2 hours. The resulting crystals are collected by vacuum filtration, washed with cold methanol to produce 5 grams of a product having a melting point of 176-177° C. The recovered solid product is believed to have structures consistent with a mixture of 1-(3,4-dimethoxyphenyl)-2-methoxycarbonyl-4-acetoxynaphthalene and 1-phenyl-2-methoxycarbonyl-4-acetoxy-6,7-dimethoxynaphthalene.

In a fourth step, five (5) grams of the product mixture from preceding Step 3, 5 mL of 12M hydrochloric acid, and 30 mL of methanol are combined in a reaction flask and heated to reflux for 1 hour. The reaction mixture is cooled and the resulting precipitate is collected by vacuum filtration and washed with cold methanol. The product is purified by filtering through a plug of silica gel using a 2:1 mixture of hexane and ethyl acetate as the eluant. Concentration of the filtrate by rotary evaporation yields 3 grams of a beige solid that is believed to have a structure consistent with 1-phenyl-2-methoxycarbonyl-6,7-dimethoxynaphth-4-ol.

In a fifth step, a reaction flask is charged with 2.8 grams of the product of preceding Step 4 under a nitrogen atmosphere. Anhydrous tetrahydrofuran (40 mL) is added to the flask. The reaction mixture is cooled in a dry ice/acetone bath and 41 mL of a methyl magnesium chloride solution (1M in tetrahydrofuran) is added dropwise over 15 minutes. The resulting yellow reaction mixture is stirred at 0° C. for 2 hours and slowly warmed to room temperature. The reaction mixture is poured into 50 mL of an ice/water mixture. Ether (20 mL) is added, and the layers separate. The aqueous layer is extracted with two 20 mL portions of ether, and the organic portions are combined and washed with 30 mL of water. The organic layer is dried over anhydrous magnesium sulfate and concentrated by rotary evaporation. The resulting oil is transferred into a reaction vessel (fitted with a Dean-Stark trap) containing 50 mL of toluene to which two drops of dodecylbenzene sulfonic acid are added. The reaction mixture is heated to reflux for 2 hours and cooled. The toluene is removed via rotary evaporation to yield 2 grams of the desired compound.

According to another non-limiting embodiment, the photochromic-dichroic compound can be a photochromic spiropyran or spiro-oxazine that is represented by Formula VII:

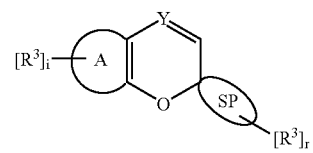

VII wherein:
(a) A is chosen from naphtho, benzo, phenanthro, fluorantheno, antheno, quinolino, thieno, furo, indolo, indolino, indeno, benzofuro, benzothieno, thiopheno, indenofused naphtho, heterocyclic-fused naphtho, and heterocyclic-fused benzo;
(b) Y is C or N;
(c) SP is a spiro-group chosen from indolino and benzindolino; and
(d) i is an integer chosen from 0 to the total number of available positions on A, r is an integer chosen from 0 to the total number available positions on SP, provided that the sum of i+r is at least one, and each $R^3$ is independently chosen for each occurrence from:
(i) a lengthening agent L represented by Formula I above; and
(ii) a group represented by $R^1$ above;

provided that the photochromic-dichroic compound represented by Formula VII comprises at least one lengthening agent (L) represented by Formula I above.

As discussed above with respect to the photochromic compounds generally represented by Formula II disclosed herein, the photochromic compounds generally represented by Formula VII can be extended at any available position by substitution with L or an $R^3$ group substituted with L, and/or in any desired direction by numerous combinations of substitutions of available positions with L or $R^3$ groups substituted with L. Thus, for example, although not limiting herein, the photochromic compounds generally represented by Formula VII can be extended by substituting the SP group with L or an $R^3$ group substituted with L, and/or by substituting the A group with L or an $R^3$ group substituted with L so as to provided a desired average absorption ratio of the photochromic compound. For example, although not limiting herein, according to certain non-limiting embodiments the photochromic-dichroic compound can be represented by Formula VIII:

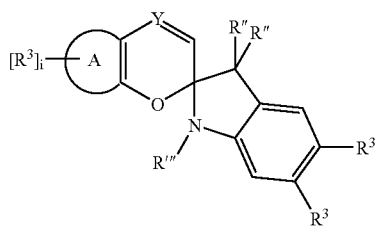

VIII wherein each R" is independently chosen for each occurrence from hydrogen, a substituted or unsubstituted alkyl, cycloalkyl, arylalkyl, or together form cycloalkyl that is substituted or unsubstituted; R''' is chosen from an alkyl, aryl, or arylalkyl group that is unsubstituted or substituted with at least one of: (i) —CH(CN)$_2$ or —CH(COOX$_1$)$_2$; (ii) —CH(X$_2$)(X$_3$); and (iii) —C(O)X$_{24}$ (wherein X$_1$, X$_2$, X$_3$, and X$_{24}$ are as set forth above); and (iv) halogen, hydroxy, ester, or amine; and wherein at least one of i and r is at least 1, and at least one $R^3$ comprises L. Further, according to one non-limiting embodiment, at least one $R^3$ is L. As discussed above with respect to Formula VII, Y in Formula VIII can be chosen from C or N. For example, according to various non-limiting embodiments, Y can be C, and the photochromic compound can be a spiro(indolino)pyran. According to other non-limiting embodiments, Y can be N, and the photochromic compound can be a spiro(indolino)oxazine.

According to another non-limiting embodiment, the photochromic-dichroic compound can be represented by Formula IX:

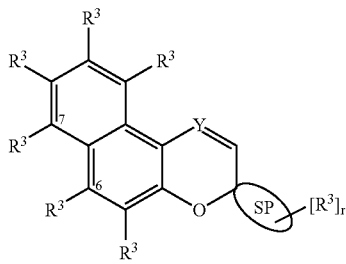

IX wherein at least one of: the $R^3$ in the 6-position or the $R^3$ in the 7-position comprises a lengthening agent L. Further, according to one specific non-limiting embodiment, at least one of the $R^3$ group in the 6-position or the $R^3$ group 7-position of Formula DC is a lengthening agent L.

According to still another non-limiting embodiment, the photochromic-dichroic compound can be represented by Formula X:

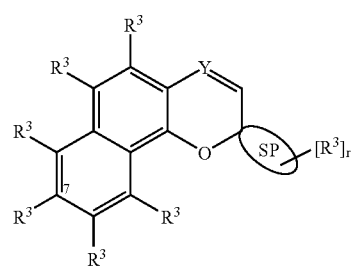

X wherein at least the $R^3$ in the 7-position comprises a lengthening agent L. Further, according to one specific non-limiting embodiment, the $R^3$ group in the 7-position is a lengthening agent L.

According to yet another non-limiting embodiment, the photochromic-dichroic compound can be represented by Formula XI:

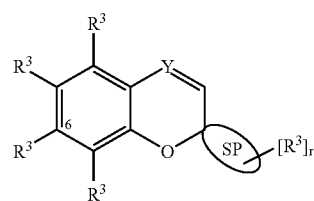

XI wherein at least the $R^3$ group in the 6-position comprises a lengthening agent L. Further, according to various non-limiting embodiments, the $R^3$ group in the 6-position is a lengthening agent L.

A general reaction sequence for synthesizing photochromic-dichroic compounds that can be used in various non-limiting embodiments disclosed herein and that are generally represented by Formula VII is depicted below in Reaction Sequence G.

Reaction Sequence G

Part 1:

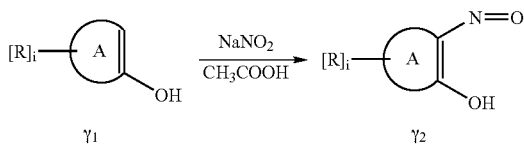

Reaction Sequence G, Part 1 depicts a general nitrosation process in which the hydroxylated A group represented by of Formula $\gamma_1$ is reacted with sodium nitrite in the presence of an acid, such as but not limited to acetic acid, to produce the nitroso-substituted A group represented by Formula $\gamma_2$. Suitable non-limiting examples of A groups include naphthol benzo, phenanthro, fluorantheno, antheno, quinolino, indeno-fused naphtho, heterocyclic-fused naphtho, and heterocyclic-fused benzo. Optionally, the A group can be substituted with one or more $R^3$ groups, each of which may comprise a lengthening agent L that is the same or different from the remaining Ls.

Part 2:

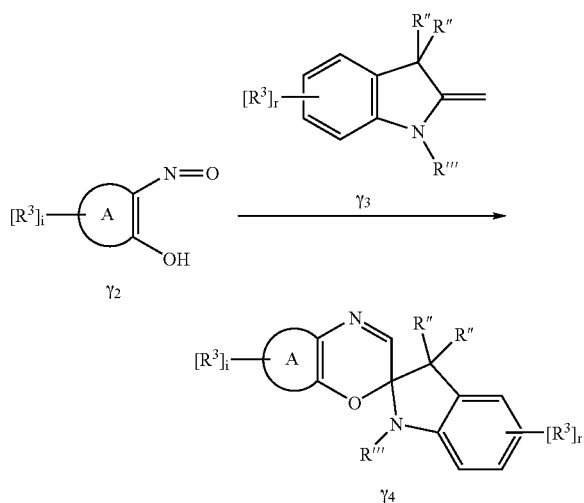

In Part 2 of Reaction Sequence G, the nitroso-substituted A group represented by Formula γ₂ is coupled with a Fischer's base represented by Formula γ₃. The coupling is conducted in a solvent, such as but not limited to absolute ethanol, and heated under reflux conditions to produce the photochromic oxazine represented by Formula γ₄ according to various non-limiting embodiments disclosed herein.

The general nitrosation process shown in Part 1 of Reaction Sequence G is more specifically set forth in the following two sequences (Reaction Sequences H and I), which generally depict two nitroso phenol synthesis processes for producing nitroso-substituted A groups, which can optionally be substituted with at least one $R^3$, that can be used in coupling reactions to produce the oxazine products of the present invention. As illustrated in Path (2) of Sequences H and I, prior to reacting with $NaNO_2$, the intermediate compound can be further reacted with one or more other reactants to form a suitable lengthening agent L on the A group.

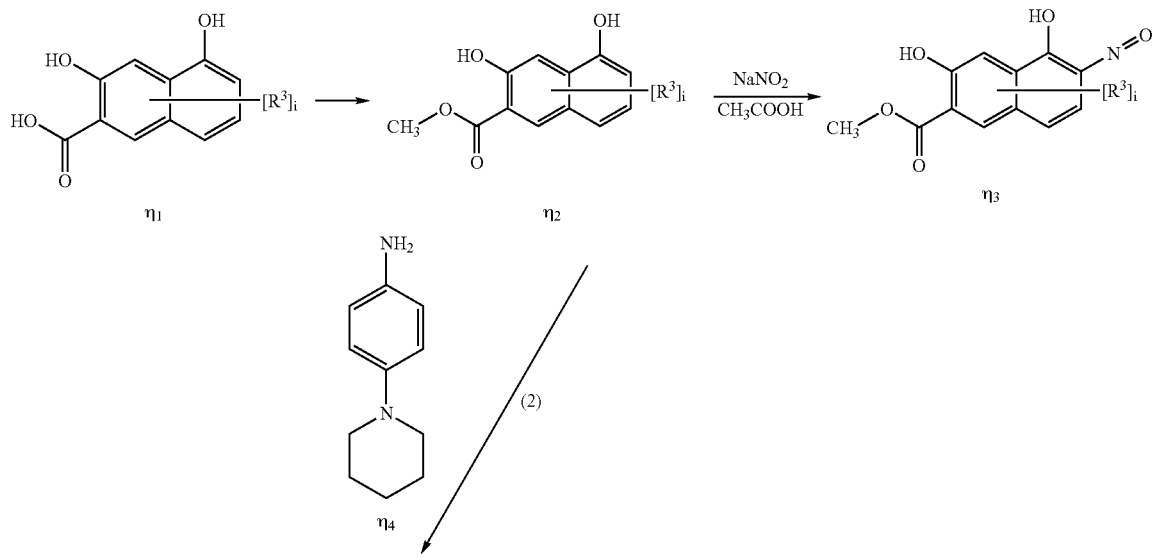

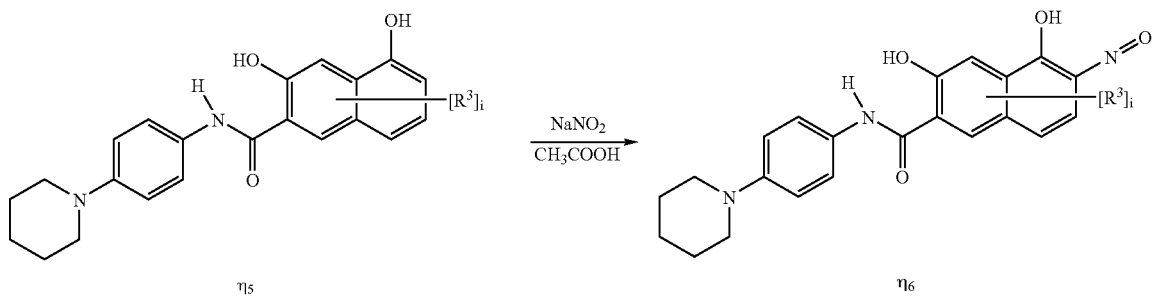

More specifically, in Reaction Sequence H, the carboxylic acid of the hydroxylated A group represented by Formula $\eta_1$ is converted into ester of hydroxylated A group represented by Formula $\eta_2$. Ester of the hydroxylated A group represented by Formula $\eta_2$ can then be reacted with sodium nitrite in the presence of an acid, such as but not limited to acetic acid, to produce the nitroso-substituted A group of Formula $\eta_3$. Alternatively, as shown in Path (2), ester of hydroxylated A group represented by Formula $\eta_2$ can be reacted with 4-piperidinoaniline (represented by Formula $\eta_4$) under basic conditions to produce the L substituted compound represented by Formula $\eta_5$. The L substituted compound represented by Formula $\eta_5$ is then subjected to the nitrosation reaction to produce the L and nitroso substituted A group represented Formula $\eta_6$. Further, the L and nitroso substituted A group optionally can be substituted with one or more $R^3$ groups, each of which can comprise a lengthening agent L which is the same or different from the remaining Ls.

As discussed above with respect to Reaction Sequence H, in Reaction Sequence I (below) the carboxylic acid of the hydroxylated A group represented by Formula $\iota_1$ is converted into the ester of the hydroxylated the A group represented by Formula $\iota_2$. The ester of hydroxylated A group represented by Formula $\iota_2$ can then be reacted with sodium nitrite in the presence of an acid, such as but not limited to acetic acid, to produce the nitroso-substituted A group of Formula $\iota_3$. Alternatively, as shown in Path (2), ester of hydroxylated the A group represented by Formula $\iota_2$ can be reacted with 4-phenyl aniline (represented by Formula $\iota_4$) under basic conditions to produce the L substituted 4-phenyl aniline represented by Formula $\iota_5$. The L substituted 4-phenyl aniline represented by Formula $\iota_5$ is then subjected to the nitrosation reaction to produce the L and nitroso substituted A group represented Formula $\iota_6$. As discussed above, the (L substituted (nitroso substituted A groups)), optionally can be substituted with one or more $R^3$ groups, each of which can comprise a lengthening agent L which is the same or different from the remaining Ls.

Reaction Sequence I

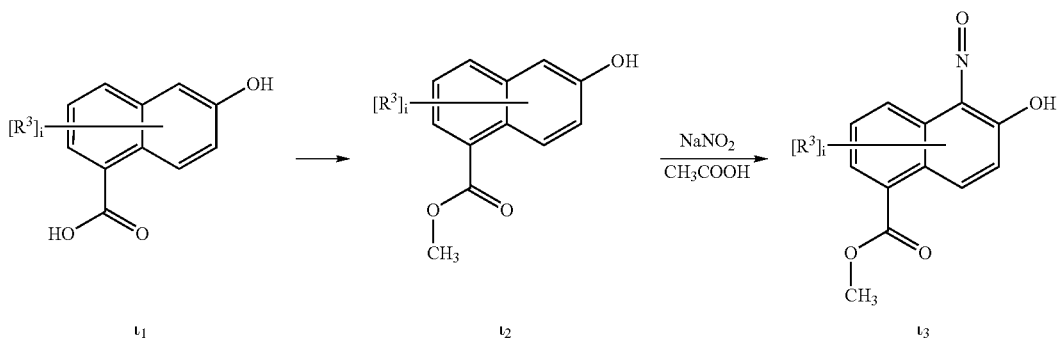

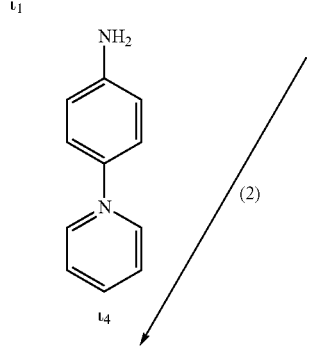

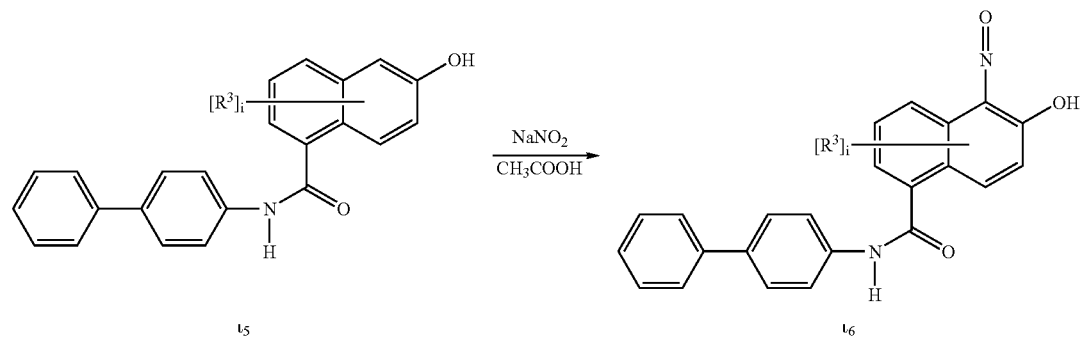

More specific reaction sequences for synthesizing the photochromic compounds according to various non-limiting embodiments disclosed herein are depicted below in Reaction Sequences J and K.

In Reaction Sequence J (below), a nitrosophenol represented by Formula $\phi_1$ is reacted in methanol with a lengthening agent L, which is piperazino phenol (represented by Formula $\phi_2$), to form the L substituted nitrosonaphthol represented by Formula $\phi_3$. As depicted in Reaction Sequence J, the L substituted nitrosonaphthol can be further substituted with one or more R groups, each of which may comprise a lengthening agent L that is the same or different from the remaining L substituents. The L substituted nitrosonaphthol represented by Formula $\phi_3$ is then coupled by heating with the Fischer's base represented by Formula $\phi_4$ to produce the L substituted naphthoxazine represented by Formula $\phi_5$.

With continued reference to Reaction Sequence J, the L substituted naphthoxazine represented by Formula $\phi_5$ can be further extended by reacting the L substituted naphthoxazine with another L substituted compound represented by Formula $\phi_6$ to produce a naphthoxazine represented by Formula $\phi_7$ according to various non-limiting embodiments disclosed herein. Further, as previously discussed and as depicted in Reaction Sequence J, naphthoxazine represented by Formula $\phi_7$ optionally can be substituted with one or more $R^3$ groups, each of which may comprise a lengthening agent L that is the same or different from the remaining Ls.

As illustrated above in Reaction Sequence J, generally after coupling the nitrosophenol with the Fischer's base, the resultant naphthoxazine can be further reacted with one or more other reactants to extend the naphthoxazine with lengthening agent L. However, those skilled in the art will appreci-

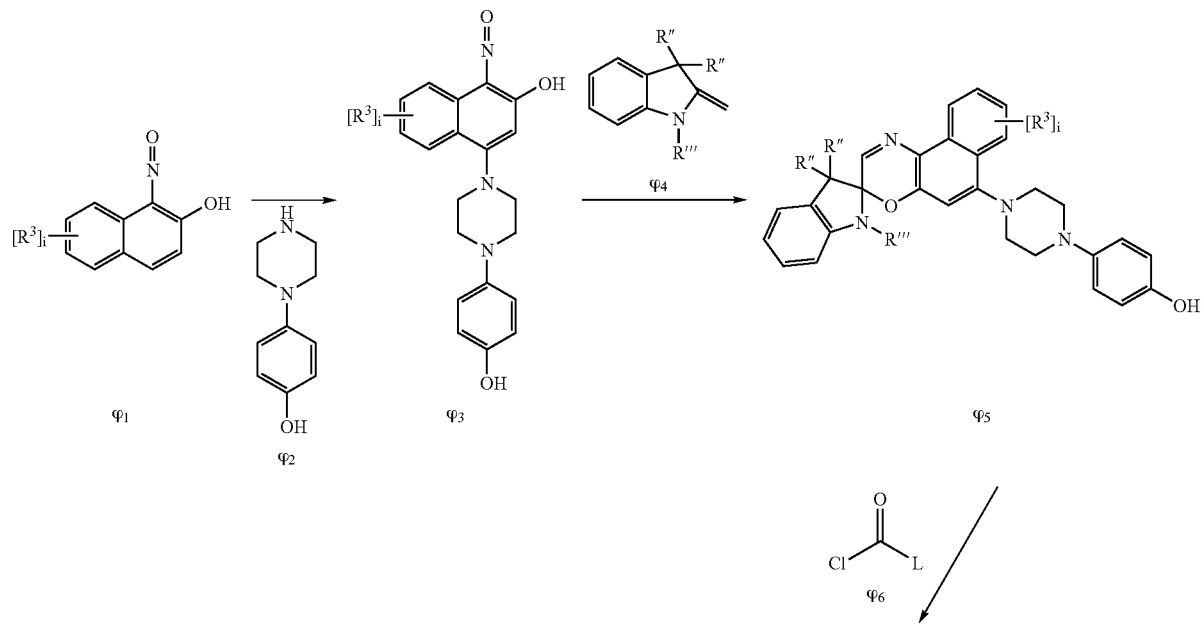

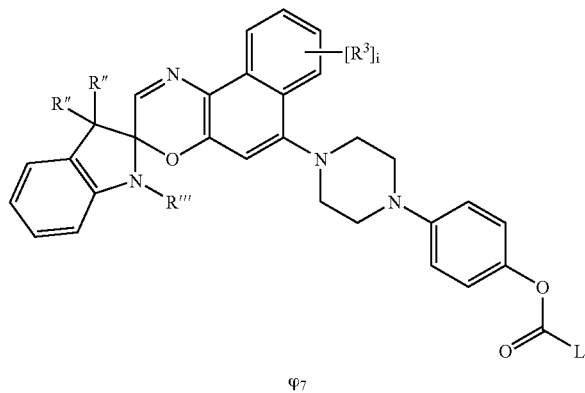

ate that, additionally or alternatively, prior to coupling the nitrosophenol with the Fischer's base, the nitrosophenol can be reacted to substitute the nitrosophenol with one or more lengthening agents L (for example as shown above in Reaction Sequences H and I). Further, such L substituted nitrosophenols can be coupled with a Fischer's base to form an L-substituted naphthoxazine as generally depicted in Reaction Sequence K, below.

More specifically, in Reaction Sequence K, an L substituted piperidinylnaphthol represented by Formula $\kappa_1$ is reacted with trialkoxymethane and heated to form the L and formyl substituted naphthol represented by Formula $\kappa_2$. The compound represented by Formula $\kappa_2$ is then reacted with the Fischer's base (represented by Formula $\kappa_3$) to produce the L substituted spironaphthopyran represented by Formula $\kappa_4$ according to various non-limiting embodiments disclosed herein.

As previously discussed, generally after coupling the nitrosophenol with the Fischer's base (for example as shown in Reaction Sequence J), the resultant naphthoxazine can be further reacted with one or more other reactants to extend the naphthoxazine with lengthening agent L. Several non-limiting examples of such extension are provided in the generalized Reaction Sequence M below.

More specifically, in Reaction Sequence M (below), three paths for adding a lengthening agent L to a naphthoxazine to produce the photochromic oxazines according to various non-limiting embodiments disclosed herein. In the first path (1), the naphthoxazine represented by Formula $\mu_2$ is reacted with hydroxyphenylpiperazine to produce the material represented by Formula $\mu_2$. The material represented by Formula $\mu_2$ is benzoylated with hexylbenzoylchloride to produce the material represented by Formula $\mu_3$. In the second path (2), the material represented by Formula $\mu_1$ undergoes hydrolysis and is converted into the material of Formula $\mu_4$. In an esterification reaction with a phenol-like material in the presence of dicyclohexylcarbodiimide in methylene chloride the material represented by Formula $\mu_4$ is converted into the material represented by Formula $\mu_5$ having the tetrahydropyran protecting group. The material represented by Formula $\mu_5$ is deprotected by a dilute solution of hydrochloric acid in an alcoholic solvent, such as but not limited to ethanol, to form the material represented by Formula $\mu_6$. The material represented by Formula $\mu_6$ is reacted with a cholesterol chloroformate to form the material represented by Formula $\mu_7$. In the third path (3), the material represented by Formula $\mu_6$ is benzoylated with 4-phenylbenzoylchloride to form the material represented by Formula $\mu_8$.

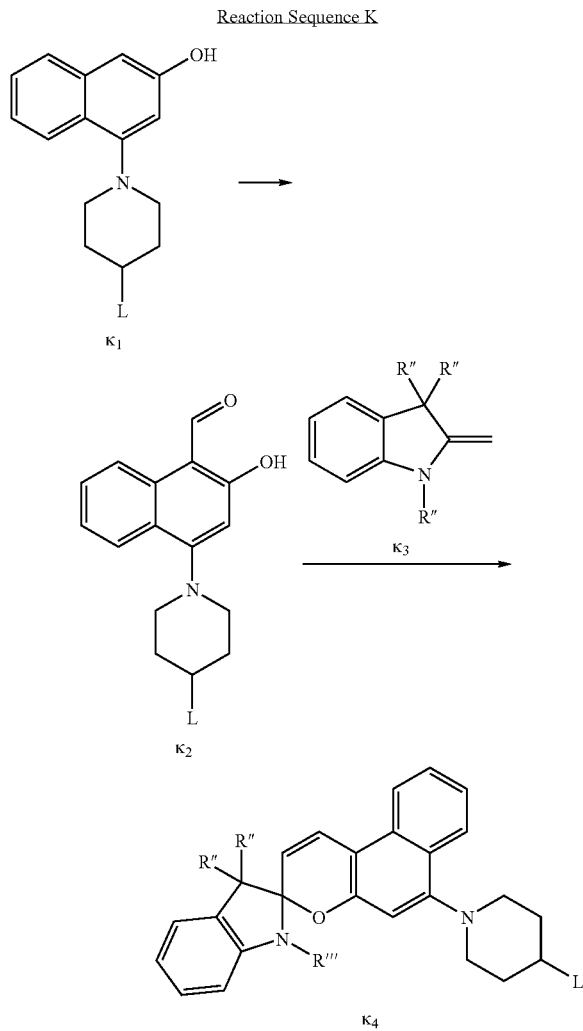

Reaction Sequence K

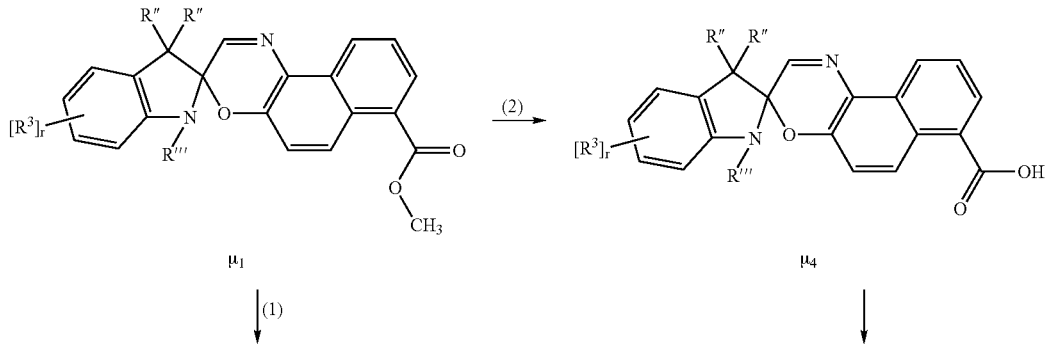

Reaction Sequence M

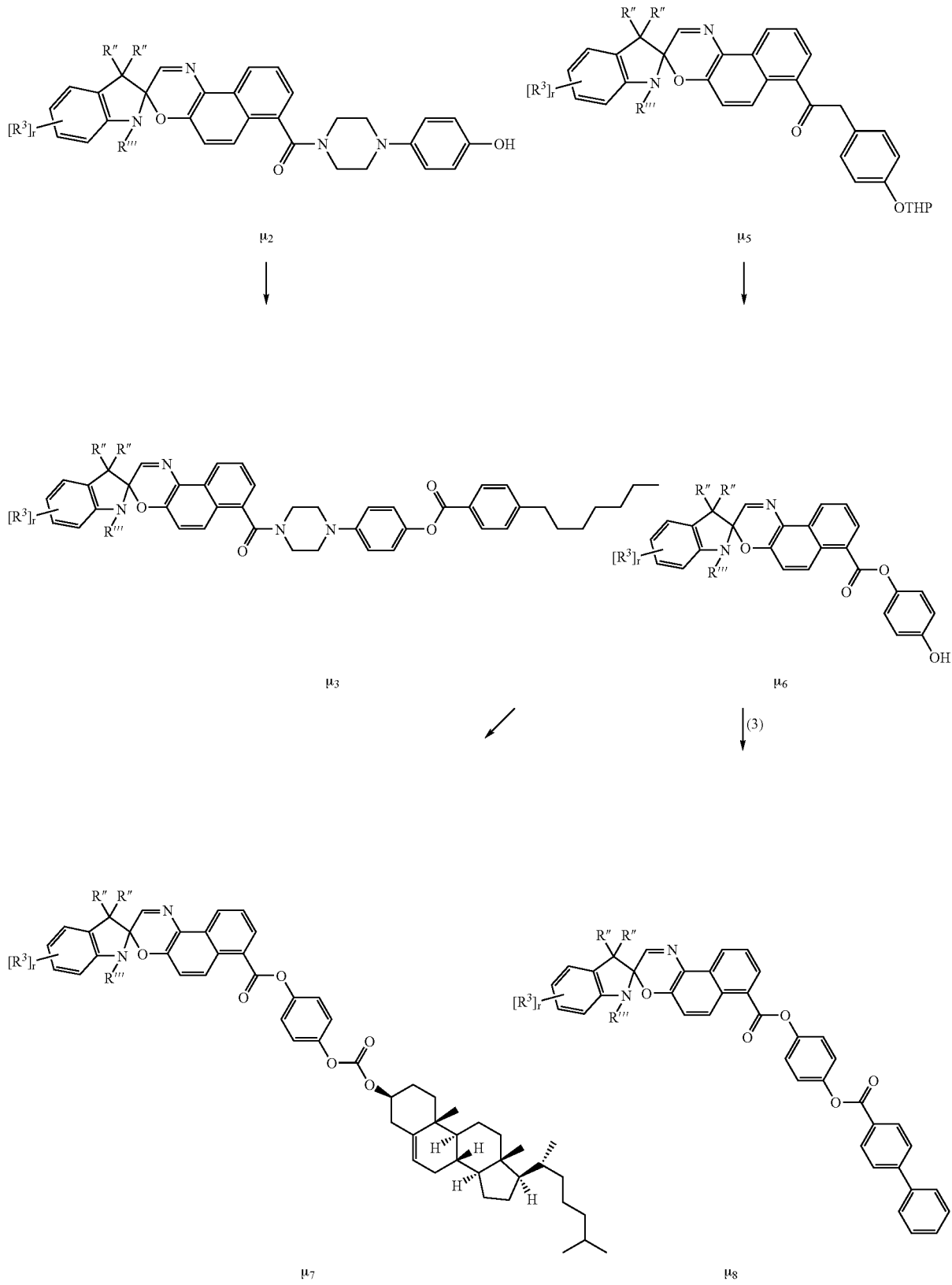

According to another non-limiting embodiment the photochromic-dichroic compound can be represented by Formula XII:

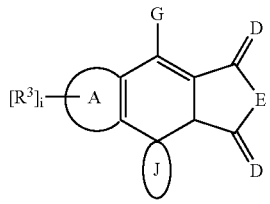

XII wherein
(a) A is chosen from naphtho, benzo, phenanthro, fluorantheno, antheno, quinolino, thieno, furo, indolo, indolino, indeno, benzofuro, benzothieno, thiopheno, indeno-fused naphtho, heterocyclic-fused naphtho, and heterocyclic-fused benzo;
(b) J is a spiro-alicyclic ring;
(c) each D is independently chosen from O, N(Z), C($X_4$), C(CN)$_2$ wherein Z is independently chosen for each occurrence from hydrogen, $C_1$-$C_6$ alkyl, cycloalkyl and aryl;
(d) G is group chosen from alkyl, cycloalkyl, and aryl, which can be unsubstituted or substituted with at least one substituent $R^4$;
(e) E is —O— or is —N($R^5$)—, wherein $R^5$ is chosen from:
  (i) hydrogen, $C_1$-$C_{12}$ alkyl, $C_2$-$C_{12}$ alkene, $C_2$-$C_{12}$ alkyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;
  (ii) phenyl that is mono-substituted at the para position with at least one substituent chosen from: $C_1$-$C_7$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_4$ alkyl substituted phenylene, mono- or poly-urethane ($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material;
  (iii) —CH(CN)$_2$ and —CH(COO$X_1$)$_2$, wherein X, is as set forth above;
  (iv) —CH($X_2$)($X_3$), wherein $X_2$ and $X_3$ are as set forth above;
  (v) an unsubstituted, mono-, di-, or tri-substituted aryl group, such as phenyl, naphthyl, phenanthryl, or pyrenyl; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl; wherein the substituents are independently chosen for each occurrence from:
    (A) a lengthening agent L represented by Formula I above;
    (B) —C(O)$X_6$, wherein $X_6$ is as set forth above;
    (C) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;
    (D) $C_1$-$C_{12}$ alkyl, $C_3$-$C_7$ cycloalkyl, $C_3$-$C_7$ cycloalkyoxy($C_1$-$C_{12}$)alkyl, aryl($C_1$-$C_{12}$)alkyl, aryloxy($C_1$-$C_{12}$)alkyl, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, haloalkyl, and mono($C_1$-$C_{12}$)alkoxy($C_1$-$C_{12}$)alkyl;
    (E) $C_1$-$C_{12}$ alkoxy, $C_3$-$C_7$ cycloalkoxy, cycloalkyloxy($C_1$-$C_{12}$)alkoxy, aryl($C_1$-$C_{12}$)alkoxy, aryloxy($C_1$-$C_{12}$)alkoxy, mono- or di-($C_1$-$C_{12}$)alkylaryl($C_1$-$C_{12}$)alkoxy, and mono- or di-($C_1$-$C_{12}$)alkoxyaryl ($C_1$-$C_{12}$)alkoxy;
    (F) amido, amino, mono- or di-alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;
    (G) —O$X_7$ and —N($X_7$)$_2$, wherein $X_7$ is as set forth above;
    (H) —S$X_{11}$, wherein $X_{11}$ is as set forth above;
    (I) a nitrogen containing ring represented by Formula i, which is set forth above; and
    (J) a group represented by one of Formula ii or iii, which are set forth above;
  (vi) an unsubstituted or mono-substituted group chosen from pyrazolyl, imidazolyi, pyrazolinyl, imidazolinyl, pyrrodlinyl, phenothiazinyl, phenoxazinyl, phenazinyl, or acridinyl, wherein each substituent is independently chosen from a lengthening agent L, $C_1$-$C_{12}$ alkyl, $C_1$-$C_{12}$ alkoxy, phenyl, hydroxy, amino or halogen;
  (vii) a group represented by one of Formula iv or v, which are set forth above;
  (viii) a group represented by Formula vi, which is set forth above; and
  (ix) a lengthening agent L represented by Formula I (above); and
(f) i is an integer chosen from 0 to the total available positions on A, and each $R^4$ is independently chosen for each occurrence from:
  (i) a lengthening agent L represented by Formula I; and
  (ii) a group represented by $R^1$;

provided the photochromic-dichroic compound represented by Formula XII comprises at least one lengthening agent (L) represented by Formula I above.

As discussed with respect to the photochromic-dichroic compounds set forth above, the photochromic-dichroic compounds generally represented by Formula XII can be extended at any available position by substitution with L or an $R^4$ group substituted with L, and/or in any desired direction by numerous combinations of substitutions of available positions with L or $R^4$ groups substituted with L. Thus, for example, although not limiting herein, the fulgides disclosed herein can be extended by selecting at least one of D, G, and at least one $R^4$ to be L or a group substituted with L, so as to enhance the average absorption ratio of the fulgide in at least the activated state. Further, although not limiting herein, as shown discussed in more detail below, when E is N—$R^5$, $R^5$ can be L or can be a group substituted with L. For example, according to one non-limiting embodiment, the photochromic-dichroic compound can be represented by Formula XIII:

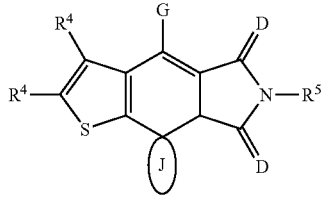

XIII wherein at least one of: $R^5$, G or $R^4$ is a lengthening agent L.

A general reaction sequence for synthesizing the photochromic-dichroic compounds that can be used in various non-limiting embodiments disclosed herein and that are represented by Formula XII above is depicted below in Reaction Sequence N. In Reaction Sequence N (below), an alicyclic ketone represented by Formula $v_1$ is reacted with dimethyl succinate represented by Formula $v_2$ in a Stobbe Condensation to produce the half-ester product represented by Formula $v_3$. The half-ester product represented by Formula $v_3$ is esterified to form the diester product represented by Formula $v_4$. The diester of Formula $v_4$ is reacted with a carbonyl-substituted A group represented by Formula $v_5$ in the Stobbe Condensation to produce the half-ester material represented by Formula $v_6$. As indicated Formula $v_5$, the carbonyl-substituted A group can also be substituted with one or more $R^4$ groups, each of which can comprise a lengthening agent L which is the same or different from the remaining L substituents. The half-ester material represented by Formula $v_7$ is hydrolyzed to produce the diacid material represented by Formula $v_7$. The diacid of Formula $v_7$ is reacted with acetyl chloride in an ether and/or tetrahydrofuran solvent to form the anhydride represented by Formula $v_8$.

As shown in Path (1) of Reaction Sequence N (below), the anhydride of Formula $v_8$ can be reacted with an amino substituted lengthening agent L and subsequently reacted with acetyl chloride under reflux conditions to produce the photochromic fulgimide compound represented by Formula $v_9$ according to one non-limiting embodiment disclosed herein. Alternatively, as shown in Path (2), the anhydride of Formula $v_8$ can be reacted with ammonia followed by acetyl chloride to produce the photochromic fulgide compound according to various non-limiting embodiments disclosed herein and represented by Formula $v_{10}$. Further, the photochromic fulgide compound of Formula $v_{10}$ can be further reacted with an appropriate reactant to form the photochromic fulgide compound of Formula $v_{11}$ according to various non-limiting embodiments disclosed herein, wherein the nitrogen is substituted with an $R^5$ group. Further, according to various non-limiting embodiments, the $R^5$ group can be a lengthening agent L, or can comprise a substituent group that is substituted with a lengthening agent L.

Reaction Sequence N

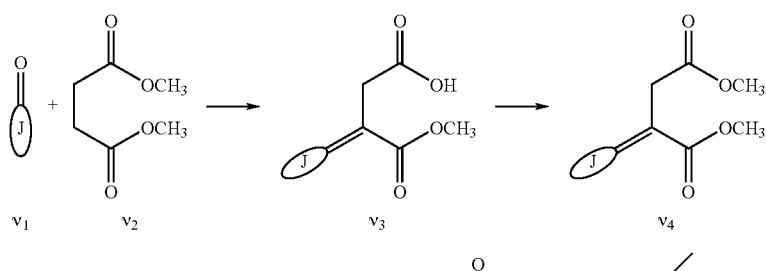

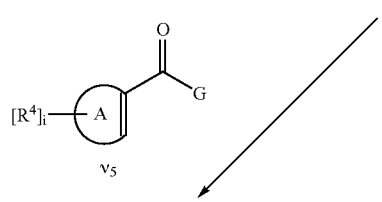

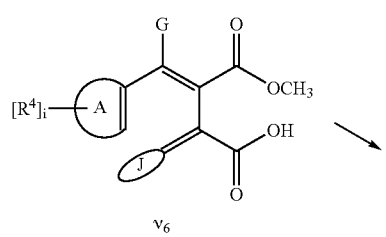

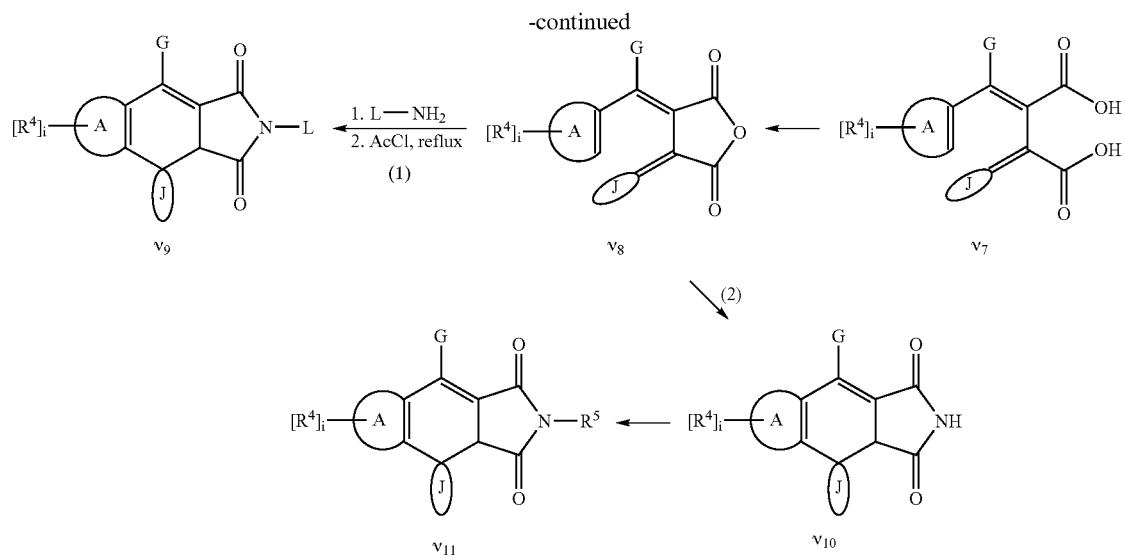

Reaction Sequences P, Q and T illustrate three general reaction schemes for substituting a lengthening agent L at various locations on a fulgide.

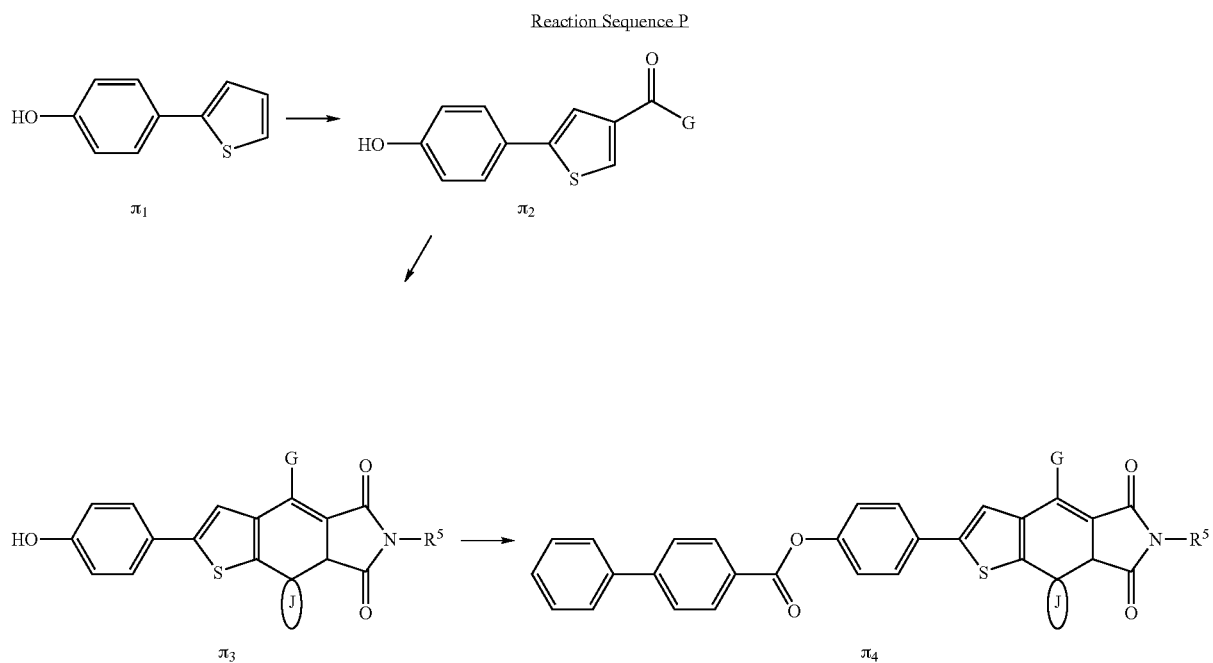

In Reaction Sequence P, the hydroxylated compound represented by Formula $\pi_1$ undergoes the Friedel-Crafts reaction to form the carbonyl-substituted group represented by Formula $\pi_2$. The material represented by Formula $\pi_2$ is reacted as described above for the material represented by Formula $v_5$ in Reaction Sequence N to form the hydroxyphenyl substituted thiophenofused fulgide represented by Formula $\pi_3$ in Reaction Sequence P. The fulgide represented by Formula $\pi_3$ is benzoylated with 4-phenylbenzoyl chloride to form the thermally reversible, photochromic compound according to one non-limiting embodiment disclosed herein and represented by Formula $\pi_4$. With additional reference to Formula XII above, as shown in Formula $\pi_4$, the A group is thiopheno that is substituted with a lengthening agent L. As previously discussed, according to various non-limiting embodiments (and as shown below in Reaction Sequence Q), the $R^5$ group in Formula $\pi_4$ can be a lengthening agent L, or can comprise another substituent group that is substituted with a lengthening agent L. Further, group G can also be a lengthening agent L or can be another substituent group that is substituted with a lengthening agent L (for example, as shown below in Reaction Sequence T).

Reaction Sequence Q

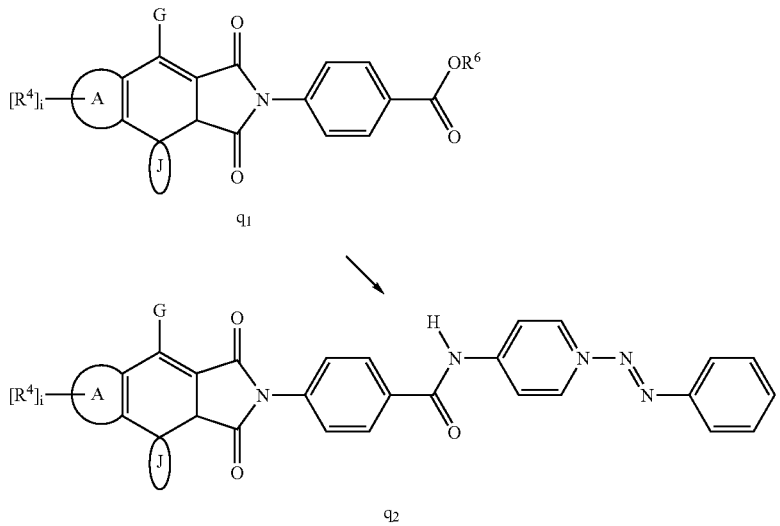

In Reaction Sequence Q, the fulgide represented by Formula $\theta_1$ can be made in accordance with Reaction Sequence N, with appropriate modifications that will be recognized by those skilled in the art. In Formula $\theta_1$, the $R^5$ group attached to the nitrogen atom is a methyl ester of para-amino benzoic acid. The methyl ester of para-amino benzoic acid is then reacted with 4-aminodiazobenzene, to form the thermally reversible, photochromic compound represented by Formula $\theta_2$ according to one non-limiting embodiment disclosed herein. As previously discussed, $R^5$ group can be a lengthening agent L or can be another substituent group that is substituted with L. Further, as previously discussed (and as depicted in Reaction Sequence P above) the A group of the thermally reversible, photochromic compound represented by Formula $\theta_2$, optionally can be substituted with one or more $R^4$ groups, each of which may comprise a lengthening agent L that is the same or different from the remaining L substituents. Further, as shown below in Reaction Sequence T (below), the G group in Formula $\theta_2$ can also be a lengthening agent L or can be another substituent group that is substituted with a lengthening agent L.

Reaction Sequence T

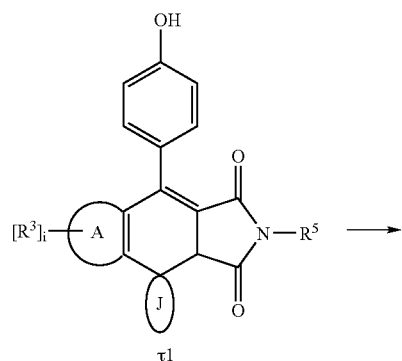

-continued

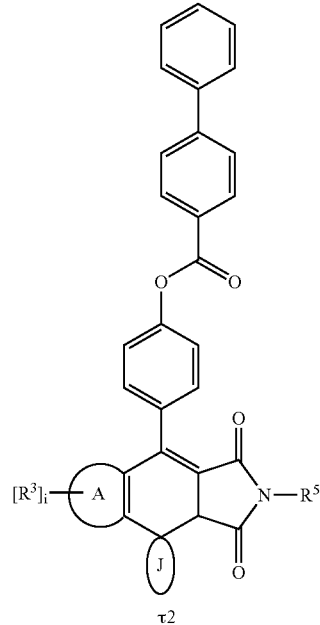

In Reaction Sequence T, the fulgide represented by Formula $\tau_1$ can be made in accordance with Reaction Sequence N, with appropriate modifications that will be recognized by those skilled in the art. The fulgide represented by formula $\tau_1$ can then be reacted with para-amino benzoylchloride to form the thermally reversible, photochromic compound according to one non-limiting embodiment disclosed herein and represented by Formula $\tau_2$. As previously discussed (and as depicted in Reaction Sequence Q above), the $R^5$ group of the thermally reversible, photochromic compound represented by Formula $\tau_2$ can be a lengthening agent L or can be another substituent group that is substituted with L. Further, as previously discussed (and as depicted in Reaction Sequence P above) the A group of the thermally reversible, photochromic compound represented by Formula $\tau_2$, optionally can be substituted with one or more $R^4$ groups, each of which may comprise a lengthening agent L that is the same or different from the remaining Ls.

As previously discussed, one non-limiting embodiment disclosed herein provides an optical element comprising a substrate and at least one at least partially aligned photochromic-dichroic compound connected to at least a portion of the substrate and having an average absorption ratio greater than 2.3 in an activated state as determined according to the CELL METHOD. Additionally, according to this non-limiting embodiment, the optical element can further comprise at least one orientation facility having a at least a first general direction connected to at least a portion of the substrate, and at least a portion of the at least one at least partially aligned photochromic-dichroic compound can be at least partially aligned by interaction with the orientation facility.

As used herein the term "orientation facility" means a mechanism that can facilitate the positioning of one or more other structures that are exposed, directly and/or indirectly, to at least a portion thereof. As used herein the term "order" means bring into a suitable arrangement or position, such as aligning with another structure or material, or by some other force or effect. Thus, as used herein the term "order" encompasses both contact methods of ordering a material, such as by aligning with another structure or material, and non-contact methods of ordering a material, such as by exposure to an external force or effect. The term order also encompasses combinations of contact and non-contact methods.

For example, in one non-limiting embodiment, the at least a portion of the at least one at least partially aligned photochromic-dichroic compound that is at least partially aligned by interaction with the at least one orientation facility can be at least partially aligned such that the long-axis of the photochromic-dichroic compound in the activated state is essentially parallel to at least the first general direction of the at least one orientation facility. According to another non-limiting embodiment, the at least a portion of the at least one at least partially aligned photochromic-dichroic compound that is at least partially aligned by interaction with at least a portion of the at least one orientation facility is bound to or reacted with the portion of the at least one orientation facility. As used herein with reference to order or alignment of a material or structure, the term "general direction" refers to the predominant arrangement or orientation of the material, compound or structure. Further, it will be appreciated by those skilled in the art that a material, compound or structure can have a general direction even though there is some variation within the arrangement of the material, compound or structure, provided that the material, compound or structure has at least one predominate arrangement.

As discussed above, the orientation facilities according to various non-limiting embodiments disclosed herein can have at least a first general direction. For example, the orientation facility can comprise a first ordered region having a first general direction and at least one second ordered region adjacent the first ordered region having a second general direction that is different from the first general direction. Further, the orientation facility can have a plurality of regions, each of which has a general direction that is the same or different from the remaining regions so as to form a desired pattern or design. Additionally, the at least one orientation facility can comprise one or more different types of orientation facilities. Non-limiting examples of orientation facilities that can be used in conjunction with this and other non-limiting embodiments disclosed herein include at least partial coatings comprising an at least partially ordered alignment medium, at least partially ordered polymer sheets, at least partially treated surfaces, Langmuir-Blodgeft films, and combinations thereof.

For example, although not limiting herein, according to one non-limiting embodiment, the orientation facility can comprise an at least partial coating comprising an at least partially ordered alignment medium. Non-limiting examples of suitable alignment media that can be used in conjunction with various non-limiting embodiments disclosed herein include photo-orientation materials, rubbed-orientation materials, and liquid crystal materials. Non-limiting methods of ordering at least a portion of the alignment medium are described herein below in detail.

As discussed above, according to various non-limiting embodiments, the alignment medium can be a liquid crystal material. Liquid crystal materials, because of their structure, are generally capable of being ordered or aligned so as to take on a general direction. More specifically, because liquid crystal molecules have rod- or disc-like structures, a rigid long axis, and strong dipoles, liquid crystal molecules can be ordered or aligned by interaction with an external force or another structure such that the long axis of the molecules takes on an orientation that is generally parallel to a common axis. For example, although not limiting herein, it is possible to align the molecules of a liquid crystal material with a magnetic field, an electric field, linearly polarized infrared radiation, linearly polarized ultraviolet radiation, linearly polarized visible radiation, or shear forces. It is also possible to align liquid crystal molecules with an oriented surface. That is, liquid crystal molecules can be applied to a surface that has been oriented, for example by rubbing, grooving, or photo-alignment methods, and subsequently aligned such that the long axis of each of the liquid crystal molecules takes on an orientation that is generally parallel to the general direction of orientation of the surface. Non-limiting examples of liquid crystal materials suitable for use as alignment media according to various non-limiting embodiments disclosed herein include liquid crystal polymers, liquid crystal pre-polymers, liquid crystal monomers, and liquid crystal mesogens. As used herein the term "pre-polymer" means partially polymerized materials.

Liquid crystal monomers that are suitable for use in conjunction with various non-limiting embodiments disclosed herein include mono- as well as multi-functional liquid crystal monomers. Further, according to various non-limiting embodiments disclosed herein, the liquid crystal monomer can be a cross-linkable liquid crystal monomer, and can further be a photocross-linkable liquid crystal monomer. As used herein the term "photocross-linkable" means a material, such as a monomer, a pre-polymer or a polymer, that can be cross-linked on exposure to actinic radiation. For example, photocross-linkable liquid crystal monomers include those liquid crystal monomers that are cross-linkable on exposure to ultraviolet radiation and/or visible radiation, either with or without the use of polymerization initiators.

Non-limiting examples of cross-linkable liquid crystal monomers suitable for use in accordance with various non-limiting embodiments disclosed herein include liquid crystal monomers having functional groups chosen from acrylates, methacrylates, allyl, allyl ethers, alkynes, amino, anhydrides, epoxides, hydroxides, isocyanates, blocked isocyanates, siloxanes, thiocyanates, thiols, urea, vinyl, vinyl ethers and blends thereof. Non-limiting examples of photocross-linkable liquid crystal monomers suitable for use in the at least partial coatings of the alignment facilities according to various non-limiting embodiments disclosed herein include liquid crystal monomers having functional groups chosen from acrylates, methacrylates, alkynes, epoxides, thiols, and blends thereof.

Liquid crystal polymers and pre-polymers that are suitable for use in conjunction with various non-limiting embodiments disclosed herein include main-chain liquid crystal polymers and pre-polymers and side-chain liquid crystal polymers and pre-polymers. In main-chain liquid crystal polymers and pre-polymers, rod- or disc-like liquid crystal mesogens are primarily located within the polymer backbone. In side-chain polymers and pre-polymers, the rod- or disc-like liquid crystal mesogens primarily are located within the side chains of the polymer. Additionally, according to various non-limiting embodiments disclosed herein, the liquid crystal polymer or pre-polymer can be cross-linkable, and further can be photocross-linkable.

Non-limiting examples of liquid crystal polymers and pre-polymers that are suitable for use in accordance with various non-limiting embodiments disclosed herein include, but are not limited to, main-chain and side-chain polymers and pre-polymers having functional groups chosen from acrylates, methacrylates, allyl, allyl ethers, alkynes, amino, anhydrides, epoxides, hydroxides, isocyanates, blocked isocyanates, siloxanes, thiocyanates, thiols, urea, vinyl, vinyl ethers, and blends thereof. Non-limiting examples of photocross-linkable liquid crystal polymers and pre-polymers that are suitable for use in the at least partial coatings of the alignment facilities according to various non-limiting embodiments disclosed herein include those polymers and pre-polymers having functional groups chosen from acrylates, methacrylates, alkynes, epoxides, thiols, and blends thereof.

Liquid crystals mesogens that are suitable for use in conjunction with various non-limiting embodiments disclosed herein include thermotropic liquid crystal mesogens and lyotropic liquid crystal mesogens. Further, non-limiting examples of liquid crystal mesogens that are suitable for use in conjunction with various non-limiting embodiments disclosed herein include columatic (or rod-like) liquid crystal mesogens and discotic (or disc-like) liquid crystal mesogens.

Non-limiting examples of photo-orientation materials that are suitable for use as an alignment medium in conjunction with various non-limiting embodiments disclosed include photo-orientable polymer networks. Specific non-limiting examples of suitable photo-orientable polymer networks include azobenzene derivatives, cinnamic acid derivatives, coumarine derivatives, ferulic acid derivatives, and polyimides. For example, according to one non-limiting embodiment, the orientation facility can comprise at least one at least partial coating comprising an at least partially ordered photo-orientable polymer network chosen from azobenzene derivatives, cinnamic acid derivatives, coumarine derivatives, ferulic acid derivatives, and polyimides. Specific non-limiting examples of cinnamic acid derivatives that can be used as an alignment medium in conjunction with various non-limiting embodiments disclosed herein include polyvinyl cinnamate and polyvinyl esters of paramethoxycinnamic acid.

As used herein the term "rubbed-orientation material" means a material that can be at least partially ordered by rubbing at least a portion of a surface of the material with another suitably textured material. For example, although not limiting herein, in one non-limiting embodiment, the rubbed-orientation material can be rubbed with a suitably textured cloth or a velvet brush. Non-limiting examples of rubbed-orientation materials that are suitable for use as an alignment medium in conjunction with various non-limiting embodiments disclosed herein include (poly)imides, (poly)siloxanes, (poly)acrylates, and (poly)coumarines. Thus, for example, although not limiting herein, the at least partial coating comprising the alignment medium can be an at least partial coating comprising a polyimide that has been rubbed with velvet or a cloth so as to at least partially order at least a portion of the surface of the polyimide.

As discussed above, the at least one orientation facility according to certain non-limiting embodiments disclosed herein can comprise an at least partially ordered polymer sheet. For example, although not limiting herein, a sheet of polyvinyl alcohol can be at least partially ordered by stretching the sheet, and there after the sheet can be bonded to the at least a portion a surface of the optical substrate to form the orientation facility. Alternatively, the ordered polymer sheet can be made by a method that at least partially orders the polymer chains during fabrication, for example and without limitation, by extrusion. Further, the at least partially ordered polymer sheet can be formed by casting or otherwise forming a sheet of a liquid crystal material and thereafter at least partially ordering the sheet for example, but exposing the sheet to at least one of a magnetic field, an electric field, or a shear force. Still further, the at least partially ordered polymer sheet can be made using photo-orientation methods. For example and without limitation, a sheet of a photo-orientation material can be formed, for example by casting, and thereafter at least partially ordered by exposure to linearly polarized ultraviolet radiation. Still other non-limiting methods of forming at least partially ordered polymer sheets are described herein below.

Still further, the orientation facilities according to various non-limiting embodiments disclosed herein can comprise an at least partially treated surface. As used herein, the term "treated surface" refers to at least a portion of a surface that has been physically altered to create at least one ordered region on least a portion of the surface. Non-limiting examples of at least partially treated surfaces include at least partially rubbed surfaces, at least partially etched surfaces, and at least partially embossed surfaces. Further, the at least partially treated surfaces can be patterned, for example using a photolithographic or an interferographic process. Non-limiting examples of at least partially treated surfaces that are useful in forming the orientation facilities according to various non-limiting embodiments disclosed herein include, chemically etched surfaces, plasma etched surfaces, nano-etched surfaces (such as surfaces etched using a scanning tunneling microscope or an atomic force microscope), laser etched surfaces, and electron-beam etched surfaces.

In one specific non-limiting embodiment, wherein the orientation facility comprises an at least partially treated surface, imparting the orientation facility can comprise depositing a metal salt (such as a metal oxide or metal fluoride) onto at least a portion of a surface, and thereafter etching the deposit to form the orientation facility. Non-limiting examples of suitable techniques for depositing a metal salt include plasma vapor deposition, chemical vapor deposition, and sputtering. Non-limiting examples of etching processes are set forth above.

As used herein the term "Langmuir-Blodgett films" means one or more at least partially ordered molecular films on a surface. For example, although not limiting herein, a Langmuir-Blodgett film can be formed by dipping a substrate into a liquid one or more times so that it is at least partially covered by a molecular film and then removing the substrate from the liquid such that, due to the relative surface tensions of the liquid and the substrate, the molecules of the molecular film are at least partially ordered in a general direction. As used herein, the term molecular film refers to monomolecular films (i.e., monolayers) as well as films comprising more than one monolayer.

In addition to the orientation facilities described above, the optical elements according to various non-limiting embodiments disclosed herein can further comprise at least one at least partial coating comprising an at least partially ordered alignment transfer material interposed between the at least one orientation facility and the photochromic-dichroic compound (or at least partial coating comprising the same). Still further, the optical elements can comprise a plurality of at least partial coatings comprising an alignment transfer interposed between the at least one orientation facility and the photochromic-dichroic compound. For example, although not limiting herein, the optical element can comprise at least one orientation facility comprising an at least partial coating comprising an at least partially ordered alignment medium connected to at least a portion of the optical substrate, and at least one at least partial coating comprising an at least partially ordered alignment transfer material connected to at least a portion of the orientation facility. Further, according to this non-limiting embodiment, the at least one photochromic-dichroic compound can be at least partially aligned by interaction with the at least partially ordered alignment transfer material. More specifically, although not limiting herein, in one non-limiting embodiment, at least a portion of the alignment transfer material can be aligned by interaction with at least a portion of the at least partially ordered alignment medium, and at least a portion of the at least one photochromic-dichroic compound can be aligned by interaction with the at least a partially aligned portion of the alignment transfer material. That is, the alignment transfer material can facilitate the propagation or transfer of a suitable arrangement or position from the orientation facility to the at least one photochromic-dichroic compound.

Non-limiting examples of alignment transfer materials that are suitable for use in conjunction with various non-limiting embodiments disclosed herein include, without limitation, those liquid crystal materials described above in connection with the alignment media disclosed herein. As previously discussed, it is possible to align the molecules of a liquid crystal material with an oriented surface. That is, a liquid crystal material can be applied to a surface that has been oriented and subsequently aligned such that the long axis of the liquid crystal molecules takes on an orientation that is generally parallel to the general direction of orientation of the surface. Thus, according to various non-limiting embodiments disclosed herein wherein the alignment transfer material comprises a liquid crystal material, the liquid crystal material can be at least partially ordered by aligning the at least a portion of the liquid crystal material with at least a portion of the orientation facility such that the long axis of the molecules of at least a portion of the liquid crystal material are generally parallel to at least a first general direction of the orientation facility. In this manner, the general direction of the orientation facility can be transferred to the liquid crystal material, which in turn can transfer the general direction to another structure or material. Further, if the at least one orientation facility comprises a plurality of regions having general directions that together form a design or pattern (as previously described), that design or pattern can be transferred to the liquid crystal material by aligning the liquid crystal material with the various regions of the orientation facility as discussed above. Additionally, although not required, according to various non-limiting embodiments disclosed herein, at least a portion of the liquid crystal material can be exposed to at least one of: a magnetic field, an electric field, linearly polarized infrared radiation, linearly polarized ultraviolet radiation, and linearly polarized visible radiation while being at least partially aligned with at least a portion of the orientation facility.

Still further, in addition to the at least one at least partially aligned photochromic-dichroic compound connected to the at least a portion of the substrate, the optical element according to various non-limiting embodiments disclosed herein can comprise at least one at least partially ordered anisotropic material connected to the at least a portion of the at least one surface of the substrate. That is, according to certain non-limiting embodiments the optical element comprises a substrate, at least one at least partially aligned photochromic-dichroic compound connected to at least a portion of the substrate, the at least one photochromic-dichroic compound having an average absorption ratio greater than 2.3 in an activated state as determined according to the CELL METHOD, and at least one at least partially ordered anisotropic material connected to the at least a portion of the at least one surface of the substrate.

As used herein the term "anisotropic" means having at least one property that differs in value when measured in at least one different direction. Thus, "anisotropic materials" are materials that have at least one property that differs in value when measured in at least one different direction. Non-limiting examples of anisotropic materials that are suitable for use in conjunction with various non-limiting embodiments disclosed herein include, without limitation, those liquid crystal materials described above.

According to various non-limiting embodiments, at least a portion of the at least one at least partially aligned photochromic-dichroic compound can be at least partially aligned by interaction with the at least one at least partially ordered anisotropic material. For example, although not limiting herein, at least a portion of the at least one photochromic-dichroic compound can be aligned such that the long-axis of the photochromic-dichroic compound in the dichroic state is essentially parallel to the general direction of the anisotropic material. Further, although not required, the at least one photochromic-dichroic compound can be bound to or reacted with at least a portion of the at least one at least partially ordered anisotropic material.

Further, according to various non-limiting embodiments disclosed herein, the at least one at least partially aligned photochromic-dichroic compound and the at least one at least partially ordered anisotropic material can be present as an least partial coating on at least a portion of the substrate. For example, according to one non-limiting embodiment, the at least one at least partially ordered anisotropic material can be a liquid crystal material, and the at least one at least partially aligned photochromic-dichroic compound and the at least one at least partially ordered anisotropic material can be present as an least partial liquid crystal coating on at least a portion of the substrate. According to another non-limiting embodiment, the at least partial coating can be a phase-separated polymer coating comprising a matrix phase and a guest phase distributed in the matrix phase. Although not limiting herein, according to this non-limiting embodiment, the matrix phase can comprise an at least partially ordered liquid crystal polymer. Further, according to this non-limiting embodiment, guest phase can comprise the at least partially ordered anisotropic material and at least a portion of the at least one at least partially aligned photochromic-dichroic compound. Still further, as discussed above, the at least one at least partially aligned photochromic-dichroic compound can be at least partially aligned by interaction with the at least partially ordered anisotropic material.

In another non-limiting embodiment, the at least partial coating can comprise an interpenetrating polymer network. According to this non-limiting embodiment, the at least one at least partially ordered anisotropic material and a polymeric material can form an interpenetrating polymer network, wherein at least a portion of the polymeric material interpenetrates with at least a portion of the at least partially ordered anisotropic material. As used herein the term "interpenetrating polymer network" means an entangled combination of polymers, at least one of which is cross-linked, that are not bonded to each other. Thus, as used herein, the term interpenetrating polymer network includes semi-interpenetrating polymer networks. For example, see L. H. Sperling, *Introduction to Physical Polymer Science*, John Wiley & Sons, New York (1986) at page 46. Further, according to this non-limiting embodiment, at least a portion of the at least one at least partially aligned photochromic-dichroic compound can be at least partially aligned with the at least partially ordered anisotropic material. Still further, according to this non-limiting embodiment, the polymeric material can be isotropic or anisotropic, provided that, on the whole, the at least partial coating is anisotropic. Methods of forming such at least partial coatings are described in more detail herein below.

Still other non-limiting embodiments disclosed herein provide an optical element comprising a substrate, at least one at least partially ordered orientation facility connected to at least a portion of the substrate, and an at least partial coating connected to at least a portion of the at least partially ordered orientation facility, the at least partial coating comprising at least one anisotropic material that is at least partially aligned with at least a portion of the at least partially ordered orientation facility and at least one photochromic-dichroic compound that is at least partially aligned with at least a portion of the at least partially aligned anisotropic material.

As previously discussed, the orientation facilities according to various non-limiting embodiments disclosed herein can comprise a first ordered region having a first general direction and at least one second ordered region adjacent the first region having a second general direction that is different from the first general direction. Further, the orientation facility can comprise multiple ordered regions having multiple general directions that together create a specific design or pattern. Non-limiting examples of orientation facilities that are suitable for use in conjunction with this non-limiting embodiment are described above in detail. Additionally, according to various non-limiting embodiment disclosed herein, an at least partial coating comprising an alignment transfer material can be positioned between the at least one orientation facility and the at least partial coating comprising the anisotropic material and the at least one photochromic-dichroic compound. Further, the general direction or pattern of the at least one orientation facility can be transferred to the alignment transfer material by alignment, which, in turn, can transfer the general direction of the orientation facility to the at least partial coating comprising the anisotropic material and the at least one photochromic-dichroic compound by alignment. That is, the anisotropic material of the at least partial coating can be at least partially aligned with the at least partially aligned alignment transfer material. Further, the at least one photochromic-dichroic compound can be at least partially aligned by interaction with the at least partially aligned anisotropic material.

Further, according to various non-limiting embodiments disclosed herein, the at least one anisotropic material can be adapted to allow the at least one photochromic-dichroic compound to switch from a first state to the second state at a desired rate. Generally speaking conventional photochromic compounds can undergo a transformation from one isomeric form to another in response to actinic radiation, with each isomeric form having a characteristic absorption spectrum. The photochromic-dichroic compounds according to various non-limiting embodiments disclosed herein undergo a similar isomeric transformation. The rate or speed at which this isomeric transformation (and the reverse transformation) occurs depends, in part, upon the properties of the local environment surrounding the photochromic-dichroic compound (that is, the "host"). Although not limiting herein, it is believed by the inventors the rate of transformation of the photochromic-dichroic compound will depend, in part, upon the flexibility of the chain segments of the host, that is, the mobility or viscosity of the chain segments of the host. In particular, while not limiting herein, it is believed that the rate of transformation of the photochromic-dichroic compound will generally be faster in hosts having flexible chain segments than in host having stiff or rigid chain segments. Therefore, according to certain non-limiting embodiments disclosed herein, wherein the anisotropic material is a host, the anisotropic material can be adapted to allow the photochromic-dichroic compound to transform between various isomeric states at desired rates. For example, although not limiting herein, the anisotropic material can be adapted by adjusting one or more of the molecular weight and the cross-link density of the anisotropic material.

According to another non-limiting embodiment, the at least partial coating comprising at least one anisotropic material and at least one photochromic-dichroic compound can be a phase-separated polymer coating comprising matrix phase, for example and without limitation, a liquid crystal polymer, and guest phase distributed within the matrix phase. Further, according to this non-limiting embodiment, the guest phase can comprise the anisotropic material. Still further, according to this non-limiting embodiment, the majority of the at least one photochromic-dichroic compound can be contained within the guest phase of the phase-separated polymer coating. As previously discussed, because the transformation rate of the at least one photochromic-dichroic compound depends, in part, on the host in which it is contained, according to this non-limiting embodiment, the rate of transformation of the at least one photochromic-dichroic compound will depend, largely, on the properties of the guest phase.

For example, one non-limiting embodiment provides an optical element comprising a substrate, at least one orientation facility connected to at least a portion of a surface of the substrate, and an at least partial coating connected to at least a portion of the at least one orientation facility and comprising a phase-separated polymer. According to this non-limiting embodiment, the phase-separated polymer can comprise a matrix phase, at least a portion of which is at least partially aligned with at least portion of the at least one orientation facility, and a guest phase comprising an anisotropic material dispersed within the matrix phase. Further according to this non-limiting embodiment, at least a portion of the anisotropic material of the guest phase can be at least partially aligned with at least portion of the at least one orientation facility and at least one photochromic-dichroic compound can be at least partially aligned with at least a portion of the anisotropic material. Still further, according to various non-limiting embodiments disclosed herein, the matrix phase of the phase-separated polymer can comprise a liquid crystal polymer, and the anisotropic material of the guest phase can be chosen from liquid crystal polymers and liquid crystal mesogens. Non-limiting examples of such materials are set forth in detail above. Additionally, while not limiting herein, according to this non-limiting embodiment, the at least partial coating comprising the phase-separated polymer can be substantially haze-free. Haze is defined as the percentage of transmitted light that deviates from the incident beam by more than 2.5 degrees on average according to ASTM D 1003 Standard Test Method of Haze and Luminous Transmittance of Transparent Plastics. An example of an instrument on which haze measurements according to ASTM D 1003 can be made is Haze-Gard Plus™ made by BYK-Gardener.

Further, although not limiting herein, according to other non-limiting embodiments the at least one photochromic-dichroic compound can be encapsulated or coated with an at least partially ordered host material and then the encapsulated or coated photochromic-dichroic compound can be dispersed within another material. For example, although not limiting herein, the at least one photochromic-dichroic compound can be encapsulated or overcoated with an at least partially ordered anisotropic material having relatively flexible chain segments, such as an at least partially ordered liquid crystal material, and thereafter dispersed or distributed in another material having relatively rigid chain segments. For example, the encapsulated photochromic-dichroic compound can be dispersed or distributed in a liquid crystal polymer having relatively rigid chain segments and thereafter the mixture can be applied to a substrate to form a coating.

According to still another non-limiting embodiment, the at least partial coating comprising at least one anisotropic material and at least one photochromic-dichroic compound can be interpenetrating polymer network coating. For example, the at least partial coating can comprise a polymeric material that interpenetrates with at least a portion of the at least one anisotropic material, and at least a portion of the at least one photochromic-dichroic compound can be at least partially aligned with the at least partially aligned anisotropic material. Methods of forming such interpenetrating network coatings are described below in more detail.

Still other non-limiting embodiments disclosed herein provide an optical element comprising a substrate, a first at least partial coating comprising an at least partially ordered alignment medium connected to at least a portion of at least one surface of the substrate, a second at least partial coating comprising an alignment transfer material connected to and at least partially aligned with at least a portion of the at least partially ordered alignment medium, and a third at least partial coating connected to at least a portion of the at least partially ordered alignment transfer material, the third at least partial coating comprising at least one anisotropic material that is at least partially aligned with at least a portion of the at least partially aligned alignment transfer material and at least one photochromic-dichroic compound that is at least partially aligned with at least a portion of the at least partially aligned anisotropic material.

Although not limiting herein, according to various non-limiting embodiments, the first at least partial coating comprising the at least partially ordered alignment medium can have a thickness that varies widely depending upon the final application and/or the processing equipment employed. For example, in one non-limiting embodiment, the thickness of the at least partial coating comprising the at least partially ordered alignment medium can range from at least 0.5 nanometers to 10,000 nanometers. In another non-limiting embodiment, the at least partial coating comprising the at least partially ordered alignment medium can have a thickness ranging from at least 0.5 nanometers to 1000 nanometers. In still another non-limiting embodiment, the at least partial coating comprising the at least partially ordered alignment medium can have a thickness ranging from at least 2 nanometers to 500 nanometers. In yet another non-limiting embodiment, the at least partial coating comprising the at least partially ordered alignment medium can have a thickness ranging from 100 nanometers to 500 nanometers. Additionally, according to various non-limiting embodiments, the optical element can comprise a plurality of at least partial coatings comprising an at least partially ordered alignment medium. Further each of the plurality of at least partial coatings can have the same or a different thickness as the other at least partial coatings of the plurality.

Further, according to various non-limiting embodiments disclosed herein, the second at least partial coating comprising the alignment transfer material can have a thickness that varies widely depending upon the final application and/or the processing equipment employed. For example, in one non-limiting embodiment, the thickness of the at least partial coating comprising the at least partially ordered alignment transfer material can range from 0.5 microns to 1000 microns. In another non-limiting embodiment, the at least partial coating comprising the at least partially ordered alignment transfer material can have a thickness ranging from 1 to 25 microns. In still another non-limiting embodiment, the at least partial coating comprising the at least partially ordered alignment transfer material can have a thickness ranging from 5 to 20 microns. Additionally, according to various non-limiting embodiments, the optical element can comprise a plurality of at least partial coatings comprising an alignment transfer material. Further each of the plurality of at least partial coatings can have the same or a different thickness as the other at least partial coatings of the plurality.

Still further, according to various non-limiting embodiments disclosed herein, the third at least partial coating comprising the anisotropic material and the at least one photochromic-dichroic compound can have a thickness that varies widely depending upon the final application and/or the processing equipment employed. In one non-limiting embodiment, the at least partial coating comprising the at least partially aligned anisotropic material and the at least one photochromic-dichroic compound can have a thickness of at least 0.5 microns to 1000 microns. According to other non-limiting embodiments, the third at least partial coating can have a thickness ranging from 1 micron to 25 microns. According to still other non-limiting embodiments, the third at least partial coating can have a thickness ranging from 5 microns to 20 microns. Additionally, according to various non-limiting embodiments, the optical element can comprise a plurality of at least partial coatings comprising an at least partially aligned anisotropic material and at least one dichroic material. Further each of the plurality of at least partial coatings can have the same or a different thickness as the other at least partial coatings of the plurality. Non-limiting examples of suitable photochromic-dichroic compounds are described above in detail.

Further, according to various non-limiting embodiments, in addition to the third at least partial coating, either or both of the first and second at least partial coatings can comprise photochromic-dichroic compounds that are the same or different from the photochromic-dichroic compounds of the third at least partial coating. Still further, according to various non-limiting embodiments, any of the at least partial coatings described above can further comprise at least one additive, at least one conventional dichroic compound and/or at least one conventional photochromic compound. Non-limiting examples of suitable additives, conventional dichroic compounds, and conventional photochromic compounds are set forth above. Further, as previously discussed, in addition to the first, second, and third at least partial coatings described above, the optical elements according to various non-limiting embodiments disclosed herein can further comprise primer coatings, anti-reflective coatings, photochromic coatings, linearly polarizing coatings, circularly polarizing coatings, elliptically polarizing coatings, transitional coatings, and protective coatings. Non-limiting examples of such coatings are provided above.

Other non-limiting embodiments disclosed herein provide a composite optical element comprising a substrate, an at least partially ordered polymeric sheet connected to at least a portion of the substrate, and at least one at least partially aligned photochromic-dichroic compound connected to at least a portion of the at least partially ordered polymeric sheet and having an average absorption ratio greater than 2.3 in an activated state as determined according to the CELL METHOD. For example, although not limiting herein, according to one non-limiting embodiment a stretched polymer sheet containing at least one photochromic-dichroic compound that is at least partially aligned by the oriented polymer chains of the stretched polymer sheet can be connected to at least a portion of the substrate.

Further, according to various non-limiting embodiments, the composite optical element can comprise a plurality of polymeric sheets, at least one of which is at least partially ordered, connected to at least a portion of the substrate. For example, although not limiting herein, the composite optical element can comprise a substrate and an at least partially ordered polymeric sheet comprising at least one at least partially aligned photochromic-dichroic compound that interposed between to dimensionally stable or "rigid" polymer sheets connected to at least a portion of the substrate. According to other non-limiting embodiments, the composite optical element can comprise two or more at least partially ordered polymeric sheets comprising an at least partially aligned photochromic-dichroic compound that are connected to at least a portion of the substrate. Further, the two or more at least partially ordered polymeric sheets can have the same general direction or different general directions and can comprise the same photochromic-dichroic compound or different photochromic-dichroic compounds. Still further, the at least two at least partially ordered polymeric sheets can be stacked or layered on the substrate or they can be positioned adjacent each other on the substrate.

Examples of at least partially ordered polymeric sheets that can be used in conjunction with this non-limiting embodiment include, without limitation, stretched polymer sheets, ordered liquid crystal polymer sheets, and photo-oriented polymer sheets. Examples of polymeric materials, other than liquid crystal materials and photo-orientation materials that can be used in forming polymeric sheets according to various non-limiting embodiments disclosed herein include without limitation: polyvinyl alcohol, polyvinyl chloride, polyurethane, polyacrylate, and polycaprolactam. Non-limiting examples of methods of at least partially ordering polymeric sheets are described below in more detail.

Still other non-limiting embodiments disclosed herein provide a composite optical element comprising a substrate and at least one sheet connected to at least a portion of the substrate, the at least one sheet comprising: an at least partially ordered liquid crystal polymer having at least a first general direction, at least one at least partially ordered liquid crystal material having at least a second general direction distributed within at least a portion of the liquid crystal polymer, and at least one photochromic-dichroic compound that is at least partially aligned with at least a portion of the at least one at least partially ordered liquid crystal material, wherein at least the second general direction is generally parallel to at least the first general direction.

Non-limiting embodiments of methods of making optical elements and devices will now be described. One non-limiting embodiment provides a method of making an optical element comprising forming an at least partial coating comprising at least one at least partially aligned photochromic-dichroic compound on at least a portion of a substrate. As used herein the term "on" means in direct contact with an object (such as a substrate) or in indirect contact with the object through one or more other coatings or structures, at least one of which is in direct contact with the object. Further, according to this non-limiting embodiment, in addition to the at least one at least partially aligned photochromic-dichroic compound, at least one at least partially ordered anisotropic material can be connected to at least a portion of the substrate.

According to this non-limiting embodiment, the at least partial coating can have an average absorption ratio of at least 1.5. Further, according to this and other non-limiting embodiments of methods of making elements and devices disclosed herein, the at least one at least partially aligned photochromic-dichroic compound can have an average absorption ratio greater than 2.3 in an activated state as determined according to the CELL METHOD. Non-limiting examples of photochromic-dichroic compounds that are useful in conjunction with the methods of making elements and devices disclosed herein are set forth above in detail.

According to various non-limiting embodiments disclosed herein, forming the at least partial coating comprising the at least one at least partially aligned photochromic-dichroic compound can comprise applying the at least one photochromic-dichroic compound and at least one anisotropic material to at least a portion of the substrate, at least partially ordering at least a portion of the at least one anisotropic material, and at least partially aligning at least a portion of the at least one photochromic-dichroic compound with at least a portion of the at least partially ordered anisotropic material. Non-limiting methods of applying the at least one photochromic-dichroic compound and the at least one anisotropic material to the substrate that can be used in conjunction with the methods according to various non-limiting embodiments disclosed herein include, but are not limited to, spin coating, spray coating, spray and spin coating, curtain coating, flow coating, dip coating, injection molding, casting, roll coating, wire coating, and overmolding.

According to other non-limiting embodiments, applying the at least one photochromic-dichroic compound and at least one anisotropic material to at least a portion of the substrate can comprise forming an at least partial coating of the anisotropic material on at least a portion of a mold, which may be treated with a release material. Thereafter, at least a portion of the at least one anisotropic material can be at least partially ordered (as discussed in more detail below) and at least partially set. Thereafter, the substrate can be formed over the at least partial coating (i.e., overmolding), for example, by casting the substrate forming material in the mold. The substrate forming material can then be at least partially set to form the substrate. Subsequently, the substrate and the at least partial coating of the at least partially ordered anisotropic material can be released from the mold. Further, according to this non-limiting embodiment, the at least one photochromic-dichroic compound can be applied to the mold with the anisotropic material, or it can be imbibed into the anisotropic material after the anisotropic material has been applied to the mold, after the anisotropic material has been at least partially ordered, or after the substrate with the at least partial coating of the ordered anisotropic material has been released from the mold.

According to other non-limiting embodiments disclosed herein, forming the at least partial coating comprising the at least one at least partially aligned photochromic-dichroic compound can comprise applying at least one anisotropic material to at least a portion of the substrate, imbibing at least one photochromic-dichroic compound into at least a portion of the at least one anisotropic material, at least partially ordering at least a portion of the at least one anisotropic material, and at least partially aligning at least a portion of the at least one photochromic-dichroic compound with at least a portion of the at least partially ordered anisotropic material. Non-limiting methods of imbibing photochromic-dichroic compounds into various coatings are described herein below in more detail.

Non-limiting methods of ordering the anisotropic material include exposing the anisotropic material to at least one of a magnetic field, an electric field, linearly polarized ultraviolet radiation, linearly polarized infrared radiation, linearly polarized visible radiation, and a shear force. Further, the at least one anisotropic material can be at least partially ordered by aligning at least a portion of the anisotropic material with another material or structure. For example, although not limiting herein, the at least one anisotropic material can be at least partially ordered by aligning the anisotropic material with an orientation facility-such as, but not limited to, those orientation facilities previously discussed.

As previously described, by ordering at least a portion of the at least one anisotropic material, it is possible to at least partially align at least a portion of the at least one photochromic-dichroic compound that contained within or otherwise connected to the anisotropic material. Although not required, the at least one photochromic-dichroic compound can be at least partially aligned while in an activated state. Further, according to various non-limiting embodiments disclosed herein, applying the at least one photochromic-dichroic compound and the at least one anisotropic material to the portion of the substrate can occur at essentially the same time as, prior to, or after ordering the at least one anisotropic material and/or aligning the at least one photochromic-dichroic compound.

For example, according to one non-limiting embodiment applying the at least one photochromic-dichroic compound and that the at least one anisotropic material can occur at essentially the same time as ordering at least a portion of the at least one anisotropic material and aligning at least a portion of the at least one photochromic-dichroic compound. More particularly, according to this limiting embodiment, the at least one photochromic-dichroic compound and at least one anisotropic material can be applied to at least a portion of the substrate using a coating technique that can introduce a shear force to at least a portion of the anisotropic material during application such that at least a portion of the at least one anisotropic material can be at least partially ordered generally parallel to the direction of the applied shear force. For example, although not limiting herein, a solution or mixture (optionally in a solvent or carrier) of the at least one photochromic-dichroic compound and the at least one anisotropic material can be curtain coated on to the at least a portion of the substrate such that shear forces are introduced to the materials being applied due to relative movement of the surface of the substrate with respect to the materials being applied. The shear forces can cause at least a portion of the at least one anisotropic material to be ordered in a general direction that is essentially parallel to the direction of the movement of the surface. As discussed above, by ordering at least a portion of the at least one anisotropic material in this manner, at least a portion of the at least one photochromic-dichroic compound which is contained within or connected to the anisotropic material can be aligned by at least a portion of the at least partially ordered anisotropic material. Further, although not required, by exposing at least a portion of the at least one photochromic-dichroic compound to actinic radiation during the curtain coating process, such that at least a portion of the at least one photochromic-dichroic compound is in an activated state, at least partial alignment of the at least one photochromic-dichroic compound while in the activated state can be achieved.

In another non-limiting embodiment wherein the at least one photochromic-dichroic compound and the at least one anisotropic material are applied to the portion of the substrate prior to ordering at least a portion of the at least one anisotropic material and aligning at least a portion of the at least one photochromic-dichroic compound, applying the materials can comprise spin coating a solution or mixture of the at least one photochromic-dichroic compound and at least one anisotropic material (optionally in a solvent or carrier) onto at least a portion of at least one surface of the substrate. Thereafter, according to this non-limiting embodiment, at least a portion of the at least one anisotropic material can be at least partially ordered, for example, by exposing at least a portion of the at least one anisotropic material to a magnetic field, an electric field, linearly polarized ultraviolet radiation, linearly polarized infrared radiation, linearly polarized visible radiation, or a shear force. Further at least a portion of the at least one anisotropic material can be at least partially ordered by aligning the at least a portion with another material or structure, for example, an orientation facility In still another non-limiting embodiment, wherein at least a portion of the at least one photochromic-dichroic compound is at least partially aligned and the at least one anisotropic material is at least partially ordered prior to being applied to at least a portion of the substrate, a solution or mixture (optionally in a solvent or carrier) of the at least one photochromic-dichroic compound and the at least anisotropic material can be applied to an ordered polymeric sheet to form an at least partial coating. Thereafter, at least a portion of the at least one anisotropic material can be allowed to align with at least a portion of the ordered polymeric sheet. The polymeric sheet can be subsequently applied to at least a portion of the substrate by, for example, but not limited to, laminating or bonding. Alternatively, the coating can be transferred from the polymeric sheet to the substrate by methods known in the art, such as, but not limited to hot stamping. Other methods of applying polymeric sheets are described herein in more detail.

In another non-limiting embodiment, applying the at least one photochromic-dichroic compound and at least one anisotropic material to at least a portion of the substrate can comprise applying a phase-separating polymer system comprising a matrix phase forming material comprising a liquid crystal material and a guest phase forming material comprising the at least one anisotropic material and at least one photochromic-dichroic compound. After applying the phase-separating polymer system, according to this non-limiting embodiment, at least portion of the liquid crystal material of matrix phase and at least a portion of the anisotropic material of the guest phase are at least partially ordered, such that at least a portion of the at least one photochromic-dichroic compound is aligned with at least a portion of the at least partially ordered anisotropic material of the guest phase. Non-limiting methods of at least partially ordering at least portion of the of the matrix phase forming material and at least a portion of the guest phase forming material of the phase-separating polymer system include exposing at least a portion of the at least partial coating comprising the phase-separating polymer system to at least one of: a magnetic field, an electric field, linearly polarized infrared radiation, linearly polarized ultraviolet radiation, linearly polarized visible radiation, and a shear force. Further, at least partially ordering at least a portion of the matrix phase forming material and at least a portion of the guest phase forming material can comprise at least partially aligning at the portions with an orientation facility, as described in more detail below.

After at least partially ordering at least a portion of the matrix phase forming material and the guest phase forming material, at least a portion of the guest phase forming material can be separated from at least a portion of the matrix phase forming material by at least one of polymerization induced phase separation and solvent induced phase separation. Although for clarity the separation of the matrix and guest phase forming materials is described herein in relation to the guest phase forming material separating from the matrix phase forming material, it should be appreciated that this language is intended to cover any separation between the two phase forming materials. That is, this language is intended to cover separation of the guest phase forming material from the matrix phase forming material and separation of the matrix phase forming material from the guest phase forming material, as well as, simultaneous separation of both phase forming materials and any combination thereof.

According to various non-limiting embodiments disclosed herein, the matrix phase forming material can comprise a liquid crystal material chosen form liquid crystal monomers, liquid crystal pre-polymers, and liquid crystal polymers. Further, according to various non-limiting embodiments, the guest phase forming material can comprise a liquid crystal material chosen from liquid crystal mesogens, liquid crystal monomers, and liquid crystal polymers and pre-polymers. Non-limiting examples of such materials are set forth in detail above.

In one specific non-limiting embodiment, phase-separating polymer system can comprise a mixture of a matrix phase forming material comprising a liquid crystal monomer, a guest phase forming material comprising liquid crystal mesogens, and at least one photochromic-dichroic compound. According to this non-limiting embodiment, causing at least a portion of the guest phase forming material to separate from at least a portion of the matrix phase forming material can comprise polymerization induced phase-separation. That is, at least a portion of the liquid crystal monomer of the matrix phase can be polymerized and thereby separated from at least a portion of the liquid crystal mesogens of the guest phase forming material. Non-limiting methods of polymerization that can be used in conjunction with various non-limiting embodiments disclosed herein include photo-induced polymerization and thermally-induced polymerization.

In another specific non-limiting embodiment, phase-separating polymer system can comprise a mixture of a matrix phase forming material comprising a liquid crystal monomer, a guest phase forming material comprising a low viscosity liquid crystal monomer having a different functionality from the liquid crystal monomer of the matrix phase, and at least one photochromic-dichroic compound. As used herein, the term "low viscosity liquid crystal monomer," refers to a liquid crystal monomer mixture or solution that is freely flowing at room temperature. According to this non-limiting embodiment, causing at least a portion of the guest phase forming material to separate from at least a portion of the matrix phase forming material can comprise polymerization induced phase-separation. That is, at least a portion of the liquid crystal monomer of the matrix phase can be polymerized under conditions that do not cause the liquid crystal monomer of the guest phase to polymerize. During polymerization of the matrix phase forming material, the guest phase forming material will separate from the matrix phase forming material. Thereafter, the liquid crystal monomer of the guest phase forming material can be polymerized in a separate polymerization process.

In another specific non-limiting embodiment, the phase-separating polymer system can comprise a solution in at least one common solvent of a matrix phase forming material comprising a liquid crystal polymer, a guest phase forming material comprising a liquid crystal polymer that is different from the liquid crystal polymer of the matrix phase forming material, and at least one photochromic-dichroic compound. According to this non-limiting embodiment, causing at least a portion of the guest phase forming material to separate from the matrix phase forming material can comprise solvent induced phase-separation. That is, at least a portion of the at least one common solvent can be evaporated from the mixture of liquid crystal polymers, thereby causing the two phases to separate from each other.

Alternatively, according to various non-limiting embodiments disclosed herein, forming the at least partial coating comprising the at least one at least partially aligned photochromic-dichroic compound can comprise applying at least one anisotropic material to at least a portion of the substrate, imbibing the at least one photochromic-dichroic compound into at least a portion of the at least one anisotropic material, at least partially ordering at least a portion of the anisotropic material, and at least partially aligning at least a portion of the at least one photochromic-dichroic compound with at least a portion of the at least partially ordered anisotropic material. Further, although not limiting herein, at least partially ordering at least a portion of the anisotropic material can occur before imbibing the at least one photochromic-dichroic compound into at least a portion thereof. Still further, although not required, the at least one photochromic-dichroic compound can be at least partially aligned while in an activated state. Non-limiting methods of applying and aligning anisotropic materials are described herein below.

For example, according to one non-limiting embodiment, the at least one photochromic-dichroic compound can be imbibed into the anisotropic material, for example, by applying a solution or mixture of the at least one photochromic-dichroic compound in a carrier to a portion of the at least anisotropic material and allowing at least a portion of the at least one photochromic-dichroic compound to diffuse into the anisotropic material, either with or without heating. Further, according to this non-limiting embodiment, the anisotropic material can be part of a phase-separated polymer coating as described above.

Other non-limiting embodiments disclosed herein provide a method of making an optical element comprising imparting at least one orientation facility to at least a portion of a substrate, and subsequently forming an at least partial coating comprising at least one at least partially aligned photochromic-dichroic compound on at least a portion of the at least one orientation facility. According to this and other non-limiting embodiments disclosed herein, imparting the at least one orientation facility to the at least a portion of a substrate can comprise at least one of: forming an at least partial coating comprising an at least partially ordered alignment medium on at least a portion of the substrate, applying an at least partially ordered polymer sheet to the at least a portion of the substrate, at least partially treating at least a portion of the substrate, and forming a Langmuir-Blodgett film on at least a portion of the substrate.

According to one non-limiting embodiment, imparting the at least one orientation facility on the at least a portion of the substrate can comprise forming an at least partial coating comprising an at least partially ordered alignment medium on at least a portion of the substrate. Further, according to this non-limiting embodiment, forming the at least partial coating can comprise applying an alignment medium to the at least a portion of the substrate and at least partially ordering at least a portion of the alignment medium. Methods of at least partially ordering at least portion of the alignment medium that can be used in conjunction with this and other non-limiting embodiments disclosed herein include, but are not limited to, exposing the at least a portion of the alignment medium to at least one of linearly polarized ultraviolet radiation, linearly polarized infrared radiation, linearly polarized visible radiation, a magnetic field, an electric field, and a shear force. Further, ordering at least portion of the alignment medium can comprise at least partially treating at least a portion of a surface of the at least partial coating comprising the alignment medium by, for example and without limitation, etching or rubbing the at least a portion of the alignment medium.

For example, although not limiting herein, according to one non-limiting embodiment wherein the orientation facility comprises an at least partial coating comprising an alignment medium that is a photo-orientation material (such as, but not limited to a photo-orientable polymer network), imparting the orientation facility can comprise forming an at least partial coating comprising a photo-orientation material on at least a portion of the substrate, and at least partially ordering at least a portion of the photo-orientation material by exposing the at least a portion to linearly polarized ultraviolet radiation. Thereafter, the at least one photochromic-dichroic compound can be applied to at least a portion of the at least partially ordered photo-orientation material and at least partially aligned.

Although not required, according to various non-limiting embodiments wherein imparting the orientation facility comprises forming an at least partial coating of an at least partially ordered alignment medium, at least a portion of the alignment medium can be at least partially set. Further, at least partially setting the at least a portion of the alignment medium can occur at essentially the same time as aligning the at least a portion of the alignment medium or it can occur after aligning the at least a portion of the alignment medium. Still further, according to various non-limiting embodiments disclosed herein, at least partially setting the at least a portion of the alignment medium can comprise at least partially curing the at least a portion by exposing the at least a portion of the alignment medium to infrared, ultraviolet, gamma, microwave or electron radiation so as to initiate the polymerization reaction of the polymerizable components or cross-linking with or without a catalyst or initiator. If desired or required, this can be followed by a heating step.

As discussed above, according to various non-limiting embodiments disclosed herein, subsequent to imparting the orientation facility on at least a portion of the substrate, an at least partial coating comprising at least one at least partially aligned photochromic-dichroic compound is formed on at least a portion of the orientation facility. Methods of forming at least partial coatings comprising at least one photochromic-dichroic compound that is at least partially aligned on at least a portion of the at least one orientation facility include those methods of forming at least partial coatings comprising at least one photochromic-dichroic compound that is at least partially aligned on at least a portion of a substrate that are set forth above in detail.

For example, although not limiting herein, forming the at least partial coating comprising the at least one at least partially aligned photochromic-dichroic compound can include, spin coating, spray coating, spray and spin coating, curtain coating, flow coating, dip coating, injection molding, casting, roll coating, wire coating, and overmolding a composition comprising the photochromic-dichroic compound on to the orientation facility, and thereafter, aligning at least a portion of the photochromic-dichroic compound with the orientation facility and/or with another material or structure (such as an alignment transfer material if present), with or without exposure to a magnetic field, an electric field, linearly polarized infrared radiation, linearly polarized ultraviolet radiation, linearly polarized visible radiation or a shear force.

According to one non-limiting embodiment, forming the at least partial coating comprising the at least one photochromic-dichroic compound that is at least partially aligned on at least a portion of the at least one orientation facility can comprise applying a polymerizable composition, at least one anisotropic material, and at least one photochromic-dichroic compound on at least a portion of the at least one orientation facility. Thereafter, at least a portion of the at least one anisotropic material can be at least partially aligned with at least a portion of the at least one orientation facility and at least partially aligning at least a portion of the at least one photochromic-dichroic compound with at least a portion of the at least partially aligned anisotropic material. After at least partially aligning at least a portion of the at least one anisotropic material and the at least one photochromic-dichroic compound, at least a portion of the at least partial coating can be subjected to a dual curing process, wherein at least a portion of the at least one anisotropic material and at least a portion of the polymerizable composition are at least partially set using at least two curing methods. Non-limiting examples of suitable curing methods include exposing the at least partial coating to ultraviolet radiation, visible radiation, gamma radiation, microwave radiation, electron radiation, or thermal energy.

For example, although not limiting herein, in one embodiment at least a portion of the anisotropic material can be exposed to ultraviolet or visible radiation to cause at least a portion of the at least one anisotropic material to at least partially set. Thereafter, at least a portion of the polymerizable composition can be at least partially set by exposure to thermal energy. Further, although not required, at least a portion of the at least one photochromic-dichroic compound can be at least partially aligned with at least a portion of the at least one anisotropic material while in an activated state by exposing the at least partial coating to ultraviolet radiation sufficient to cause the photochromic-dichroic compound to switch from a first state to a second state, but insufficient to cause the anisotropic material to at least partially set, while the at least one anisotropic material is at least partially aligned with at least a portion of the at least one orientation facility (as discussed above).

In one specific non-limiting embodiment, the polymerizable composition can be dihydroxy and isocyanate monomers and the at least one anisotropic material can comprise a liquid crystal monomer. According to this non-limiting embodiment, after applying the polymerizable composition, the anisotropic material and the at least one photochromic-dichroic compound on the orientation facility, at least a portion of the anisotropic material can be at least partially aligned with at least a portion of the at least one orientation facility and the at least one photochromic-dichroic compound can be at least partially aligned with the anisotropic material. Further, after alignment, at least a portion of the coating can be exposed to ultraviolet or visible radiation sufficient to cause at least a portion the anisotropic material to least partially set. Further, before, during or after setting at least a portion of the anisotropic material, at least a portion of the polymerizable composition can be at least partially set by exposing at least a portion of the at least partial coating to thermal energy.

In another non-limiting embodiment, the dual cure process can comprise first exposing at least a portion of the polymerizable composition to thermal energy sufficient to cause at least a portion of the at polymerizable composition to at least partially set. Thereafter, at least a portion of the at least one anisotropic material can be exposed to ultraviolet or visible radiation to cause at least a portion of the anisotropic material to at least partially set. Further, at least a portion of the at least one anisotropic material can be at least partially aligned before, during or after exposing at least a portion of the coating to thermal energy and prior to at least partially setting at least a portion of the at least one anisotropic material.

In still another non-limiting embodiment, the dual cure process can comprise at least partially setting at least a portion of the polymerizable composition at essentially the same time as at least partially setting at least a portion of the anisotropic material, for example, by simultaneously exposing the at least partial coating to ultraviolet or visible radiation and thermal energy.

Further, as previously discussed in relation to coatings comprising interpenetrating polymer networks, according to various non-limiting embodiments disclosed herein, polymerizable composition can be an isotropic material or an anisotropic material, provided that the at least partial coating comprising the at least one at least partially aligned photochromic-dichroic compound is, on the whole, anisotropic.

Additionally, the methods of making optical elements and devices according to various non-limiting embodiments disclosed herein can further comprise forming an at least partial primer coating on at least a portion of the substrate prior to imparting the at least one orientation facility to the at least a portion of the substrate or prior to forming an at least partial coating comprising the at least one at least partially aligned photochromic-dichroic compound thereon. Moreover, at least one additional at least partial coating chosen from photochromic coatings, anti-reflective coatings, linearly polarizing coatings, circularly polarizing coatings, elliptically polarizing coatings, transitional coatings, primer coatings and protective coatings can be formed on at least a portion of at least one surface of the substrate and/or over at least a portion of the at least partial coating comprising the least one photochromic-dichroic compound. Non-limiting examples of suitable primer coatings, photochromic coatings, anti-reflective coatings, linearly polarizing coatings, transitional coatings, primer coatings and protective coatings are all described above.

Other non-limiting embodiments disclosed herein provide methods of making an optical element comprising forming an at least partial coating on at least a portion of a substrate and adapting at least a portion of the at least partial coating to switch from a first state to a second linearly polarizing state in response to actinic radiation and to revert back to the first sate in response to thermal energy. According to one non-limiting embodiment forming the at least partial coating on at least a portion of the substrate and adapting at least a portion of the at least partial coating to switch from a first state to a second linearly polarizing state in response to actinic radiation and to revert back to the first sate in response to thermal energy can occur at essentially the same time. According to another non-limiting embodiment, forming the at least partial coating on at least a portion of the substrate occurs prior to adapting the at least a portion of the at least partial coating to switch from a first state to a second linearly polarizing state in response to actinic radiation and to revert back to the first sate in response to thermal energy. According to still another non-limiting embodiment, forming the at least partial coating on at least a portion of the substrate occurs after adapting the at least a portion of the at least partial coating to switch from a first state to a second linearly polarizing state in response to actinic radiation and to revert back to the first sate in response to thermal energy.

In one non-limiting embodiment, forming the at least partial coating on the at least a portion of the substrate can comprise applying at least one anisotropic material and at least one photochromic-dichroic compound to at least a portion of the substrate, and adapting at least a portion of the at least partial coating to switch from a first state to a second linearly polarizing state in response to actinic radiation and to revert back to the first sate in response to thermal energy can comprise at least partially aligning at least a portion of the at least one photochromic-dichroic compound. Further, according to this non-limiting embodiment at least partially aligning at least a portion of the at least one photochromic-dichroic compound can comprise at least partially ordering at least a portion of the at least one anisotropic material and at least partially aligning the at least one photochromic-dichroic compound with at least a portion of the at least partially ordered at least one anisotropic material. Still further, although not required, the at least one photochromic-dichroic compound can be aligned while in an activated state, for example, by exposing the photochromic-dichroic compound to actinic radiation sufficient to cause the photochromic-dichroic compound to switch from a first state to a second state while aligning the photochromic-dichroic compound.

In another non-limiting embodiment, forming the at least partial coating on at least a portion of the substrate can comprise applying an alignment medium to the at least a portion of the substrate, and adapting at least a portion of the at least partial coating to switch from a first state to a second linearly polarizing state in response to actinic radiation and to revert back to the first sate in response to thermal energy can comprise at least partially ordering at least a portion of the alignment medium, applying at least one photochromic-dichroic compound to at least a portion of the at least partial coating comprising the alignment medium, and at least partially aligning at least a portion of the at least one photochromic-dichroic compound.

In one non-limiting embodiment, applying the at least one photochromic-dichroic compound to at least a portion of the at least partial coating comprising the at least partially ordered alignment medium can comprise forming an at least partial coating comprising the at least one photochromic-dichroic compound and at least one anisotropic material on at least a portion of the at least partial coating comprising the at least partially ordered alignment medium. Moreover, at least partially aligning at least a portion of the at least one photochromic-dichroic compound can comprise aligning at least a portion of the at least one anisotropic material with at least a portion of the at least partially ordered alignment medium. Further, although not required, at least a portion of the at least partial coating comprising the alignment medium can be at least partially set prior to applying the at least one photochromic-dichroic compound.

Additionally or alternatively, the at least one photochromic-dichroic compound can be applied to at least a portion of the at least partial coating comprising the at least partially ordered alignment medium by imbibition. Suitable imbibition techniques are described, for example, U.S. Pat. Nos. 5,130,353 and 5,185,390, the specifications of which are specifically incorporated by reference herein. For example, although not limiting herein, the photochromic-dichroic compound can be applied to at least a portion of the at least partial coating comprising the at least partially ordered alignment medium by applying the at least one photochromic-dichroic compound, either as the neat photochromic-dichroic compound or dissolved in a polymeric or other organic solvent carrier, and allowing the photochromic-dichroic compound to diffuse into at least a portion of the at least partial coating comprising the at least partially ordered alignment medium, either with or with out heating. Further, if desired, the at least one photochromic-dichroic compound can be exposed to actinic radiation sufficient to cause the at least one photochromic compound to switch from a first state to a second state during diffusion.

Other non-limiting embodiments disclosed herein provide a method of making an optical element comprising forming an at least partial coating comprising an alignment medium on at least a portion of at least one surface of a substrate and at least partially ordering at least a portion of the alignment medium, forming at least one at least partial coating comprising an alignment transfer material on at least a portion of the at least partial coating comprising the alignment medium and at least partially aligning at least a portion of the alignment transfer material with at least a portion of the at least partially ordered alignment medium, and forming an at least partial coating comprising an anisotropic material and at least one photochromic-dichroic compound on at least a portion of the alignment transfer material, at least partially aligning at least a portion of the anisotropic material with at least a portion of the at least partially aligned alignment transfer material, and at least partially aligning at least a portion of the at least one photochromic-dichroic compound with at least a portion of the at least partially aligned anisotropic material.

Further, according to various non-limiting embodiments disclosed herein, forming the at least one at least partial coating comprising the alignment transfer material can comprise forming a first at least partial coating comprising an alignment transfer material, the first at least partial coating having a thickness ranging from 2 to 8 microns, at least partially aligning at least a portion of the alignment transfer material of the first at least partial coating with at least a portion of the at least partially ordered alignment medium, and at least partially setting at least a portion of the at least partially ordered alignment transfer material of the first at least partial coating. Thereafter, a second at least partial coating having a thickness ranging from greater than 5 to 20 microns and comprising an alignment transfer material can be applied to at least a portion of the first at least partial coating and at least a portion of the alignment transfer material of the second at least partial coating can be at least partially aligned with at least a portion of the at least partially aligned alignment transfer material of the first at least partial coating.

Still other non-limiting embodiments disclosed herein provide a method of making a composite optical element comprising connecting at least one at least partially ordered polymeric sheet to at least a portion of a substrate, the at least partially ordered polymeric sheet comprising at least one at least partially aligned photochromic-dichroic compound connected to at least a portion thereof and having an average absorption ratio greater than 2.3 in an activated state as determined according to the CELL METHOD. Although not limiting herein, according to this non-limiting embodiment, the at least one at least partially ordered polymeric sheet can comprise, for example, a stretched polymer sheet, a photo-oriented polymer sheet, an at least partially ordered phase-separated polymer sheet, or a combination thereof.

Other non-limiting embodiments disclosed herein provide a method of making a composite optical element comprising connecting a sheet comprising an at least partially ordered liquid crystal polymer having at least a first general direction, an at least partially ordered liquid crystal material distributed within at least a portion of the at least partially ordered liquid crystal polymer, and at least one photochromic-dichroic compound that is at least partially aligned with the at least partially ordered liquid crystal material to at least a portion of the substrate. Further, according to this non-limiting embodiment, the at least partially ordered liquid crystal material distributed within the at least a portion of the at least partially ordered liquid crystal polymer can have at least a second general direction that is generally parallel to at least the first general direction of the liquid crystal polymer.

For example, although not limiting herein, according to one non-limiting embodiment, forming the sheet can comprise applying a phase-separating polymer system comprising a matrix phase forming material comprising a liquid crystal material, a guest phase forming material comprising a liquid crystal material, and at least one photochromic-dichroic compound on to at least a portion a substrate. Thereafter, at least a portion of the matrix phase forming material and at least a portion of the guest phase forming material can be at least partially ordered, and a least a portion of the at least one photochromic-dichroic compound can be at least partially aligned with at least a portion of the guest phase forming material. After alignment, at least a portion of the guest phase forming material can be separated from at least a portion of the matrix phase forming material by at least one of polymerization induced phase-separation and solvent induced phase-separation, and the at least partially ordered, phase-separated polymer coating can be removed from the substrate to form the sheet.

Alternatively, the phase-separating polymer system can be applied on the substrate, ordered and aligned as discussed above, and thereafter removed from the substrate to form a phase-separated polymer sheet. Subsequently, at least one photochromic-dichroic compound can be imbibed into at least a portion of the sheet. Alternatively or additionally, at least one photochromic-dichroic compound can be imbibed into the coating prior to removing the coating from the substrate to form the sheet.

According to still another non-limiting embodiment forming the sheet can comprise: forming an at least partially ordered liquid crystal polymer sheet and imbibing liquid crystal mesogens and at least one photochromic-dichroic compound into at least a portion of the at least partially ordered liquid crystal polymer sheet. For example, according to this non-limiting embodiment, a sheet comprising a liquid crystal polymer can be formed and at least partially ordered by a method of forming a polymer sheet that can at least partially order the liquid crystal polymer during formation, for example by extrusion. Alternatively, a liquid crystal polymer can be cast onto a substrate and at least partially ordered by one of the non-limiting methods of at least partially ordering liquid crystal materials set forth above. For example, although not limiting herein, at least a portion of the liquid crystal material can be exposed to a magnetic or an electric field. After being at least partially ordered, the liquid crystal polymer can be at least partially set and removed from the substrate to form a sheet comprising an at least partially ordered liquid crystal polymer matrix. Still further, a liquid crystal polymer sheet can be cast, at least partially set, and subsequently stretched to form sheet comprising an at least partially ordered liquid crystal polymer.

After forming the sheet comprising the at least partially ordered liquid crystal polymer, at least one liquid crystal mesogen and at least one photochromic-dichroic compound can be imbibed into at least a portion of the liquid crystal polymer matrix. For example, although not limiting herein, the at least one liquid crystal mesogen and the at least one photochromic-dichroic compound can be imbibed into at least a portion of the liquid crystal polymer by applying a solution or mixture of the that least one liquid crystal mesogen and the at least one photochromic-dichroic compound in a carrier to a portion of the liquid crystal polymer and, thereafter, allowing at least a portion of the at least one liquid crystal mesogen and the at least one photochromic-dichroic compound to diffuse into the liquid crystal polymer sheet, either with or without heating. Alternatively, the sheet comprising the liquid crystal polymer can be immersed into a solution or mixture of the at least one liquid crystal mesogen and the at least one photochromic-dichroic compound in a carrier and the at least one liquid crystal mesogen and the at least one photochromic-dichroic compound can be imbibed into the liquid crystal polymer sheet by diffusion, either with or without heating.

According to still another non-limiting embodiment, forming the sheet can comprise forming a liquid crystal polymer sheet, imbibing at least a portion of the liquid crystal polymer sheet with at least one liquid crystal mesogen and at least one photochromic-dichroic compound (for example as discussed above), and thereafter at least partially ordering at least a portion of the liquid crystal polymer, at least a portion of the at least one liquid crystal mesogen, and the at least one photochromic-dichroic compound distributed therein. Although not limiting herein, for example, at least a portion of the liquid crystal polymer sheet, at least a portion of the at least one liquid crystal mesogen, and at least a portion of the at least one photochromic-dichroic compound distributed therein can be at least partially ordered by stretching the liquid crystal polymer sheet. Further according to this non-limiting embodiment, the liquid crystal polymer sheet can be formed using conventional polymer processing techniques, such as, but not limited to, extrusion and casting.

In still another non-limiting embodiment, a photo-oriented polymer sheet comprising an at least partial coating of an anisotropic material and at least one photochromic-dichroic compound is applied to the substrate. For example, according to this non-limiting embodiment, photo-oriented polymer sheet can be formed by applying an at least partial layer of a photo-orientable polymer network on a release layer and subsequently ordering and at least partially curing at least a portion of the photo-orientable polymer network; forming an at least partial coating of an anisotropic material and at least one photochromic-dichroic compound on at least a portion of at least partial layer comprising the photo-orientable polymer network, at least partially aligning at least a portion of the anisotropic material and the at least one photochromic-dichroic compound with at least a portion of the photo-orientable polymer network, and at least partially curing at least a portion of the anisotropic material. The release layer can then be removed and the at least partial layer of the photo-orientable polymer network comprising the at least partial coating of the anisotropic material and the at least one photochromic-dichroic compound from the release layer to form the at least partially ordered polymeric sheet.

Further, according to various non-limiting embodiments disclosed herein, connecting the polymeric sheet comprising the at least one at least partially aligned photochromic-dichroic compound to at least a portion of the substrate can comprise, for example, at least one of: laminating, fusing, in-mold casting, and adhesively bonding the polymeric sheet to the at least a portion of the substrate. As used herein, the in-mold casting includes a variety of casting techniques, such as but not limited to: overmolding, wherein the sheet is placed in a mold and the substrate is formed (for example by casting) over at least a portion of the sheet; and injection molding, wherein the substrate is formed around the sheet. According to one non-limiting embodiment, the polymeric sheet can be laminated on a surface of a first portion of the substrate, and the first portion of the substrate can be placed in a mold. Thereafter, a second portion of the substrate can be formed (for example by casting) on top of the first portion of the substrate such that the polymeric layer is between the two portions of the substrate.

Another specific non-limiting embodiment provides a method of making an optical element comprising overmolding an at least partial coating comprising an at least partially ordered liquid crystal material and at least one at least partially aligned photochromic-dichroic compound on at least a portion of an optical substrate, and more particularly, on at least a portion of an ophthalmic substrate. Referring now to FIG. 2, according to this non-limiting embodiment, the method comprises placing at least portion of a surface 210 of an optical substrate 212 adjacent a to a surface 214 of a transparent mold 216 to define a molding region 217. The surface 214 of transparent mold 216 can be concave or spherically negative (as shown), or it can have other configuration as required. Further, although not required, a gasket or spacer 215 can be placed between optical substrate 212 and transparent mold 216. After positioning the optical substrate 212, a liquid crystal material 218 containing at least one photochromic-dichroic compound (not shown) can be introduced into the molding region 217 defined by the surface 210 of the optical substrate 212 and the surface 214 of the transparent mold 216, such that at least a portion of the liquid crystal material 218 is caused to flow therebetween. Thereafter, at least a portion of the liquid crystal material 218 can be at least partially ordered, for example, by exposure to an electric field, a magnetic field, linearly polarized infrared radiation, linearly polarized ultraviolet radiation, and/or linearly polarized visible radiation, and at least a portion of the at least one photochromic-dichroic compound can be at least partially aligned with at least a portion of the at least partially ordered liquid crystal material. Thereafter, the liquid crystal material can be at least partially polymerized. After polymerization, the optical substrate having the at least partial coating comprising an at least partially ordered liquid crystal material and the at least one at least partially aligned photochromic-dichroic compound on at least a portion of a surface thereof can be released from the mold.

Alternatively, the liquid crystal material 218 containing the at least one photochromic-dichroic compound can be introduced onto surface 214 of transparent mold 216 prior to placing at least a portion of surface 210 of the optical substrate 212 adjacent thereto such that at least a portion of surface 210 contacts at least a portion of the liquid crystal material 218, thereby causing the liquid crystal material 218 to flow between surface 210 and surface 214. Thereafter, the liquid crystal material 218 can be at least partially ordered, and at least a portion of the at least one photochromic-dichroic compound can be at least partially aligned as discussed above. After polymerization of at least a portion of the liquid crystal material, the optical substrate having the at least partial coating comprising an at least partially ordered liquid crystal material and the at least one at least partially aligned photochromic-dichroic compound on at least a portion of a surface thereof can be released from the mold.

According to still other non-limiting embodiments, an at least partial coating comprising at least partially ordered liquid crystal material, without the photochromic-dichroic compound, can be formed on the surface of an optical substrate as discussed above. After releasing the substrate and the coating from the mold, at least one photochromic-dichroic compound can be imbibed into the at least partially ordered liquid crystal material.

Although not shown in FIG. 2, additionally or alternatively, an orientation facility having at least a first general direction can be imparted onto at least a portion of the surface of the transparent mold prior to introducing the liquid crystal material into the mold and/or onto at least a portion of the surface of the optical substrate prior contacting the surface of the optical substrate with the liquid crystal material. Further, according to this non-limiting embodiment, at least partially ordering at least a portion of the liquid crystal material can comprise at least partially aligning at least a portion of the liquid crystal material with at least a portion of the at least one orientation facility on the surface of the mold and/or at least a portion of the at least one orientation facility on the surface of the optical substrate.

Although not limiting herein, it is contemplated that the aforementioned over molding methods of making at least partial coatings can be particularly useful in forming coatings on multi-focal ophthalmic lenses, or for forming at least partial coatings for other applications where relatively thick alignment facilities are desired.

As previously discussed, various non-limiting embodiments disclosed herein relate to display elements and devices. Further, as previously discussed, as used herein the term "display" means the visible representation of information in words, numbers, symbols, designs or drawings. Non-limiting examples of display elements and devices include screens, monitors, and security elements. Non-limiting examples of security elements include security marks and authentication marks that are connected to at least a portion of a substrate, such as and without limitation: access cards and passes, e.g., tickets, badges, identification or membership cards, debit cards etc.; negotiable instruments and non-negotiable instruments, e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

For example, in one non-limiting embodiment, the display element is a security element connected to at least a portion of a substrate. According to this non-limiting embodiment the security element comprises an at least partial coating having a first state and a second state, and being adapted to switch from a first state to a second state in response to at least actinic radiation, to revert back to the first state in response to thermal energy, and to linearly polarize at least transmitted radiation in at least one of the first state and the second state. Non-limiting examples of at least partial coatings adapted to switch from a first state to a second state in response to at least actinic radiation, to revert back to the first state in response to thermal energy, and to linearly polarize at least transmitted radiation in at least one of the first state and the second state and methods of making the same are set forth above in detail.

According to this non-limiting embodiment, the security element can be a security mark and/or an authentication mark. Further, the security element can be connected to at least a portion of a substrate chosen from a transparent substrate and a reflective substrate. Alternatively, according to certain non-limiting embodiments wherein a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Still further, security element can be connected to at least a portion of a substrate chosen from untinted substrates, tinted substrates, photochromic substrates, tinted-photochromic substrates, linearly polarizing substrates, circularly polarizing substrates, and elliptically polarizing substrates.

Additionally, the at least partial coatings according to the aforementioned non-limiting embodiment can comprise at least one photochromic-dichroic compound having an average absorption ratio of at least 1.5 in an activated state as determined according to the CELL METHOD. According to other non-limiting embodiments disclosed herein, the at least one photochromic-dichroic compound can have an average absorption ratio greater than 2.3 in an activated state as determined according to the CELL METHOD. According to still other non-limiting embodiments, the at least one at least partially aligned photochromic-dichroic compound can have an average absorption ratio ranging from 1.5 to 50 in an activated state as determined according to the CELL METHOD. According to other non-limiting embodiments, the at least one at least partially aligned photochromic-dichroic compound can have an average absorption ratio ranging from 4 to 20, can further having an average absorption ratio ranging from 3 to 30, and can still further having an average absorption ratio ranging from 2.5 to 50 in an activated state as determined according to the CELL METHOD. However, generally speaking, the average absorption ratio of the at least one at least partially aligned photochromic-dichroic compound can be any average absorption ratio that is sufficient to impart the desired properties to the device or element. Non-limiting examples of photochromic-dichroic compounds that are suitable for use in conjunction with this non-limiting embodiment are set forth above in detail.

Furthermore, the security elements according to the aforementioned non-limiting embodiment can further comprise one or more other coatings or sheets to form a multi-layer reflective security element with viewing angle dependent characteristics as described in U.S. Pat. No. 6,641,874, which is hereby specifically incorporated by reference herein. For example, one non-limiting embodiment provides a security element connected to at least a portion of a substrate comprising an at least partial coating having a first state and a second state, and being adapted to switch from a first state to a second state in response to at least actinic radiation, to revert back to the first state in response to thermal energy, and to linearly polarize at least transmitted radiation in at least one of the first state and the second state on at least a portion of the substrate; and at least one additional at least partial coating or sheet chosen from polarizing coatings or sheets, photochromic coatings or sheets, reflective coatings or sheets, tinted coatings or sheets, circularly polarizing coatings or sheets, retarder coatings or sheets (i.e., coatings or sheets that delay or retard the propagation radiation therethrough), and wide-angle view coatings or sheets (i.e., coatings or sheets than enhancing viewing angle). Further, according to this non-limiting embodiment, the at least one additional at least partial coating or sheet can be positioned over the at least partial coating having the first state and the second state, under this least partial coating, or multiple coating and/or sheets can be positioned over and/or under this coating.

Other non-limiting embodiments provide a liquid crystal cell, which may be a display element or device, comprising a first substrate having a first surface and a second substrate having a second surface, wherein the second surface of the second substrate is opposite and spaced apart from the first surface of the first substrate so as to define an open region. Further, according to this non-limiting embodiment, a liquid crystal material adapted to be at least partially ordered and at least one photochromic-dichroic compound adapted to be at least partially aligned and having an average absorption ratio of at least 1.5 in the activated state as determined according to the CELL METHOD positioned within the open region defined by the first surface and the second surface to form the liquid crystal cell.

Further according to this non-limiting embodiment, the first substrate and the second substrate can be independently chosen from untinted substrates, tinted substrates, photochromic substrates, tinted-photochromic substrates, and linearly polarizing substrates.

The liquid crystal cells according to various non-limiting embodiments disclosed herein can further comprise a first orientation facility positioned adjacent the first surface and a second orientation facility positioned adjacent the second surface. As previously discussed, it is possible to align a liquid crystal material with an oriented surface. Thus, according to this non-limiting embodiment, at least a portion of the liquid crystal material of the liquid crystal cell can be at least partially aligned with at least a portion of the first and second orientation facilities.

Still further, a first electrode can be positioned adjacent at least a portion of the first surface, a second electrode can be positioned adjacent at least a portion of the second surface, and the liquid crystal cell can form at least a portion of an electrical circuit. Further, if an orientation facility is present (as discussed above), the electrode can be interposed between the orientation facility and the surface of the substrate.

Additionally, the liquid crystal cells according to various non-limiting embodiments disclosed herein can further comprise an at least partial coating or sheet chosen from linearly polarizing coatings or sheets, photochromic coatings or sheets, reflective coatings or sheets, tinted coatings or sheets, circularly polarizing coatings or sheets, elliptically polarizing coating or sheets, retarder coatings or sheets, and wide-angle view coatings or sheets connected to at least a portion of a surface of at least one of the first substrate and the second substrate.

Other non-limiting embodiments disclosed herein provide an optical element comprising a substrate and an at least partial coating having a first state and a second state on at least a portion of the substrate, the at least partial coating comprising a chiral nematic or cholesteric liquid crystal material having molecules that are helically arranged through the thickness of the at least partial coating; and at least one photochromic-dichroic compound that is at least partially aligned with the liquid crystal material such that the long axis of the molecules of the photochromic-dichroic compound are generally parallel to the molecules of the liquid crystal material. According to this non-limiting embodiment, the at least partial coating can be adapted to be circularly polarizing or elliptically polarizing in at least one state.

Various non-limiting embodiments disclosed herein will now be illustrated in the following non-limiting examples.

EXAMPLES

Example 1

Sample substrates having a coating comprising an aligned anisotropic material and a photochromic-dichroic compound that was at least partially aligned in the activated state connected thereto were prepared as follows. A comparative substrate having a coating comprising an aligned anisotropic material and a commercially available photochromic dye that was at least partially aligned in the activated state connected thereto was also prepared as follows.

Part A: Preparation of Solutions of Anisotropic Materials

Each of the liquid crystal monomers listed in Table I were added to a beaker in the order listed with stirring:

TABLE I

| Liquid Crystal Monomer | Amount (g) |
| --- | --- |
| RM 23[1] | 3.25 |
| RM 257[2] | 3.25 |
| RM 82[3] | 3.25 |
| RM 105[4] | 3.25 |

[1]RM 23 is a liquid crystal monomer (LCM) available from EMD Chemicals, Inc and is reported to have the molecular formula of $C_{23}H_{23}NO_5$.
[2]RM 257 is a liquid crystal monomer (LCM) available from EMD Chemicals, Inc and is reported to have the molecular formula of $C_{33}H_{32}O_{10}$.
[3]RM 82 is a liquid crystal monomer (LCM) available from EMD Chemicals, Inc and is reported to have the molecular formula of $C_{39}H_{44}O_{10}$.
[4]RM 105 is a liquid crystal monomer (LCM) available from EMD Chemicals, Inc and is reported to have the molecular formula of $C_{23}H_{26}O_6$.

Anisole (7.0 grams) was then added to the beaker and the resulting mixture was heated to 60° C. and stirred until the solids were dissolved as determined by visual observation. The resulting liquid crystal monomer solution (LCMS) had 65 percent solids.

Part B: Preparation of Photochromic-Dichroic Compounds

The following three (3) photochromic-dichroic compounds (P/D-1, P/D-2, and P/D-3, respectively) were prepared as follows.

P/D-1

Step 1

1-phenyl-1-(4-phenylpiperazin-1-yl)phenyl)-prop-2-yn-1-ol (15.8 g, 49.4 mmol), 2,3-dimethoxy-7,7-dimethyl-7H-benzo[c]fluoren-5-ol (17.4 g, 54.3 mmol) and chloroform (400 mL) were added to a 1000 mL flask equipped with a dropping funnel and stirred at room temperature. A chloroform solution of trifluoroacetic acid (0.5 g, 4.4 mmol, in 20 mL chloroform) was added dropwise to the reaction flask via the dropping funnel. A gray color was obtained after the addition. The resulting reaction mixture was refluxed for 6 hours and then was stirred overnight at room temperature. The chloroform solution was washed with a saturated sodium bicarbonate water solution, dried over magnesium sulfate and concentrated. The product was recrystallized from $CHCl_3$/ethyl ether. An off-white solid (26.3 g, yield 91%) was obtained. An NMR spectrum showed that the product had a structure consistent with 3-phenyl-3-(4-(4-phenyl-piperazin-1-yl)phenyl)-13,13-dimethyl-6,7-dimethoxy-indeno[2',3':3,4]naphtho[1,2-b]pyran.

Step 2

Under a nitrogen atmosphere at room temperature, 3-phenyl-3-(4-(4-phenyl-piperazin-1-yl)phenyl)-13,13-dimethyl-6,7-dimethoxy-indeno[2',3':3,4]naphtho[1,2-b]pyran from Step 1 (12 g, 17.9 mmol), 1-(4-hydroxyphenyl)piperazine (9.56 g, 53.7 mmol) and THF (200 mL) were added to a 1 liter flask equipped with a dropping funnel and stirred. A 1.6 M solution of methyl lithium in ethyl ether (67 mL) was added slowly and carefully via the dropping funnel. An ice bath was used occasionally when the mixture started to boil. During and after the addition of methyl lithium, a large quantity of precipitate was produced within the flask. Thirty minutes after the addition of methyl lithium, the reaction mixture was poured into a 4 L beaker containing 3 L of ice water. The basic mixture was acidified to a pH value of about 4 by the addition of 3 N HCl. The precipitate formed was collected by vacuum filtration, dissolved in chloroform, dried over magnesium sulfate, concentrated and flash chromatographed. A gray solid (12.6 g, yield 86%) was obtained as the product. An NMR spectrum showed that the resulting product had a structure consistent with 3-phenyl-3-(4-(4-phenyl-piperazin-1-yl)phenyl)-13,13-dimethyl-6-methoxy-7-(4-(4-hydroxyphenyl)-piperazin-1-yl)-indeno[2',3':3,4]naphtho[1,2-b]pyran.

Step 3

3-phenyl-3-(4-(4-phenyl-piperazin-1-yl)phenyl)-13,13-dimethyl-6-methoxy-7-(4-(4-hydroxyphenyl)-piperazin-1-yl)-indeno[2',3':3,4]naphtho[1,2-b]pyran from Step 2 (0.67 g, 0.82 mmol), 4-n-octyloxybiphenyl-4'-carboxylic acid (0.296 g, 0.9 mmol), dicyclohexyl carbodiimide (0.19 g, 1 mmol), 4-(dimethylamino)-pyridine (0.01 g, 0.08 mmol) and dichloromethane (10 mL) were added to a flask and stirred at room temperature for 24 hours. The solid produced was removed by filtration and the remaining solution was concentrated. The resulting solid crude product was purified by flash chromatography (2/8 ethyl acetate/hexanes, volume ratio). The recovered solid was further purified by dissolution in CHCl$_3$ and precipitation from methanol yield a grayish purple solid (0.81 g, yield 88%).

An NMR spectrum showed that the final product had a structure consistent with 3-phenyl-3-(4-(4-phenylpiperazin-1-yl)phenyl)-13,13-dimethyl-6-methoxy-7-(4-(4-(4'-octyloxy-biphenyl-4-carbonyloxy)phenyl)piperazin-1-yl)indeno[2',3':3,4]naphtho[1,2-b]pyran.

P/D-2

Step 1

4-Hydroxybenzoic acid (45 g, 0.326 mol), dodecylbenzenesulfonic acid (2 drops) and ethyl ether (500 mL) were added to a flask and stirred at room temperature. Neat dihydropyran (DHP)(35 mL, 0.39 mol) was added dropwise via a dropping funnel within a 30 minute interval and a white crystalline precipitate formed. The resulting suspension was stirred overnight and the precipitate was collected by vacuum filtration. A white solid product (41 g) was recovered. An NMR spectrum showed that the resulting product had a structure consistent with 4-(2-tetrahydro-2H-pyranoxy)benzoic acid.

Step 2

The procedure set forth above for P/D-1 was used except that the product of Step 1 (above) was used in place of 4-n-octyloxybiphenyl-4'-carboxylic acid in Step 3 of the procedure for P/D-1, and flash chromatography on silica gel was not used for the product purification. Instead, the product was purified by a technique of dissolution in chloroform followed by precipitation from methanol. An NMR spectrum showed that the resulting product, a black solid, had a structure consistent with 3-phenyl-3-(4-(4-phenyl-piperazin-1-yl)phenyl)-13,13-dimethyl-6-methoxy-7-(4-(4-(4-(2-tetrahydro-2H-pyranoxy)benzoyloxy)phenyl)piperazin-1-yl)indeno[2',3':3,4]naphtho[1,2-b]pyran.

Step 3

The product of Step 2 (11 g), pyridinium p-toluenesulfonate (0.27 g), ethyl acetate (250 mL) and methanol (40 mL) were added to a reaction flask and refluxed for 24 hours. The resulting reaction mixture was extracted with water, dried over magnesium sulfate, concentrated and flash-chromatographed using 3/7 (volume/volume) ethyl acetate/hexane as the eluant. The recovered solid was added to a flask containing chloroform (50 mL) and stirred for 30 minutes and then precipitated from methanol (8.32 g).

Step 4

The product of Step 3 (1 g, 1.1 mmol), 2-fluorobenzoyl chloride (0.5 g, 3.2 mmol) and pyridine (20 mL) were added to a reaction flask and stirred at room temperature for 4 hours. The resulting mixture was poured into a beaker containing 300 mL of water. The resulting precipitate was collected by vacuum filtration, dissolved in chloroform, dried over magnesium sulfate, concentrated and flash-chromatographed from silica gel using as an eluant: 2/8 (volume/volume) ethyl acetate/hexanes. The recovered solid was further purified by dissolution in CHCl$_3$ and precipitation from methanol to yield a gray solid (0.99 g).

An NMR spectrum showed that the final product, a purple solid, had a structure consistent with 3-phenyl-3-(4-(4-phenyl-piperazin-1-yl)phenyl)-13,13-dimethyl-6-methoxy-7-(4-(4-(4-(2-fluorobenzoyloxy)benzoyloxy)phenyl)piperazin-1-yl)indeno[2',3':3,4]naphtho[1,2-b]pyran.

P/D-3

Step 1

4-Hydroxypiperidine (19.5 g, 0.193 mol), 2,3-dimethoxy-7,7-dimethyl-7H-benzo[c]fluoren-5-ol (41.17 g, 0.128 mol) and THF (300 mL) were added to a 2 liter round-bottomed flask equipped with a bubbler and stirred magnetically at room temperature. A solution of 3 M methyl Grignard in THF (171 mL, 0.514 mmol) was added to the mixture slowly via a dropping funnel under a nitrogen atmosphere. The resulting mixture was concentrated to a viscous oil. The viscous oil was maintained under reflux and stirred for 5 days. Thin layer chromatography showed that 2 products were present in the reaction. The resulting reaction mixture was poured into a beaker containing water (1000 mL), neutralized with HCl (3 N) to a pH value of 4-6, extracted with ethyl acetate and flash-chromatographed using 2:8 (volume:volume) ethyl acetate:hexanes as the eluant. Both products were collected and obtained as white solids. An NMR spectrum showed that the major product had a structure consistent with 7,7-dimethyl-3-methoxy-7H-benzo[c]fluorene-2,5-diol and the minor product had a structure consistent with 7,7-dimethyl-3-methoxy-3-(4-hydroxypiperadin-1-yl)-7H-benzo[c]fluorene-5-ol.

Step 2

7,7-Dimethyl-3-methoxy-7H-benzo[c]fluorene-2,5-diol from Step 1 (5.1 g), 1-phenyl-1-(4-pyrrolidin-1-yl-phenyl)-prop-2-yn-1-ol (5.1 g), pyridinium p-toluenesulfonate (0.2 g), trimethyl orthoformate (4 g) and chloroform (100 mL) were added to a reaction flask and stirred at room temperature over the weekend. The reaction mixture was then concentrated and flash-chromatographed using 2:8 (volume:volume) ethyl acetate:hexanes as the eluant. A gray solid (9.1 g) was recovered. An NMR spectrum showed that the resulting product had a structure consistent with 3-phenyl-3-(4-(pyrrolidin-1-yl)phenyl)-13,13-dimethyl-6-methoxy-7-hydroxy-indeno[2',3':3,4]naphtho[1,2-b]pyran.

Step 3

The procedure of P/D-1 Step 3 was used, except that: the product of Step 2 (above) was used instead of the product of Step 2 of P/D-1; the 4-(2-tetrahydro-2H-pyranoxy) benzoic acid (of P/D-2 Step 1) was used in place of 4-n-octyloxybiphenyl-4'-carboxylic acid; and flash chromatography on silica gel was not used for the product purification. Instead, the product was purified by a technique of dissolution in chloroform followed by precipitation from methanol.

Step 4

The procedures of P/D-2 Steps 3 and 4 were followed, in sequence, using the product of Step 3 (above). An NMR spectrum showed that the final product, a blue solid, had a structure consistent with 3-phenyl-3-(4-(pyrrolidin-1-yl)phenyl)-13,13-dimethyl-6-methoxy-7-(4-(4-hexylbenzoyloxy)benzoyloxy)-indeno[2',3':3,4]naphtho[1,2-b]pyran.

Part C: Preparation of Coatings Compositions

After preparation, each of the photochromic-dichroic compounds (P/D-1 to P/D-3) was used to prepare a coating composition (indicated in Table II below as Coating Nos. 1 to 3, which correspond to P/D-1 to P/D-3, respectively) containing a photochromic-dichroic compound and the LCMS from Part A as described below. In addition, a coating composition (indicated in Table 1 as Coating No. 4) was prepared using Photosol 0265, which is commercially available from PPG Industries and reported to be 1,3,3,4,5 (or 1,3,3,5,6)-pentamethyl-spiro[indoline-2,3-[3H]naphth[2,1-b][1,4]oxazine, and the LCMS from Part A.

Each coating composition was prepared by adding an amount of the photochromic-dichroic compound to the LCMS prepared in Part A required to result in a coating composition having, in percent by weight based on the total solids of the coating solution: 4.0 percent of the photochromic-dichroic compound; 1.0 percent of Irgacure 819, a photoinitiator available from Ciba-Geigy Corporation; 1.0 percent of TINUVIN-144, a light stabilizer for coatings from Ciba-Geigy; and 0.5 percent of the surfactant sold as BYK®-346 additive by BYK Chemie, USA.

Part D: Preparation of Coated Substrates by Alignment with Orientation Facility

Step 1

Ten (10) square test substrates measuring 2"×2"×0.25" (5.08 cm×5.08 cm×0.635 cm) each of which were prepared from either CR-39® monomer or TRIVEX™ brand lens material (both of which are available from PPG Industries, Inc.). These test substrates are indicated as Substrate Sample Nos. 1x-10x in Table II, wherein x="A" for substrates made from CR-39® monomer and x="B" for substrates made from a TRIVEX™ brand lens material. One test substrate (designated Substrate Sample No. 11C) was a 1.5 mm×76 mm diameter piano, GENTEX™ polycarbonate lens (which is available from Gentex Optics). All of the aforementioned substrates were washed using liquid soap and water, rinsed with deionized water, and subsequently rinsed with isopropyl alcohol. Two (2) of test substrates (labeled Substrate Sample Nos. 9A & 10A in Table II) that were used in the magnetic alignment procedure described below in Part E were further cleaned in an ultrasonic bath with 12.5 weight percent sodium hydroxide for 30 minutes and rinsed with deionized water. All of the cleaned substrates were dried and treated with oxygen plasma at a flow rate of 100 milliliters (mL) per minute of oxygen at 100 watts of power for one minute.

Substrate Sample Nos. 9A & 10A were also treated with the adhesive layer forming composition of U.S. Pat. No. 6,150,430 by application of the adhesive layer forming composition for 10 seconds to the substrates spinning at 1500 rpm. After application, the adhesive layer forming composition was cured in a Light-Welder® 5000-EC UV light source from Dymax Corp., at a distance of 4 inches from the light for 10 seconds. The test substrates treated in this manner are identified as (Magnetic) in Table 1.

Step 2

After preparation according to Step 1, an orientation facility was formed on at least a portion of a surface of each of Substrate Sample Nos. 1x-8x, and 11C, as follows. A solution of a photo-orientable polymer network available as Staralign™ 2200 CP4 solution from Huntsman Advanced Materials, which designation is reported to mean 4 weight percent in cyclopentane, was dispensed for 2 to 3 seconds onto each of the test substrates indicated above. As the Staralign™ solution was dispensed onto the substrates, Substrate Sample Nos. 1x-8x were spun at 800 revolutions per minute for about 2 to 3 minutes, while Substrate Sample No. 11C was spun at 500 revolutions per minute for 3 minutes. Afterwards, each of the substrates was placed in an oven maintained at 130° C. for 20 to 30 minutes.

After applying the photo-orientable polymer network to Substrate Sample Nos. 1x-8x and 11C, at least a portion of the photo-orientable polymer network was at least partially ordered by exposure to linearly polarized ultraviolet light for 1 minute for Substrate Sample No. 11C, and 2 minutes for all of the other substrates, at a peak intensity of 18 milliWatts/$cm^2$ of UVA (320-390 nm) as measured using a UV Power Puck™ electro-optic radiometers from Electronic Instrumentation and Technology, Inc. The source of ultraviolet light was a BLAK-RAY Model B-100 A Longwave UV Lamp. After ordering at least a portion of the photo-orientable polymer network, the substrates were cooled to room temperature and kept covered.

Step 3

Sample Coating Nos. 1-4 were then formed on Substrate Sample Nos. 1x-8x, 11C, prepared in Steps 1 and 2 of Part D (above) using one of the coating composition prepared above in Part C as follows. To form each of the coatings, the appropriate coating composition was applied to at least a portion of the orientation facility on the surface of one of the substrates (as indicated in Table II) by spincoating. More specifically, approximately 1 mL of the coating composition was dispensed onto at least a portion of the orientation facility as the substrate, and any excess was drained off prior to spinning at 500 revolutions per minute for 3 minutes for all of the substrate samples, except Substrate Sample No. 11C, which was spun at 300 to 400 revolutions per minute for 4 to 6 minutes. After applying the coating composition, the substrate was placed in a 55° C. oven for 20 to 50 minutes to permit at least a portion of the liquid crystal material and at least a portion of the photochromic-dichroic compound to align.

After alignment, the at least partial coating was tested for alignment using two cross-polarized films (#45669) from Edmund Industrial Optics as follows. The coated substrate was positioned between the cross-polarized films so that the coated substrate was parallel with at least one of the films. Visible light transmitted through this orientation is reduced. At least partial alignment was verified by observing an increase in the transmitted visible light when one of the polarizing films was rotated 45 degrees clockwise or counterclockwise while viewing a visible light source through this configuration.

After verifying at least partial alignment, each of the at least partial coatings was cured by covering the coated substrate with a cut-off filter to screen out the ultraviolet wavelengths less than 390 nanometers such that the cut-off filter was about 1 mm above the surface of the coated substrate. The resulting assembly was placed on an ultraviolet conveyor curing line (obtained from Eye Ultraviolet, Inc) and conveyed at three feet per minute beneath two ultraviolet "type D" 400 watt/inch iron iodide doped mercury lamps of 10 inches in length, one positioned 2.5 inches above the conveyor and the other positioned 6.5 inches above the conveyor. The peak intensity of UVA (320 to 390 nm) and UVV (395 to 445 nm) in the curing line was 0.239 Watts/cm$^2$ and of UW was 0.416 Watts/cm$^2$, respectively, as measured using UV Power Puck™ electro-optic radiometers. The UV conveyor curing line had a nitrogen atmosphere in which the oxygen level was less than 100 ppm.

Part E: Preparation of Ordered Coating by Exposure to a Magnetic Field

Sample Substrate Nos. 9A and 10A, which were coated with the adhesive layer as described above in Part D, were used in this Part E. The procedure of Part D used for Sample Substrate No. 11 was followed to form coatings of coating compositions 2 and 3 on Substrate Nos. 9A and 10A, respectively, except that after application of the coating composition and prior to curing, the coated substrate was placed on a temperature controlled hot plate 8 inches beneath a temperature controlled infrared lamp and between the North and South poles of a 0.35 Tesla magnet that were separated by a distance of 11 centimeters. Both temperature controllers were set to maintain a temperature of from approximately 55 to 60° C. The coated substrates were kept under these conditions for 10 to 15 minutes and subsequently cured as described in Part D.

Example 2

Ophthalmic substrates having an at least partial coating were prepared using an overmold process as described below.

Step 1

The procedure of Parts A & C of Example 1 were followed to form an overmolding coating composition, except that the essentially all of the solvent in the coating composition was removed by sparging with air for 2 hours prior to adding about 2 weight percent of P/D-3, on a total weight basis, to produce the overmolding coating composition.

Step 2

A six-base lens prepared from CR-39® monomer was cleaned following the procedure of Part D, Step 1 of Example 1 except that the lens was dried in an oven at 100° C. for 10 minutes prior to treatment with oxygen plasma.

Step 3

The procedure of Part D, Step 2 of Example 1 was followed to form an orientation facility comprising a coating of an at least partially ordered photo-orientable polymer network to the lens and a glass mold, except that a 90 second exposure to the linearly polarized ultraviolet light was used.

Step 4

After forming the orientation facilities as described above, the glass mold was positioned on a flat surface with the orientation facility facing up. An amount of the overmolding solution sufficient to cover the mold surface as poured into the center of the mold. Teflon® circular sleeves were placed on the edges of the mold for use as spacers. The lens was positioned adjacent the mold such that the orientation facility on the lens contacted the overmolding solution, and the overmolding solution spread out to fill the region between the lens and the mold. Clamps were applied to form an assembly that was placed in an oven at 45° C. for 30 minutes to permit the liquid crystal material to at least partially align with the orientation facilities. Thereafter, the assembly was placed on the ultraviolet conveyor curing line described in Step 3, Part D of Example 1. After curing, the coated lens was released from the mold. Examination of the coated lens using the cross-polar films described above in Step 3, Part D of Example 1 to observe alignment of the coating. Absorption ratio measurements were made for the coatings (as described below) and dichroism was observed.

The thickness of the overmolded coating was determined as follows. Two cross-sections were obtained from the lens, one near the center of the lens and one near the outer edge of the lens. The cross-sections were coated with a 1.550 refractive index liquid, placed on a microscope slide and covered with a slip cover. Measurements of the coating thickness were then taken using a Leitz polarized light microscope and a Spot digital camera. Based on these measurements, the coating was determined to have a thickness near the center of the lens ranging from 127+/−5 microns to 130+/−5 microns and a thickness near the outer edge of the lens ranging from 118+/−5 microns to 120+/−5 microns.

Example 3

An optical bench was used to measure the average absorption ratios for each of the coated samples prepared in Examples 1 and 2 above as follows. Each of the coated samples was placed on the optical bench with an activating light source (an Oriel Model 66011 300-Watt Xenon arc lamp fitted with a Melles Griot 04 IES 211 high-speed computer controlled shutter that momentarily closed during data collection so that stray light would not interfere with the data collection process, a Schott 3 mm KG-2 band-pass filter, which removed short wavelength radiation, neutral density filter(s) for intensity attenuation and a condensing lens for beam collimation) positioned at a 30° angle of incidence to the surface of the coated substrate.

A broadband light source for monitoring response measurements was positioned in a perpendicular manner to the surface of the coated substrate. Increased signal of shorter visible wavelengths was obtained by collecting and combining separately filtered light from a 100-Watt tungsten halogen lamp (controlled by a Lambda UP60-14 constant voltage power supply) with a split-end, bifurcated fiber optical cable. Light from one side of the tungsten halogen lamp was filtered with a Schott KG1 filter to absorb heat and a Hoya B-440 filter to allow passage of the shorter wavelengths. The other side of the light was either filtered with a Schott KG1 filter or unfiltered. The light was collected by focusing light from each side of the lamp onto a separate end of the split-end, bifurcated fiber optic cable, and subsequently combined into one light source emerging from the single end of the cable. A 4" light pipe was attached to the single end of the cable insure proper mixing.

Linear polarization of the light source was achieved by passing the light from the single end of the cable through a Moxtek, Proflux Polarizer held in a computer driven, motorized rotation stage (Model M-061-PD from Polytech, PI). The monitoring beam was set so that the one polarization plane (0°) was perpendicular to the plane of the optical bench table and the second polarization plane (90°) was parallel to the plane of the optical bench table. The samples were run in air, at room temperature (73° F.±5° F.) maintained by the lab air conditioning system or a temperature controlled air cell.

To conduct the measurements, the coated substrate was exposed to 6.7 W/m$^2$ of UVA from the activating light source for 5 to 15 minutes to activate the photochromic-dichroic compound. An International Light Research Radiometer (Model IL-1700) with a detector system (Model SED033 detector, B Filter, and diffuser) was used to verify exposure prior to each test. Light from the monitoring source that was polarized in the 0° polarization plane was then passed through coated sample and focused on a 2" integrating sphere, which was connected to a Ocean Optics 2000 spectrophotometer using a single function fiber optic cable. The spectral information after passing through the sample was collected using Ocean Optics OOIBase32 and OOIColor software, and PPG propriety software. While the photochromic-dichloric compound was activated, the position of the polarizing sheet was rotated back and forth to polarize the light from the monitoring light source to the 90° polarization plane and back. Data was collected at 3-second intervals during activation. For each test, rotation of the polarizers was adjusted to collect data in the following sequence of polarization planes: 0°, 90°, 90°, 0° etc.

Absorption spectra were obtained and analyzed for each coated substrate using the Igor Pro software (available from WaveMetrics). The change in the absorbance for each coated substrate was calculated by subtracting out the 0 time (i.e., unactivated) absorption measurement for each wavelength tested. Average absorbance values were obtained in the region of the activation profile where the photochromic response was saturated or nearly saturated (i.e., the regions where the absorbance did not increase or did not increase significantly over time) for each coated substrate by averaging the absorbance taken at each time interval for each coated substrate in this region (for each wavelength extracted were average of 5 to 100 data points). The average absorbance values in a predetermined range of wavelengths corresponding $\lambda_{max\text{-}vis}+/-5$ nm were extracted for the 0° and 90° polarizations, and the absorbption ratio for each wavelength in this range was calculated by dividing the larger average absorbance by the small average absorbance. For each wavelength extracted, 5 to 100 data points were averaged. The average absorption ratio for the sample was then calculated by averaging these individual absorption ratios.

For each sample Substrate listed in Table II, the above-described procedure was run twice. The table value for the Average Absorption Ratio represents an average of the results obtained from these two runs.

TABLE II

| Sample Substrate No. | Sample Coating No. | Wavelength of Maximum Absorption Peak at which AR measured | Average Absorption Ratio |
|---|---|---|---|
| 1A | 1 | 500 | 5.4 |
|    | 1 | 599 | 5.4 |
| 2B | 1 | 500 | 5.5 |
|    | 1 | 601 | 5.5 |
| 3A | 2 | 500 | 4.9 |
|    | 2 | 599 | 4.8 |
| 4B | 2 | 500 | 4.7 |
|    | 2 | 599 | 4.7 |
| 5A | 3 | 497 | 2.1 |
|    | 3 | 636 | 2.8 |
| 6B | 3 | 497 | 2.1 |
|    | 3 | 638 | 2.9 |
| 7A | 4 | 590 | 2.8 |
| 8B | 4 | 625 | 2.7 |
| 9A | 2(MAGNETIC) | 499 | 3.0 |
|    | 2(MAGNETIC) | 600 | 3.0 |
| 10A | 3(MAGNETIC) | 497 | 1.7 |
|     | 3(MAGNETIC) | 636 | 2.2 |
| 11C | 2 | 501 | 2.5 |
|     | 2 | 595 | 2.6 |

Example 4

The average absorption ratio of each photochromic-dichroic compounds P/D-1 through P/D-3, as well as the average absorption ratio of Photosol™ 0265 ("Comparative Compound"), which is commercially available from PPG Industries, Inc. and reported to be 1,3,3,4,5 (or 1,3,3,5,6)-pentamethyl-spiro[indoline-2,3-[3H]naphth[2,1-b][1,4]oxazine, was measured using the CELL METHOD. According to the CELL METHOD, the optical bench and procedure described above in Example 3 for measuring the average absorption ratio of the coatings was used, except that a cell assembly (described below) containing the compound to be tested and a liquid crystal material was positioned on the optical bench (instead of the coated substrate).

A cell assembly having the following configuration was obtained from Design Concepts, Inc. Each of the cell assemblies was formed from two opposing glass substrates that are spaced apart with a glass bead spacer having a diameter of 20 microns+/−1 micron. The inner surfaces of each of the glass substrates had oriented polyimide coating thereon to provide for the alignment of a liquid crystal material as discussed below. Two opposing edges of the glass substrates were sealed with an epoxy sealant, leaving the remaining two edges open for filling. The gap between the two glass substrates of the cell assembly was filled with a liquid crystal solution containing one of the Test Materials (i.e, the photochromic-dichroic compounds (P/D-1 to P/D-3) or the Comparative Compound). The liquid crystal solution was formed by mixing the following components in the weight percents listed in Table III with heating, if necessary, to dissolve the test material.

TABLE III

| Component | Weight Percent |
|---|---|
| Licristal ™ E7 | 97-99.5 |
| Test Material | 0.5-3 |

For each Test Material, the above-described procedure was run at least twice. The tabled value for the Average Absorption Ratio represents an average of the results obtained from the runs. The results of these tests are present in Table IV below.

TABLE IV

| Example Number | Wavelength Range $\lambda_{max\text{-}vis}$ (nm) +/− 5 nm | Average Absorption Ratio (AR) |
|---|---|---|
| Comparative Example | 623 +/− 5 nm | 2.3 |
| P/D-1 | 497 +/− 5 nm | 6.3 |
| P/D-2 | 497 +/− 5 nm | 5.8 |
| P/D-3 | 639 +/− 5 nm | 5.9 |

Example 5

The average absorption ratio of the photochromic-dichroic compounds in Table V (below) were determined as set forth above. It will be appreciated by those skilled in that the compound listed in Table V may be made in accordance with the teachings and examples disclosed herein with appropriate modifications, which will be readily apparent to those skilled in the art. Further, those skilled in the art will recognize that various modifications to the disclosed methods, as well as other methods, can be used in making the named compounds set forth below in Table V.

TABLE V

| Compound Name | Wavelength Range λ_max (nm) (+/−5 nm) | Average Absorption Ratio (AR) |
|---|---|---|
| 3-phenyl-3-(4-(4-(3-piperidin-4-yl-propyl)piperidino)phenyl)-13,13-dimethyl-indeno[2',3':3,4]-naphtho[1,2-b]pyran | 590 | 2.0 |
| 3-phenyl-3-(4-([1,4']bipiperidinyl-1'-yl)phenyl)-13,13-dimethyl-6-methoxy-7-([1,4']bipiperidinyl-1'-yl)indeno[2',3':3,4]naphtho[1,2-b]pyran | 513 | 3.4 |
| 3-phenyl-3-(4-(4-phenyl-piperazin-1-yl)phenyl)-13,13-dimethyl-6-methoxy-7-(4-(4-hexylbenzoyloxy)-piperidin-1-yl)indeno[2',3':3,4] naphtho[1,2-b]pyran | 503 | 3.9 |
| 3-phenyl-3-(4-(4-phenyl-piperazin-1-yl)phenyl)-13,13-dimethyl-6-methoxy-7-(4-(4'-octyloxy-biphenyl-4-carbonyloxy)-piperidin-1-yl)indeno[2',3':3,4]naphtho[1,2-b]pyran | 499 | 4.1 |
| 3-phenyl-3-(4-(4-(4-butyl-phenylcarbamoyl)-piperidin-1-yl) phenyl)-13,13-dimethyl-6-methoxy-7-(4-phenyl-piperazin-1-yl)indeno[2',3':3,4] naphtho[1,2-b]pyran | 506 | 5.0 |
| 3-phenyl-3-{4-(pyrrolidin-1-yl)phenyl)-13,13-dimethyl-6-methoxy-7-(4-(4-(3-phenyl-3-{4-(pyrrolidin-1-yl)phenyl}-13,13-dimethyl-6-methoxy-indeno[2',3':3,4]naphtho[1,2-b]pyran-7-yl)-piperadin-1-yl)oxycarbonyl)phenyl)phenyl)cabonyloxy)-indeno[2',3':3,4]naphtho[1,2-b]pyran; | 628 | 4.8 |
| 3-phenyl-3-(4-(4-phenyl-piperazin-1-yl)phenyl)-13,13-dimethyl-6-methoxy-7-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-indeno[2',3':3,4]naphtho[1,2-b]pyran | 502 | 6.0 |
| 3-phenyl-3-{4-(pyrrolidin-1-yl)phenyl)-13-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxy]-13-ethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperadin-1-yl)-indeno[2',3':3,4]naphtho[1,2-b]pyran | 529 | 3.3 |
| 3-phenyl-3-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-phenyl)-13-ethyl-13-hydroxy-6-methoxy-7-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-)indeno[2',3':3,4]naphtho[1,2-b]pyran | 507 | 6.0 |
| 3-phenyl-3-(4-(4-phenyl-piperazin-1-yl)phenyl)-13,13-dimethyl-6-methoxy-7-(4-(4-(4-hexyloxyphenylcarbonyloxy)phenyl) piperazin-1-yl)indeno[2',3':3,4]naphtho[1,2-b]pyran | 496 | 5.8 |
| 3-phenyl-3-(4-(4-methoxyphenyl)-piperazin-1-yl))phenyl)-13,13-dimethyl-6-methoxy-7-(4-(4-(3-phenylprop-2-ynoyloxy)phenyl)piperazin-1-yl)-indeno[2',3':3,4]naphtho[1,2-b]pyran | 499 | 6.3 |
| 3-phenyl-3-(4-(pyrrolidin-1-yl)phenyl)-13-hydroxy-13-ethyl-6-methoxy-7-(4-(4-(4-hexylbenzoyloxy)phenyl)piperazin-1-yl)indeno[2',3':3,4] naphtho[1,2-b]pyran | 629 | 6.3 |
| 3-phenyl-3-(4-(pyrrolidin-1-yl)phenyl)-13,13-dimethyl-6-methoxy-7-(4-(4-hexylbenzoyloxy)benzoyloxy)benzoyloxy)indeno[2',3':3,4] naphtho[1,2-b]pyran | 646 | 6.4 |
| 3-(4-methoxyphenyl)-3-(4-(4-methoxyphenyl)piperazin-1-yl)phenyl)-13-ethyl-13-hydroxy-6-methoxy-7-(4-(4-(4-hexylbenzoyloxy)phenyl)piperazin-1-yl)indeno[2',3':3,4]naphtho[1,2-b]pyran | 499 | 5.4 |
| 2-phenyl-2-{4-[4-(4-Methoxy-phenyl)-piperazin-1-yl]-phenyl}-9-hydroxy-8-methoxycarbonyl-2H-naphtho[1,2-b]pyran | 571 | 2.7 |
| 2-phenyl-2-{4-[4-(4-Methoxy-phenyl)-piperazin-1-yl]-phenyl}-9-hydroxy-8-(N-(4-butyl-phenyl))carbamoyl-2H-naphtho[1,2-b]pyran | 590 | 4.0 |
| 2-phenyl-2-{4-[4-(4-Methoxy-phenyl)-piperazin-1-yl]-phenyl}-9-hydroxy-8-(N-(4-phenyl)phenyl) carbamoyl-2H-naphtho[1,2-b]pyran | 566 | 3.9 |

TABLE V-continued

| Compound Name | Wavelength Range $\lambda_{max}$ (nm) (+/−5 nm) | Average Absorption Ratio (AR) |
|---|---|---|
| 2-phenyl-2-{4-[4-(4-Methoxy-phenyl)-piperazin-1-yl]-phenyl}-benzofuro[3',2':7,8] benzo[b]pyran | 583 | 4.2 |
| 2-phenyl-2-{4-[4-(4-Methoxy-phenyl)-piperazin-1-yl]-phenyl}-benzothieno[3',2':7,8] benzo[b]pyran | 510 | 4.1 |
| 1,3,3-trimethyl-6'-(4-ethoxycarbonyl)-piperidin-1-yl)-spiro[indoline-2,3'-3H-naphtho[2,1-b][1,4]oxazine] | 590 | 6.0 |
| 1,3,3-trimethyl-6'-(4-[N-(4-butylphenyl)carbamoyl]-piperidin-1-yl)-spiro[indoline-2,3'-3H-naphtho[2,1-b][1,4]oxazine] | 590 | 7.8 |
| 3-phenyl-3-(4-pyrrolidinylphenyl)-13,13-dimethyl-6-methoxy-7-(4-(4-(4-(6-(4-(4-(4-nonylphenylcabonyloxy)phenyl)oxycarbonyl)phenoxy)hexyloxy)phenyl)piperazin-1-yl)indeno[2',3':3,4] naphtho[1,2-b]pyran | 627 | 6.5 |
| 1,3,3-trimethyl-6'-(4-(4-methoxyphenyl)piperazin-1-yl)-spiro[indoline-2,3'-3H-naphtho[2,1-b][1,4]oxazine]; | 586 | 8.3 |
| 1,3,3-trimethyl-6'-(4-(4-hydroxyphenyl)piperazin-1-yl)-spiro[indoline-2,3'-3H-naphtho[2,1-b][1,4]oxazine]; | 587 | 7.0 |

Example 6

Electro-optic cell assemblies according to various non-limiting embodiments disclosed herein were prepared as follows.

Step 1

Unpolished float glass slides measuring 25×50×1.1 mm having an indium tin oxide ("ITO") coating on one surface, $R_s \leq 100\Omega$, obtained from Delta Technologies, Limited, were used. The ITO coated surface of two slides was further coated polyimide coating solution that was prepared as follows. The components listed in Table VI, were added in the order listed to a beaker. After all of the components were added, the composition was mixed until the components were dissolved.

TABLE VI

| Components | Weight (grams) |
|---|---|
| PI2255[1] | 80 |
| 3-ethoxypropanol | 80 |
| NMP[2] | 320 |

[1] Polyimide available from DuPont.
[2] N-methylpyrrolidone.

The polyimide coating solution was applied to the ITO coated surface of the glass slides by spin coating. 1.5 milliliters (mL) of the coating solution was dispensed onto the glass slides spinning at 1000 rpm for 90 seconds.

Step 2

The coated slides of Step 1 were held at 130° C. for 15 minutes, after which the temperature was increased to 250° C. and held at the elevated temperature for at least 90 minutes. The slides were removed and allowed to cool to room temperature.

Step 3

The coated slides of Step 2 were put into a holder with the coated side up. The surface of the coated slide was gently brushed with a velvet brush in the lengthwise direction several times to remove any dirt. Afterwards, the coated slide was brushed ten more times applying enough pressure to form parallel groves in the coating. Glass spheres having a diameter of 20 microns were applied to one of the coated slides to serve as spacers when the other coated slide was positioned to form a parallel rubbed cell having a portion of each slide extending over the other so that electrical connections could be made to each slide. The resulting electro-optic cell assembly was clamped.

Step 4

The lengthwise edges of the electro-optic cell assembly of Step 3 were coated with Devon Epoxy Glue, the components of which had been previously mixed in a 1:1 ratio. The glued electro-optic cell assembly was left at room temperature for one hour and then heated for at least one hour at least 100° centigrade.

Step 5

The electro-optic cell assembly of Step 4 was filled with a photochromic liquid crystal coating solution using a capillary tube to apply the solution until the cell assembly was filled. The photochromic liquid crystal solution was prepared by the addition of a small amount of P/D-3 to a few drops of Licristal™ E7 available from EM Industries.

Example 7

The average absorption ratios for the electro-optic cell assemblies of Example 4 were determined as follows. The aforedescribed optical bench was modified with a conductive electro-optic cell-mounting device that served to hold the electro-optic cell in place and allow an electrical flow of 8 volts DC applied through a Lambda Model LLS5018 power supply to pass through it. The modified optical bench was used to obtain the response measurements and derive absorbance ratios of P/D-3 in the Licristal™ E7 liquid crystal solution used in the electro-optic cell assembly following the procedure of Example 3, except as follows.

The electro-optic cell assembly was activated for 10 minutes with no current applied and the average absorption ratio was determined. Application of an 8-volt DC flow to the electro-optic cell assembly while still being activated by the filtered Xenon light was done for an additional 10 minutes and the average absorption ratio was determined again. The results are listed in Table VII.

TABLE VII

| Voltage State | Wavelength of Maximum Absorption Peak at which AR measured | Average Absorption Ratio |
| --- | --- | --- |
| No Voltage | 501 | 3.4 |
| No Voltage | 647 | 5.3 |
| Voltage | 501 | 1.7 |
| Voltage | 647 | 1.5 |

The results of Table VII show that the electro-optic cell assembly exhibited absorptions ratios from 3.4 to 5.3 over the wavelength range of 501 to 647 nm while exposed to photochromic activating radiation without the application of voltage and that the application of voltage (8 volts of direct current) caused a reduction in the average absorption ratios to 1.7 to 1.5 over the same wavelength range while the exposure to photochromic activating radiation continued.

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, the present invention is not limited to the particular embodiments disclosed, but is intended to cover modifications that are within the spirit and scope of the invention, as defined by the appended claims.

We claim:

1. A method of making an optical element comprising forming an at least partial coating comprising at least one thermally reversible photochromic-dichroic compound at least partially aligned on at least a portion of a substrate wherein forming said partial coating comprises:

applying at least one anisotropic material to at least a portion of the substrate;

imbibing the at least one thermally reversible photochromic-dichroic compound into at least a portion of the at least one anisotropic material;

at least partially ordering at least a portion of the anisotropic material; and at least partially aligning at least a portion of the at least one thermally reversible photochromic-dichroic compound with at least a portion of the at least partially ordered anisotropic material.

2. The method of claim 1 wherein imbibing the at least one thermally reversible photochromic-dichroic compound into at least a portion of the at least one anisotropic material occurs at least one of: before, during or after at least partially ordering at least a portion of the anisotropic material.

3. The method of claim 1 further comprising imparting at least one orientation facility on at least a portion of a substrate prior to forming the at least partial coating comprising at least one thermally reversible photochromic-dichroic compound at least partially aligned on the at least a portion of a substrate such that at least a portion of the at least one orientation facility is between at least a portion of the at least partial coating and at least a portion of the substrate.

4. The method of claim 3 wherein imparting the at least one orientation facility on the at least a portion of the substrate comprises at least one of:

forming an at least partial coating comprising an at least partially ordered alignment medium on the at least a portion of the substrate; applying an at least partially ordered polymer sheet to the at least a portion of the substrate; at least partially treating at least a portion of at least one surface of the substrate; and forming a Langmuir-Blodgett film on at least a portion of the substrate.

5. The method of claim 3 wherein imparting the at least one orientation facility on the at least a portion of the substrate comprises forming an at least partial coating comprising an at least partially ordered alignment medium on the at least a portion of the substrate, wherein the alignment medium is chosen from photo-orientation materials, rubbed-orientation materials, and liquid crystal materials.

6. The method of claim 5 wherein forming the at least partial coating comprising the at least partially ordered alignment medium comprises applying an alignment medium to at least a portion of the substrate and at least partially ordering at least a portion of the alignment medium.

7. The method of claim 6 wherein at least partially ordering at least a portion of the alignment medium comprises at least one of: exposing the at least a portion of the alignment medium to linearly polarized ultraviolet radiation;

exposing the at least a portion of the alignment medium to linearly polarized infrared radiation; exposing the at least a portion of the alignment medium to linearly polarized visible radiation; exposing the at least a portion of the alignment medium to a magnetic field; exposing the at least a portion of the alignment medium to an electric field; etching the at least a portion of the alignment medium; exposing the at least a portion of the alignment medium to a shear force; and rubbing the at least a portion of the alignment medium.

8. The method of claim 5 wherein the alignment medium is a photo-orientation material, and at least partially ordering at least a portion of the alignment medium comprises exposing at least a portion of the photo-orientation material to linearly polarized ultraviolet radiation.

9. The method of claim 8 wherein forming the at least partial coating comprising that at least partially ordered alignment medium further comprises at least partially setting at least a portion of the alignment medium after at least partially ordering at least a portion of the alignment medium by at least one of at least partially drying the at least a portion of the alignment medium, at least partially cross-linking the at least a portion of the alignment medium, and at least partially curing the at least a portion of the alignment medium.

10. The method of claim 9 wherein at least partially curing the at least a portion of the alignment medium comprises at least one of ultraviolet curing, electron beam curing, and thermal curing.

11. The method of claim 3 wherein forming the at least partial coating comprising the at least one at least partially aligned photochromic-dichroic compound comprises:

applying a polymerizable composition, at least one anisotropic material, and at least one thermally reversible photochromic-dichroic compound to at least a portion of the at least one orientation facility;

aligning at least a portion of the at least one anisotropic material with at least a portion of the at least one orientation facility; and aligning at least a portion of the at least one thermally reversible photochromic-dichroic compound with at least a portion of the at least partially aligned at least one anisotropic material.

12. The method of claim 11 further comprising at least partially setting at least a portion of the at least one anisotropic material by exposing at least a portion of the at least partial coating to ultraviolet radiation and at least partially setting at least a portion of the polymerizable composition by exposing at least a portion of the at least partial coating to thermal energy.

13. The method of claim 12 wherein at least partially setting at least a portion of the at least one anisotropic material occurs at least one of: before, during or after at least partially setting at least a portion of the polymerizable composition.

14. The method of claim 12 wherein the at least one anisotropic material is a liquid crystal material and the polymerizable composition comprises dihydroxy monomers and isocyanate monomers.

15. A method of making an optical element comprising forming an at least partial coating comprising at least one thermally reversible photochromic-dichroic compound at least partially aligned on at least a portion of a substrate, wherein forming the at least partial coating comprises:
applying at least one thermally reversible photochromic-dichroic compound and at least one anisotropic material to at least a portion of the substrate;
at least partially ordering at least a portion of the anisotropic material; and
at least partially aligning at least a portion of the at least one thermally reversible photochromic-dichroic compound with at least a portion of the at least partially ordered anisotropic material.

16. The method of claim 15 wherein applying the at least one thermally reversible photochromic-dichroic compound and the at least one anisotropic material to the at least a portion of the substrate occurs at least one of:
before, during, or after at least partially ordering at least a portion of the anisotropic material and at least partially aligning at least a portion of the at least one thermally reversible photochromic-dichroic compound.

17. The method of claim 15 wherein applying the at least one thermally reversible photochromic-dichroic compound and the at least one anisotropic material comprises at least one of spin coating, spray coating, spray and spin coating, curtain coating, flow coating, dip coating, injection molding, casting, roll coating, wire coating, overmolding.

18. The method of claim 15 wherein applying the at least one thermally reversible photochromic-dichroic compound and at least one anisotropic material to at least a portion of the substrate comprises:
applying a phase-separating polymer system comprising a matrix phase forming material comprising a liquid crystal material and a guest phase forming material comprising the at least one anisotropic material and at least one thermally reversible photochromic-dichroic compound to at least a portion of the substrate;
at least partially ordering at least a portion of the matrix phase forming material and at least a portion of the guest phase forming material;
at least partially aligning at least a portion of the at least one thermally reversible photochromic-dichroic compound with at least a portion of the at least partially ordered guest phase forming material; and
causing at least a portion of the guest phase forming material to separate from at least a portion of the matrix phase forming material by at least one of polymerization induced phase separation and solvent induced phase separation.

19. The method of claim 18 wherein applying the phase-separating polymer system comprises applying a solution comprising the matrix phase forming material, the guest phase forming material, the at least one thermally reversible photochromic-dichroic compound, and at least one common solvent on the at least a portion of the optical substrate.

20. The method of claim 19 wherein:
the matrix phase forming material is a liquid crystal polymer and the guest phase forming material is a liquid crystal polymer that is different from the liquid crystal polymer of the matrix phase forming material; and
causing at least a portion of the guest phase forming material to separate from at least a portion of the matrix phase forming material comprises evaporating at least a portion of the at least one common solvent.

21. The method of claim 18 wherein:
the matrix phase forming material is a liquid crystal monomer and the guest phase forming material is chosen from a liquid crystal mesogen and a low viscosity liquid crystal monomer that is different from the liquid crystal monomer of the matrix phase forming material; and
causing at least a portion of the guest phase forming material to separate from at least a portion of the matrix phase forming material comprises polymerizing at least a portion of the liquid crystal monomer of the matrix phase forming material.

22. The method of claim 21 wherein polymerizing at least a portion of the liquid crystal monomer of the matrix phase forming material comprises at least one of photo-induced polymerization and thermally-induced polymerization.

23. The method of claim 21 wherein the guest phase forming material is a low viscosity liquid crystal monomer, and wherein at least a portion of the guest phase forming material is at least partially polymerized after polymerizing at least a portion of the liquid crystal monomer of the matrix phase forming material.

24. The method of claim 18 wherein matrix phase forming material comprises a liquid crystal material chosen from liquid crystal monomers, liquid crystal pre-polymers, and liquid crystal polymers.

25. The method of claim 18 wherein guest phase forming material comprises a liquid crystal material chosen from liquid crystal mesogens, liquid crystal monomers, liquid crystal pre-polymers, and liquid crystal polymers.

26. The method of claim 15 wherein ordering at least a portion of the at least one anisotropic material comprises exposing the at least a portion of the anisotropic material to at least of: a magnetic field, an electric field, linearly polarized ultraviolet radiation, linearly polarized infrared radiation, linearly polarized visible radiation, and a shear force.

27. The method of claim 15 further comprising at least partially setting at least a portion of the at least one anisotropic material.

28. The method of claim 27 wherein at least partially setting at least a portion of the at least one anisotropic material comprises at least partially cross-linking at least a portion of the at least one anisotropic material.

* * * * *